United States Patent
Olszewski et al.

(10) Patent No.: US 10,729,691 B2
(45) Date of Patent: *Aug. 4, 2020

(54) TREATMENT OF INFECTIOUS DISEASES WITH GLUCOSE UPTAKE INHIBITORS

(71) Applicant: Kadmon Corporation LLC, New York, NY (US)

(72) Inventors: Kellen Olszewski, Brooklyn, NY (US); Masha Poyurovsky, New York, NY (US); Anthony Barsotti, New York, NY (US); Ji-Ln Kim, Princeton, NJ (US); Kevin G. Liu, West Windsor, NJ (US)

(73) Assignee: KADMON CORPORATION, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/737,916

(22) PCT Filed: Jun. 24, 2016

(86) PCT No.: PCT/US2016/039370
§ 371 (c)(1),
(2) Date: Dec. 19, 2017

(87) PCT Pub. No.: WO2016/210331
PCT Pub. Date: Dec. 29, 2016

(65) Prior Publication Data
US 2019/0060314 A1    Feb. 28, 2019

Related U.S. Application Data

(60) Provisional application No. 62/185,231, filed on Jun. 26, 2015.

(51) Int. Cl.
| | | |
|---|---|---|
| A61K 31/519 | (2006.01) | |
| A61K 31/52 | (2006.01) | |
| C07D 239/70 | (2006.01) | |
| C07D 231/16 | (2006.01) | |
| A61K 31/5377 | (2006.01) | |
| C07D 513/04 | (2006.01) | |
| C07D 471/04 | (2006.01) | |
| C07D 491/048 | (2006.01) | |
| C07D 473/34 | (2006.01) | |
| C07D 495/04 | (2006.01) | |
| C07D 487/04 | (2006.01) | |
| C07D 491/052 | (2006.01) | |
| A61P 33/06 | (2006.01) | |

(52) U.S. Cl.
CPC .......... *A61K 31/519* (2013.01); *A61K 31/52* (2013.01); *A61K 31/5377* (2013.01); *A61P 33/06* (2018.01); *C07D 231/16* (2013.01); *C07D 239/70* (2013.01); *C07D 471/04* (2013.01); *C07D 473/34* (2013.01); *C07D 487/04* (2013.01); *C07D 491/048* (2013.01); *C07D 491/052* (2013.01); *C07D 495/04* (2013.01); *C07D 513/04* (2013.01); *Y02A 50/409* (2018.01); *Y02A 50/411* (2018.01)

(58) Field of Classification Search
USPC ...................................................... 514/260.1
See application file for complete search history.

(56) References Cited

U.S. PATENT DOCUMENTS

| | | |
|---|---|---|
| 2010/0216789 A1 | 8/2010 | Nagarathnam et al. |
| 2012/0238540 A1 | 9/2012 | Holcomb et al. |
| 2012/0277206 A1 | 11/2012 | Shaginian et al. |
| 2012/0329780 A1 | 12/2012 | Thormann et al. |
| 2014/0228286 A1 | 8/2014 | Luippold et al. |

FOREIGN PATENT DOCUMENTS

WO    2012/040499 A2    3/2012

*Primary Examiner* — Kathrien A Cruz
(74) *Attorney, Agent, or Firm* — Fox Rothschild LLP

(57) ABSTRACT

Provided are methods of treating infectious diseases in mammals comprising administering a compound that inhibits glucose uptake. Particular infectious diseases that may be treated include malaria, leishmaniasis, African trypanosomiasis, tuberculosis, HIV, HCMV or herpes virus. In a first aspect, the invention features a method of treating infectious diseases in a mammal, comprising administering to a mammalian subject in need thereof a therapeutically effective amount of a compound or prodrug thereof, or pharmaceutically acceptable salt or ester of said compound or prodrug, wherein the compound is an inhibitor of glucose uptake.

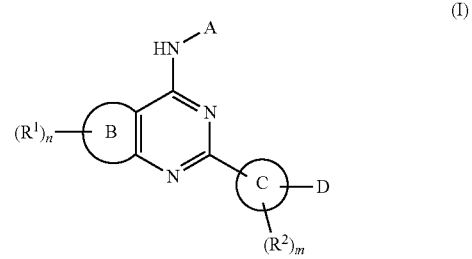

9 Claims, 3 Drawing Sheets

TREATMENT OF INFECTIOUS DISEASES WITH GLUCOSE UPTAKE INHIBITORS

FIELD OF THE INVENTION

This invention provides methods for the treatment of infectious diseases by administering compounds that modulate glucose uptake activity. Particularly, the present invention provides methods for treating infectious diseases by modulators of host cell pathways relating to glucose uptake. The invention provides methods for treating infectious diseases using inhibitors of the host cell's transport/uptake of glucose, and particularly GLUT-1.

BACKGROUND OF THE INVENTION

Glucose represents a central nutrient for many organisms, and control of glucose signaling and consumption is tightly regulated. Accordingly, many disease states are associated with defects in this regulation and therefore may be susceptible to therapeutic intervention using glucose uptake inhibitors. Glucose uptake inhibitors may have utility in disease areas such as oncology, autoimmunity and inflammation, infection diseases/virology, and metabolic disease.

SUMMARY OF THE INVENTION

In a first aspect, the invention features a method of treating infectious diseases in a mammal, comprising administering to a mammalian subject in need thereof a therapeutically effective amount of a compound or prodrug thereof, or pharmaceutically acceptable salt or ester of said compound or prodrug, wherein the compound is an inhibitor of glucose uptake. In particular aspects, the present invention provides a method of treating infectious diseases in a mammal, and preferably a human, in which the glucose uptake inhibitor modulates the glucose transport of GLUT-1.

DESCRIPTION OF THE DRAWINGS

FIG. 1 shows that cultured *Plasmodium falciparum* is sensitive to GLUT1 inhibition.

DETAILED DESCRIPTION

Figure 1A:
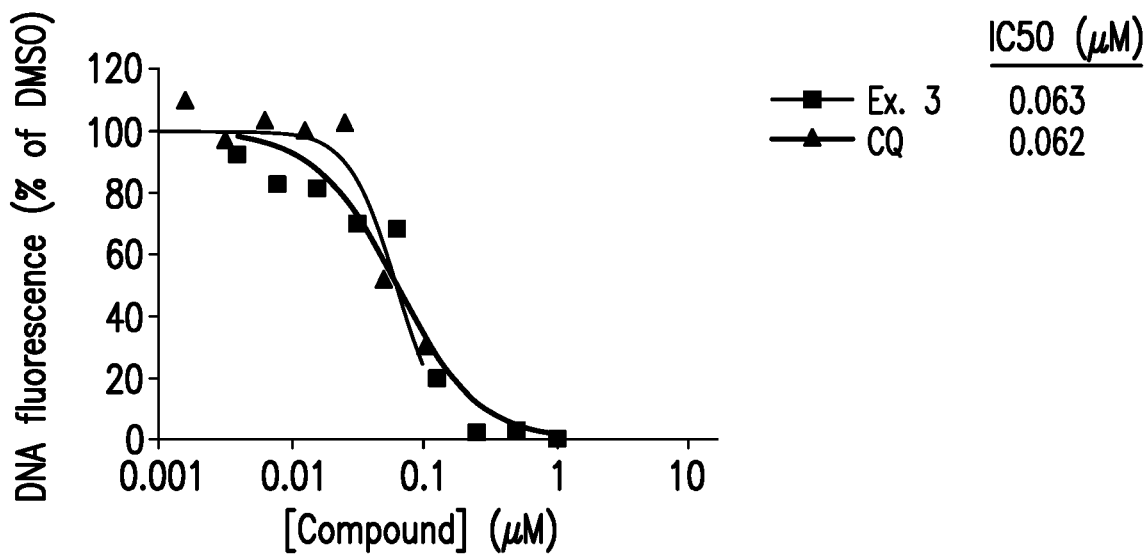
FIG. 1A shows blood cultures of *P. falciparum* (HB3 strain; 2% initial parasitemia; 1% hematocrit; O+ blood) that were seeded in 96-well culture plates and treated with the varying concentrations of the compound of Example 3 and chloroquine (CQ) in 0.1% DMSO for 48 hours. The cultures were harvested and DNA quantitated using the standard Sybr Green I fluorescence assay.

Glucose represents a central nutrient for many organisms, and control of glucose signaling and consumption is tightly regulated. Accordingly, many disease states are associated with defects in this regulation and therefore may be susceptible to therapeutic intervention using glucose uptake inhibitors. Glucose uptake inhibitors have utility in disease areas such infection diseases/virology, particularly for the treatment of disease states in which the infectious agent relies on the host's cell's glucose import.

Intracellular pathogens comprise a diverse array of viruses, bacteria and protozoan parasites which include the causative agents of many of the most clinically important infectious diseases worldwide. By invading a host cell these pathogens become tightly coupled to the host cell's cellular processes, and may be rendered critically dependent on host factors such as metabolic enzymes and transporters. Targeting these host factors provides a therapeutic strategy fundamentally distinct from direct-acting therapies targeting pathogenic factors. The major advantage of this strategy is that host factors, which are not encoded in the pathogen's genome, may be far less prone to the evolution of drug resistance. Since drug resistance is increasingly widespread and compromising many standard-of-care therapies, alternative strategies to reduce or eliminate this effect would be extremely valuable.

Many intracellular pathogens (including viruses, parasites, etc.) radically alter the metabolic program of the infected cell. For example, the malaria parasites of the genus *Plasmodium*, upon invading an erythrocyte, increase the cell's glucose consumption by up to 100-fold relative to a normal erythrocyte [1]. While the plasmodial genome encodes a hexose transporter that is expressed to the parasite's plasma membrane and mediates glucose uptake into the parasite cell [2], this glucose must first enter the host cell cytoplasm in a transport process that depends primarily on the host erythrocyte glucose transporter GLUT-1 [3]. Since glucose starvation rapidly induces the death of intraerythrocytic *Plasmodium* parasites [4], and since inhibitors of the parasite hexose transporter inhibit parasite growth and viability in vitro and in vivo [5], we investigated the use of inhibitors of GLUT-1-mediated glucose uptake against the most lethal of the human malaria parasites, *Plasmodium falciparum*.

In certain embodiments of the invention, glucose uptake inhibitors are used to treat parasitic or viral infections, including, but not limited to, malaria, leishmaniasis, African trypanosomiasis, tuberculosis, HIV, HCMV and herpes virus.

Inhibitors of GLUT-1-mediated glucose uptake are extremely potent against cultured *P. falciparum*, as they rapidly induce a loss of viability of the parasite cell. This is consistent with the absolute dependence of *Plasmodium* parasites on glucose import, first into the host cell cytosol (through GLUT-1) and then into the parasite cell (through parasite hexose transporters). These data also suggest that inhibitors of other host transporters essential for glucose metabolism will provide a beneficial therapeutic effect in malaria patients.

Figure 1B:
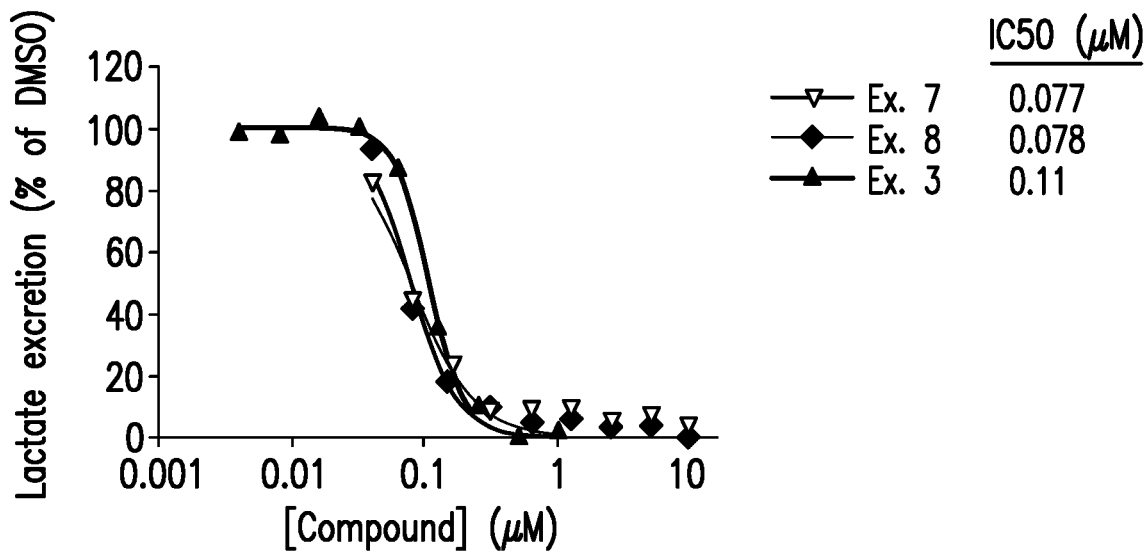
FIG. 1B shows cultures that were seeded as above and treated with varying concentrations of the indicated compounds for 48 hours. The culture medium was harvested and extracellular lactic acid was quantified by LC-MS.
Figure 2:
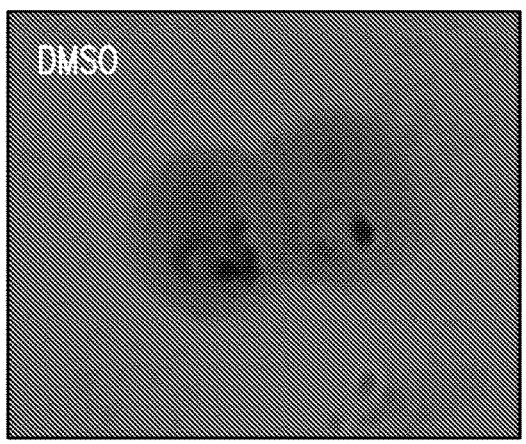
FIG. 2 shows the microscopic examination of the treated *P. falciparum*, which reveals that treated parasites condense and shrink, characteristics of parasite cell death within 6 hours of inhibitor treatment.
Figure 2:
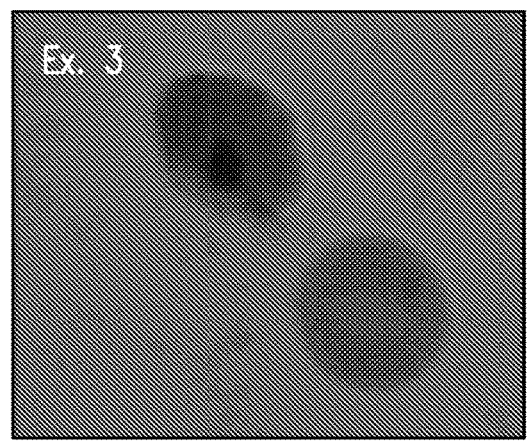
Figure 3:
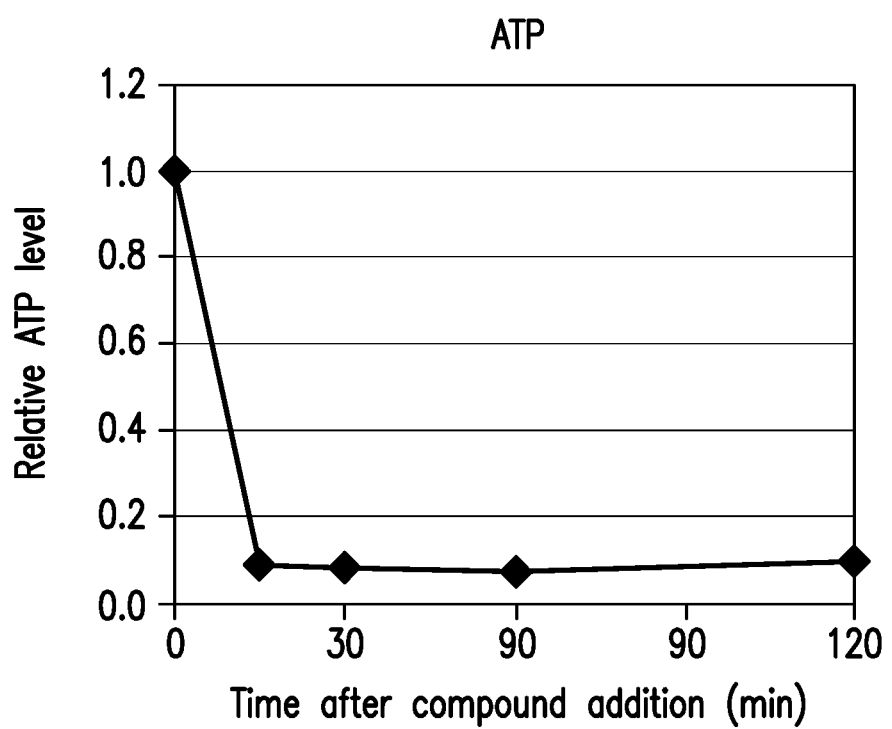
FIG. 3 shows the results of LC-MS metabolomics analysis of *P. falciparum* (3D7 strain)-infected erythrocyte cultures treated with 2.5 uM of the compound of Example 3 for varying amounts of time. The ATP levels of the infected cells are substantially depleted within 15 minutes of compound exposure and remain so for the duration of the experiment.

As previously discussed, malaria parasites rely on glucose imported by host transporters in the erythrocyte membrane (i.e. GLUT-1). At low nanomolar concentrations, the glucose uptake inhibitors display striking inhibition of both parasite proliferation (FIG. 1A) and lactate excretion (FIG. 1B), a downstream maker of glucose consumption/glycolysis. Moreover, microscopic examination of the parasites reveals that treated parasites condense and shrink, characteristics of parasite cell death, within 6 hours of inhibitor treatment (FIG. 2) and that cellular ATP levels are depleted within 15 minutes (FIG. 3).

Human Immunodeficiency Virus (HIV):

AIDS, one of the most important diseases in terms of global health burden, is caused by HIV infection of the host immune cells. Several reports indicate that a successful infection and replication cycle depends on GLUT-1-mediated glucose import [6], and GLUT-1 levels serve as a disease marker in chronically HIV-infected patients [7]. GLUT-1 inhibitors may suppress viral replication in a manner that does not elicit the drug resistance that otherwise necessitates combination therapy with multiple direct-acting antivirals.

*Mycobacterium tuberculosis:*

Tuberculosis is caused by infection with a *mycobacterium* that replicates within host macrophages. *M. tuberculosis* infection in culture induces a significant increase in GLUT-1-mediated glucose uptake, and treatment with glycolysis inhibitors such as 3-bromopyruvate induce death of both the host cell and the infecting bacterium [8]. This strongly suggests that GLUT-1 inhibitors would exert a similar suppression of infected macrophage viability.

*Leishmania donovani:*

Infection with parasites of the genus *Leishmania* causes leishmaniasis, the most severe form of which is caused by the species *Leishmania donovani*. Like *M. tuberculosis, L. donovani* infects host macrophages, and induces an increase in the levels of the GLUT-1 transporter [9]. GLUT-1 inhibition may provide a therapeutic benefit against this protozoan parasite as well.

Compounds for use in the methods of the invention include small molecules. As used herein, the terms "chemical agent" and "small molecule" are used interchangeably, and both terms refer to substances that have a molecular weight up to about 4000 atomic mass units (Daltons), preferably up to about 2000 Daltons, and more preferably up to about 1000 Daltons. Unless otherwise stated herein, the term "small molecule" as used herein refers exclusively to chemical agents, and does not refer to biological agents. As used herein, "biological agents" are molecules which include proteins, polypeptides, and nucleic acids, and have molecular weights equal to or greater than about 2000 atomic mass units (Daltons). Compounds of the invention include salts, esters, and other pharmaceutically acceptable forms of such compounds.

Compounds useful according to the present invention include those having the formula I:

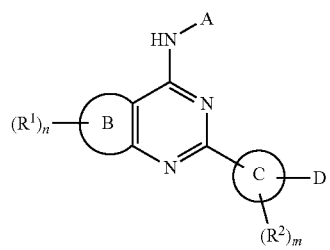

(I)

wherein:
A is selected from the group consisting of:

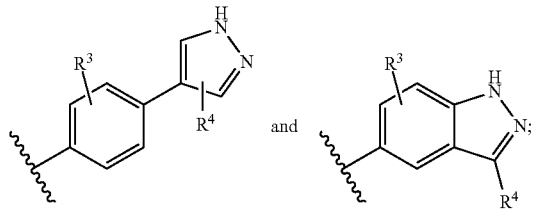

Ring B is a five- or six-membered ring containing 1 or 2 heteroatoms selected from the group consisting of N, O and S;

Ring C is a five- or six-membered aryl or heteroaryl ring containing from 0 to 2 heteroatoms selected from the group consisting of N, O and S;

each $R^1$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;

n is selected from 0, 1, or 2;

each $R^2$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;

m is selected from 0, 1, or 2;

$R^3$ is selected from the group consisting of halo, $C_1$-$C_6$ alkyl, $C_2$-$C_6$ alkenyl, $C_1$-$C_6$ alkoxy, $C_3$-$C_6$ cycloalkyl, hydroxy, amino, cyano and $C_1$-$C_3$ perfluoro alkyl;

$R^4$ is selected from the group consisting of halo, $C_1$-$C_6$ alkyl, $C_2$-$C_6$ alkenyl, $C_1$-$C_6$ alkoxy, $C_3$-$C_6$ cycloalkyl, hydroxy, amino, cyano and $C_1$-$C_3$ perfluoro alkyl; and D is selected from the group consisting of —O—$(CH_2)_y$—C(=O)$NR^5R^6$, —O—C(=O)—$(CH_2)_y$—$NR^5R^6$, —O—$(CH_2)_y$—$NR^5R^6$, —NH—C(=O)—$(CH_2)_y$—$NR^5R^6$, —NH—C(=O)—$(CH_2)_y$—R, and —NH—$(CH_2)_y$—$NR^5R^6$;

y is selected from 1, 2, or 3;

$R^5$ and $R^6$ are independently selected from the group consisting of H, $C_1$-$C_6$ alkyl, $C_2$-$C_6$ alkenyl, $C_2$-$C_6$ alkynyl, —($C_1$-$C_6$ alkyl)-O—($C_1$-$C_6$ alkyl), aryl, aralkyl, heteroaryl, and $C_3$-$C_6$ cycloalkyl, or $R^5$ and $R^6$ may be taken together with the nitrogen to which they are attached to form a 5- to 6-membered heterocyclic ring having up to 3 heteroatoms selected from N, O, and S, and which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl; and $R^7$ is selected from the group consisting of aryl, heteroaryl, and a hetercyclic group.

In certain preferred embodiments, Ring B is a five-membered ring containing 1 or 2 heteroatoms selected from the group consisting of N, O and S. In certain additional preferred embodiments, the sub-structure

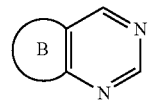

is selected from the group consisting of:

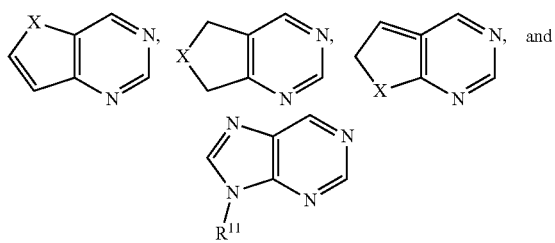

wherein X is selected from O and S, and $R^{11}$ is selected from H and $C_1$ to $C_6$ alkyl.

In certain preferred embodiments, the present invention relates to a compound having the formula II:

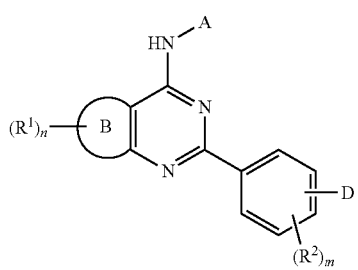

wherein:
A is selected from the group consisting of:

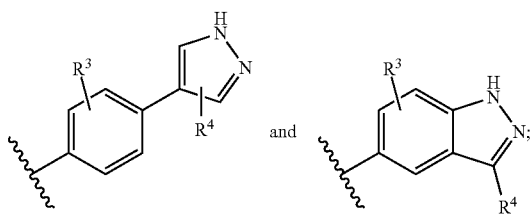

Ring B is a five- or six-membered ring containing 1 or 2 heteroatoms selected from the group consisting of N, O and S;
each $R^1$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;
n is selected from 0, 1, or 2;
each $R^2$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;
m is selected from 0, 1, or 2;
$R^3$ is selected from the group consisting of halo, $C_1$-$C_6$ alkyl, $C_2$-$C_6$ alkenyl, $C_1$-$C_6$ alkoxy, $C_3$-$C_6$ cycloalkyl, hydroxy, amino, cyano and $C_1$-$C_3$ perfluoro alkyl;
$R^4$ is selected from the group consisting of halo, $C_1$-$C_6$ alkyl, $C_2$-$C_6$ alkenyl, $C_1$-$C_6$ alkoxy, $C_3$-$C_6$ cycloalkyl, hydroxy, amino, cyano and $C_1$-$C_3$ perfluoro alkyl; and
D is selected from the group consisting of —O—$(CH_2)_y$—C(=O)$NR^5R^6$, —O—C(=O)—$(CH_2)_y$—$NR^5R^6$, —O—$(CH_2)_y$—$NR^5R^6$, —NH—C(=O)—$(CH_2)_y$—$NR^5R^6$, —NH—C(=O)—$(CH_2)_y$—R, and —NH—$(CH_2)_y$—$NR^5R^6$;
y is selected from 1, 2, or 3;
$R^5$ and $R^6$ are independently selected from the group consisting of H, $C_1$-$C_6$ alkyl, $C_2$-$C_6$ alkenyl, $C_2$-$C_6$ alkynyl, —($C_1$-$C_6$ alkyl)-O—($C_1$-$C_6$ alkyl), aryl, aralkyl, heteroaryl, and $C_3$-$C_6$ cycloalkyl,
or $R^5$ and $R^6$ may be taken together with the nitrogen to which they are attached to form a 5- to 6-membered heterocyclic ring having up to 3 heteroatoms selected from N, O, and S, and which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl; and
$R^7$ is selected from the group consisting of aryl, heteroaryl, and a hetercyclic group.

In other preferred embodiments, the present invention relates to a compound having the formula $III_a$ or $III_b$:

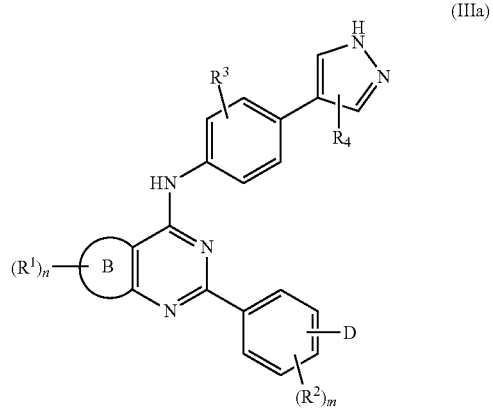

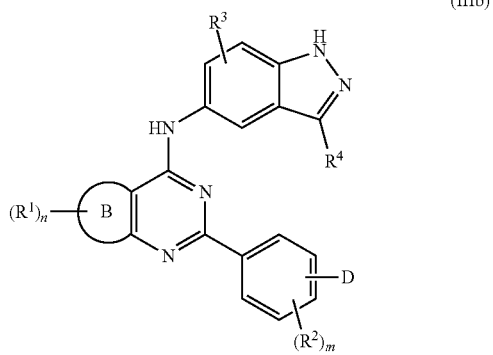

wherein:
A is selected from the group consisting of:

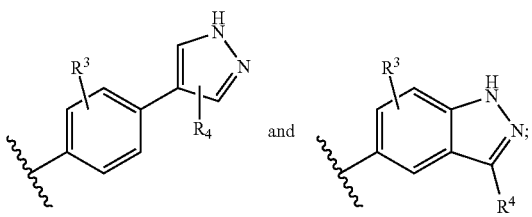

Ring B is a five- or six-membered ring containing 1 or 2 heteroatoms selected from the group consisting of N, O and S;

each $R^1$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;

n is selected from 0, 1, or 2;

each $R^2$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;

m is selected from 0, 1, or 2;

$R^3$ is selected from the group consisting of halo, $C_1$-$C_6$ alkyl, $C_2$-$C_6$ alkenyl, $C_1$-$C_6$ alkoxy, $C_3$-$C_6$ cycloalkyl, hydroxy, amino, cyano and $C_1$-$C_3$ perfluoro alkyl;

$R^4$ is selected from the group consisting of halo, $C_1$-$C_6$ alkyl, $C_2$-$C_6$ alkenyl, $C_1$-$C_6$ alkoxy, $C_3$-$C_6$ cycloalkyl, hydroxy, amino, cyano and $C_1$-$C_3$ perfluoro alkyl; and D is selected from the group consisting of —O—$(CH_2)_y$—C(=O)$NR^5R^6$, —O—C(=O)—$(CH_2)_y$—$NR^5R^6$, —O—$(CH_2)_y$—$NR^5R^6$, —NH—C(=O)—$(CH_2)_y$—$NR^5R^6$, —NH—C(=O)—$(CH_2)_y$—$R^7$, and —NH—$(CH_2)_y$—$NR^5R^6$;

y is selected from 1, 2, or 3;

$R^5$ and $R^6$ are independently selected from the group consisting of H, $C_1$-$C_6$ alkyl, $C_2$-$C_6$ alkenyl, $C_2$-$C_6$ alkynyl, —($C_1$-$C_6$ alkyl)-O—($C_1$-$C_6$ alkyl), aryl, aralkyl, heteroaryl, and $C_3$-$C_6$ cycloalkyl, or $R^5$ and $R^6$ may be taken together with the nitrogen to which they are attached to form a 5- to 6-membered heterocyclic ring having up to 3 heteroatoms selected from N, O, and S, and which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl; and $R^7$ is selected from the group consisting of aryl, heteroaryl, and a hetercyclic group.

As used herein, the definition of each expression, e.g. alkyl, m, n, R, etc., when it occurs more than once in any structure, is intended to be independent of its definition elsewhere in the same structure.

In certain embodiments, the methods of treating infectious diseases disclosed herein comprise administering a glucose uptake inhibitor disclosed in International Patent Application Publication WO 2012/040499, the contents of which are incorporated by reference herein.

The term "heteroatom" as used herein means an atom of any element other than carbon or hydrogen. Preferred heteroatoms are nitrogen, oxygen, and sulfur.

The term "alkyl" refers to the radical of saturated aliphatic groups, including straight-chain alkyl groups and branched-chain alkyl groups. In preferred embodiments, a straight chain or branched chain alkyl has 10 or fewer carbon atoms in its backbone (e.g., $C_1$-$C_{10}$ for straight chain, $C_3$-$C_{10}$ for branched chain). Likewise, preferred cycloalkyls have from 3-10 carbon atoms in their ring structure, and more preferably have 3 to 6 carbons in the ring structure.

The term "cycloalkyl" refers to saturated, carbocyclic groups having from 3 to 7 carbons in the ring. Preferred cycloalkyl groups include cyclopropyl, cyclobutyl, cyclopentyl and cyclohexyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5- and 6-membered single-ring aromatic groups that may include from zero to four heteroatoms, for example, benzene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles", "heteroaromatics" or "heteroaryl". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, aryls and/or heterocyclic groups.

The terms "heterocyclyl" or "heterocyclic group" refer to 3- to 10-membered ring structures, more preferably 5- or 6-membered rings, whose ring structures include one to four heteroatoms. Heterocycles can also be polycycles. Heterocyclic groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, aryls and/or heterocyclyls) in which two or more carbons are common to two adjoining rings, e.g., the rings are "fused rings". Rings that are joined through non-adjacent atoms are termed "bridged" rings. Each of the rings of the polycyclic group can be substituted with such substituents as described above, for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$. The term "halogen" or "halo" designates —F, —Cl, —Br or —I, and preferably —F, —Cl, or —Br. The term "hydroxyl" means —OH.

The terms "amine" and "amino" refer to both unsubstituted and substituted amines, e.g., a moiety that can be represented by the general formula:

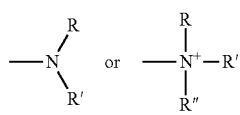

wherein R, R' and R" each independently represent H, alkyl, alkenyl, alkynyl, aralkyl, aryl, and heterocyclic groups, and most preferably H or lower alkyl.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. The term lower alkoxy refers to an alkoxy group having from 1 to 6 carbon atoms.

The term "oxo" as used herein refers to an oxygen atom that has a double bond to a another atom, particularly to carbon.

It will be understood that "substituted", "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. Illustrative substituents include, for example, those described herein above.

Additional glucose uptake inhibitors that may be used in the method of the invention for the treatment of infectious diseases include STF-31 and the compounds as disclosed in U.S. 2014/0128397; WZB-117 and the compounds as disclosed in U.S. 2012/0121536;_Fasentin; Phloretin; phlorizin and the compounds disclosed in CA 1319107; cytochalasin B; the compounds disclosed in WO 2013/182612; and the compounds disclosed in WO 2014187922, the disclosures of each are incorporated by reference in their entirety.

Certain compounds of the present invention may exist in particular geometric or stereoisomeric forms. The present invention contemplates all such compounds, including cis- and trans-isomers, R- and S-enantiomers, diastereomers, the racemic mixtures thereof, and other mixtures thereof, as falling within the scope of the invention. Additional asymmetric carbon atoms may be present in a substituent such as an alkyl group. All such isomers, as well as mixtures thereof, are included in this invention.

Certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this context, refers to the relatively non-toxic, inorganic and organic acid addition salts of compounds of the present invention. Representative salts include the hydrochloride, hydrobromide, sulfate, bisulfate, phosphate, nitrate, acetate, stearate, laurate, benzoate, lactate, phosphate, tosylate, citrate, maleate, fumarate, succinate, tartrate, napthylate, and mesylate salts and the like. (See, for example, Berge et al. "Pharmaceutical Salts", *J. Pharm. Sci*. (1977) 66:1-19).

In other cases, the compounds of the present invention may contain one or more acidic functional groups and, thus, are capable of forming pharmaceutically-acceptable salts with pharmaceutically-acceptable bases. Representative salts include alkali or alkaline earth salts such as lithium, sodium, potassium, calcium, magnesium salts and the like. Representative organic amines useful for the formation of base addition salts include ethylamine, diethylamine, ethylenediamine, ethanolamine, diethanolamine, piperazine and the like. (See, for example, Berge et al., supra).

In the methods of the invention, the glucose uptake inhibitor can be administered by routes commonly known in the art. This includes oral administration, or any other convenient route. The glucose uptake inhibitor may also be administered together with another biologically active agent. Administration can be systemic or local. Various delivery systems are known, e.g., encapsulation in liposomes, microparticles, microcapsules, capsules, and can be used to administer the compound and pharmaceutically acceptable salts thereof.

Methods of administration include but are not limited to parenteral, intradermal, intramuscular, intraperitoneal, intravenous, subcutaneous, intranasal, epidural, oral, sublingual, intranasal, intracerebral, intravaginal, transdermal, transmucosal, rectally, by inhalation, or topically, particularly to the ears, nose, eyes, or skin. The mode of administration is left to the discretion of the practitioner. In most instances, administration will result in the release of a compound into the bloodstream.

In specific embodiments, it may be desirable to administer a compound locally. This may be achieved, for example, and not by way of limitation, by local infusion, topical application, by injection, by means of a catheter, by means of a suppository, or by means of an implant, said implant being of a porous, non-porous, or gelatinous material, including membranes, such as sialastic membranes, or fibers. In such instances, administration may selectively target a local tissue without substantial release of a compound into the bloodstream.

Pulmonary administration can also be employed, e.g., by use of an inhaler or nebulizer, and formulation with an aerosolizing agent, or via perfusion in a fluorocarbon or synthetic pulmonary surfactant. In certain embodiments, a compound is formulated as a suppository, with traditional binders and vehicles such as triglycerides.

In another embodiment, a compound is delivered in a vesicle, in particular a liposome (see Langer, 1990, Science 249:1527-1533; Treat et al., in Liposomes in the Therapy of Infectious Disease and Bacterial infection, Lopez-Berestein and Fidler (eds.), Liss, New York, pp. 353-365 (1989); Lopez Berestein, ibid., pp. 317-327; see generally ibid.).

In another embodiment, a compound is delivered in a controlled release system (see, e.g., Goodson, in Medical Applications of Controlled Release, supra, vol. 2, pp. 115-138 (1984)). Examples of controlled-release systems are discussed in the review by Langer, 1990, Science 249:1527-1533 may be used. In one embodiment, a pump may be used (See Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; See also Levy et al., 1985, Science 228:190; During et al., 1989, Ann. Neurol. 25:351; Howard et al., 1989, J. Neurosurg. 71:105).

The term subject, as used herein, refers to the animal being treated, wherein the animal can be a mammal such as a human.

The therapeutically effective amount of the glucose uptake inhibitor is the dose of this compound, or of a pharmaceutically acceptable salt thereof, that provides a therapeutic benefit in the treatment or management of the infectious disease. A person skilled in the art would recognize that the therapeutically effective amount may vary depending on known factors such as the pharmacodynamic characteristics of the particular active ingredient and its mode and route of administration; age, sex, health and weight of the recipient; nature and extent of symptoms; kind of concurrent treatment, frequency of treatment and the effect desired. A person skilled in the art would also recognize that the therapeutically effective amount, or dose, of the glucose uptake inhibitor can be determined based on the disclosures herein and common knowledge in the art.

The amount of a compound, or the amount of a composition comprising a compound, that will be effective in the treatment and/or management of a tumor can be determined by standard clinical techniques. In vitro or in vivo assays may optionally be employed to help identify optimal dosage ranges.

The compound of the present invention, and its pharmaceutically acceptable salts, may be formulated in a pharmaceutical composition. In certain embodiments provided herein, the composition may comprise said compound and a pharmaceutically acceptable carrier, excipient, or diluent. The pharmaceutical compositions provided herein can be in any form that allows for the composition to be administered to a subject, including, but not limited to a human, and formulated to be compatible with an intended route of administration.

The ingredients of compositions provided herein may be supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Pharmaceutically acceptable carriers, excipients and diluents include those approved by a regulatory agency of the Federal or a state government or listed in the U.S. Pharmacopeia or other generally recognized pharmacopeia for use in animals, and more particularly in humans. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

Lactose free compositions can comprise excipients that are well known in the art and are listed, for example, in the U.S. Pharmacopeia (USP) SP (XXI)/NF (XVI). In general, lactose free compositions comprise an active ingredient, a binder/filler, and a lubricant in pharmaceutically compatible and pharmaceutically acceptable amounts. Preferred lactose free dosage forms comprise a compound, microcrystalline cellulose, pre-gelatinized starch, and magnesium stearate.

Further provided herein are anhydrous pharmaceutical compositions and dosage forms comprising one or more compounds, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, NY, N.Y., 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous compositions and dosage forms provided herein can be prepared using anhydrous or low moisture containing ingredients and low moisture or low humidity conditions. Compositions and dosage forms that comprise lactose and at least one compound that comprises a primary or secondary amine are preferably anhydrous if substantial contact with moisture and/or humidity during manufacturing, packaging, and/or storage is expected.

An anhydrous composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided herein are compositions and dosage forms that comprise one or more agents that reduce the rate by which a compound will decompose. Such agents, which are referred to herein as "stabilizers," include, but are not limited to, antioxidants such as ascorbic acid, pH buffers, or salt buffers.

The compositions and single unit dosage forms can take the form of solutions, suspensions, emulsions, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a therapeutically effective amount of a compound preferably in purified form, together with a suitable amount of carrier so as to provide the form for proper administration to the patient.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions provided herein is typically present in from about 50 to about 99 weight percent of the pharmaceutical composition or dosage form.

Suitable forms of microcrystalline cellulose include, but are not limited to, the materials sold as AVICEL® PH 101, AVICEL® PH 103 AVICEL® RC 581, AVICEL® PH 105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL® RC 581. Suitable anhydrous or low moisture excipients or additives include AVICEL® PH 103™ and Starch 1500 LM.

Disintegrants are used in the compositions provided herein to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms provided herein include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Most controlled release formulations are designed to initially release an amount of drug (active ingredient) that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or agents.

Throughout this application, various publications are referenced. These publications are hereby incorporated into this application by reference in their entireties to more fully describe the state of the art to which this invention pertains. The following examples further illustrate the invention, but should not be construed to limit the scope of the invention in any way.

The invention now being generally described, it will be more readily understood by reference to the following examples, which are included merely for the purposes of illustration of certain aspects and embodiments of the present invention, and are not intended to limit the invention.

EXAMPLES

Abbreviations used in the following examples and preparations include:
Ac$_2$O acetic anhydride
AcOH acetic acid
Bn Benzyl
Celite® diatomaceous earth
DCM dichloromethane
DIEA di-isopropylethylamine
DMAP 4-dimethylamino pyridine
DME 1,2-dimethoxyethane
DMF dimethylformamide
DMSO dimethyl sulfoxide
EDC 1-(3-dimethylaminopropyl)-3-ethylcarbodiimide hydrochloride
EtOAc ethyl acetate
EtOH ethyl alcohol or ethanol
Et$_2$O ethyl ether
Et$_3$N triethylamine
g grams
HOBt 1-hydroxybenzotriazole
HPLC high pressure liquid chromatography
h hour(s)
MeCN acetonitrile min minute(s)
MeOH methyl alcohol or methanol
mL milliliter
mmol millimoles
MS mass spectrometry
NMR nuclear magnetic resonance
iPrOH iso-propanol
PyBOP® benzotriazol-1-yl-oxytripyrrolidinophosphonium
rt room temperature
s singlet
t triplet
THF tetrahydrofuran Mass spectrometry was recorded on an LC-MS: Shimadzu 2000 LCMS. Unless stated all mass spectrometry was run in ESI mode.

$^1$H NMR spectra were recorded on a Bruker 400 or 500 MHz machine using MestReNova software.

Insofar as the synthesis of the following examples of compounds of the present invention is not explicitly described in such example, the synthesis is as described herein in general terms and the appropriate starting material can be easily selected for synthesizing the compound of the example.

Example 1

2-(3-(4-((4-(1H-pyrazol-4-yl)phenyl)amino)-6-isobutyryl-5,6,7,8-tetrahydropyrido[4,3-d]pyrimidin-2-yl)phenoxy)-N-isopropylacetamide

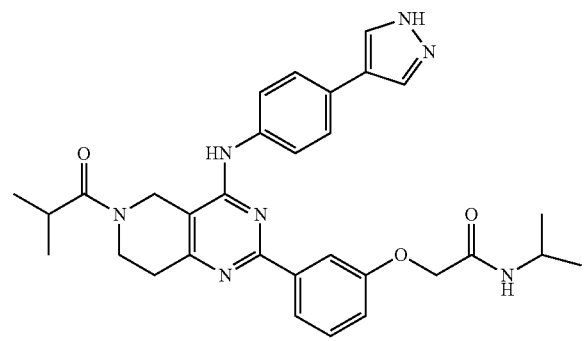 [SMILES: CC(C)NC(=O)COc1cccc(-c2nc3c(c(Nc4ccc(-c5cn[nH]c5)cc4)n2)CN(C(=O)C(C)C)CC3)c1]

Example 1A 1-(2,4-dichloro-7,8-dihydropyrido[4,3-d]pyrimidin-6(5H)-yl)-2-methylpropan-1-one

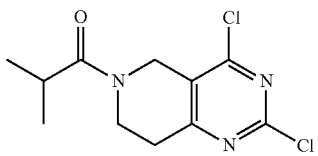 [SMILES: CC(C)C(=O)N1CCc2nc(Cl)nc(Cl)c2C1]

To the mixture of 2,4-dichloro-5,6,7,8-tetrahydropyrido[4,3-d]pyrimidine (2.20 g, 9.15 mmol, HCl salt) in CH$_2$Cl$_2$ (30.00 mL) was added dropwise TEA (2.78 g, 27.45 mmol, 3.81 mL) at 0° C. Then the mixture was stirred under N$_2$ at 0° C. for 5 min. To the mixture was added 2-methylpropanoyl chloride (1.17 g, 10.98 mmol, 1.15 mL) at 0° C. The mixture was stirred under N$_2$ at 0° C. for 2 h. LCMS showed one main peak of desired product. TLC (petroleum ether/ EtOAc=1:1, Rf=0.6) showed one new main spot. The mixture was diluted with CH$_2$Cl$_2$ (40 mL) and washed with water (40 mL×2), citric acid (10%, 40 mL×3), sat.NaHCO$_3$ (40 mL×2), brine (40 mL). The organic layer was dried over Na$_2$SO$_4$, filtered and concentrated under reduced pressure to afford the title compound (2.50 g, crude) as a light yellow solid which was used in the next step without further purification. $^1$H NMR (400 MHz, DMSO-d$_6$) δ 4.67-4.59 (m, 2H), 3.85-3.79 (m, 2H), 3.03-2.99 (m, 2H), 2.89-2.85 (m, 1H), 1.04 (d, J=6.4 Hz, 6H).

Example 1B 1-(2-chloro-4-((4-(1-(tetrahydro-2H-pyran-2-yl)-1H-pyrazol-4-yl)phenyl)amino)-7,8-dihydropyrido[4,3-d]pyrimidin-6(5H)-yl)-2-methylpropan-1-one

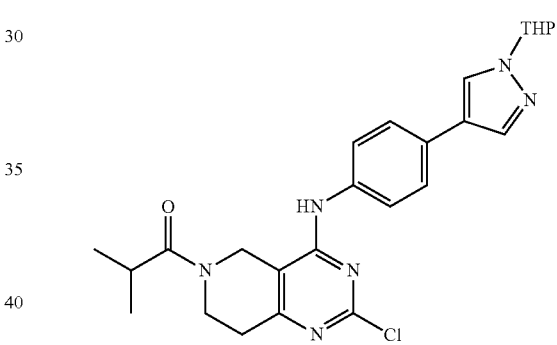

To the mixture of 1-(2,4-dichloro-7,8-dihydropyrido[4,3-d]pyrimidin-6(5H)-yl)-2-methylpropan-1-one (2.50 g, 9.12 mmol) and 4-(1-(tetrahydro-2H-pyran-2-yl)-1H-pyrazol-4-yl)aniline (2.00 g, 8.21 mmol) in n-BuOH (20.00 mL) was added DIPEA (2.36 g, 18.24 mmol, 3.19 mL). The mixture was stirred under N$_2$ at 100° C. for 16 h. LCMS showed one main peak of desired product. TLC (petroleum ether/ EtOAc=1:1, Rf=0.2) showed that one new main spot was detected. The reaction mixture was cooled to room temperature and diluted with water (30 mL). The resulting mixture was extracted with EtOAc (40 mL×3). The combined organic layers were washed with brine (50 mL), dried over Na$_2$SO$_4$, filtered and concentrated under reduced pressure to give a residue which was purified by column chromatography (SiO$_2$, petroleum ether/EtOAc=100:1 to 0:1) to give the title compound (2.8 g, 64%) as a light yellow solid. $^1$H NMR (400 MHz, DMSO-d$_6$) δ 9.06-8.93 (m, 1H), 8.32 (s, 1H), 7.94 (s, 1H), 7.63-7.55 (m, 4H), 5.41 (d, J=8.8 Hz, 1H), 4.58-4.54 (m, 2H), 3.96-3.93 (m, 1H), 3.81-3.76 (m, 2H), 3.68-3.62 (m, 1H), 3.06-3.00 (m, 1H), 2.78-2.66 (m, 2H), 2.16-2.08 (m, 1H), 1.96-1.94 (m, 2H), 1.70-1.67 (m, 2H), 1.50 (s, 2H), 1.05 (d, J=6.4 Hz, 6H).

Example 1C 2-(3-(4-((4-(1H-pyrazol-4-yl)phenyl)amino)-6-isobutyryl-5,6,7,8-tetrahydropyrido[4,3-d]pyrimidin-2-yl)phenoxy)-N-isopropylacetamide

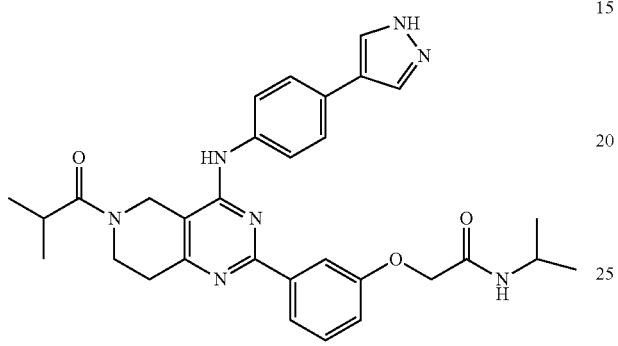

To the mixture of 1-(2-chloro-4-((4-(1-(tetrahydro-2H-pyran-2-yl)-1H-pyrazol-4-yl)phenyl)amino)-7,8-dihydropyrido[4,3-d]pyrimidin-6(5H)-yl)-2-methylpropan-1-one (1.00 eq) and N-isopropyl-2-(3-(4,4,5,5-tetramethyl-1,3,2-dioxaborolan-2-yl)phenoxy)acetamide (1.20 eq) in dioxane/H₂O (10:1) was added K₂CO₃ (2.00 eq), Pd(dppf)Cl₂ (0.10 eq). The mixture was stirred under N₂ at 90° C. for 16 h. The reaction mixture was cooled to room temperature and diluted with water. The resulting mixture was extracted with EtOAc. The combined organic layers were washed with brine, dried over Na₂SO₄, filtered and concentrated under reduced pressure to give a residue. The residue was purified by column chromatography to give 2-(3-(6-isobutyryl-4-((4-(1-(tetrahydro-2H-pyran-2-yl)-1H-pyrazol-4-yl)phenyl)amino)-5,6,7,8-tetrahydropyrido[4,3-d]pyrimidin-2-yl)phenoxy)-N-isopropylacetamide.

To the mixture of 2-(3-(6-isobutyryl-4-((4-(1-(tetrahydro-2H-pyran-2-yl)-1H-pyrazol-4-yl)phenyl)amino)-5,6,7,8-tetrahydropyrido[4,3-d]pyrimidin-2-yl)phenoxy)-N-isopropylacetamide (1.00 eq) in CH₂Cl₂ (5.00-10.00 mL) was added HCl/dioxane (4 M, 5.00-10.00 mL). The mixture was stirred at 20° C. for 1-16 h. The mixture was concentrated under reduced pressure to give a residue. The residue was purified by prep-HPLC (FA conditions) to afford the title compound.

Light yellow solid; Yield: 24% (2 steps). ¹H NMR (400 MHz, DMSO-d₆) δ 8.76-8.65 (m, 1H), 8.06-7.89 (m, 5H), 7.77 (dd, J=9.2 Hz, 8.0 Hz, 2H), 7.68-7.63 (m, 2H), 7.41-7.37 (m, 1H), 7.09-7.04 (m, 1H), 4.68-4.63 (m, 2H), 4.50 (s, 2H), 4.02-3.94 (m, 1H), 3.87-3.82 (m, 2H), 3.14-3.04 (m, 1H), 2.90-2.76 (m, 2H), 1.08 (t, J=4.4 Hz, 12H). (ES+) m/e 554.2 (M+H)⁺.

Example 2

2-(3-(4-((4-(1H-pyrazol-4-yl)phenyl)amino)-5,7-dihydrofuro[3,4-d]pyrimidin-2-yl)phenoxy)-N-isopropylacetamide

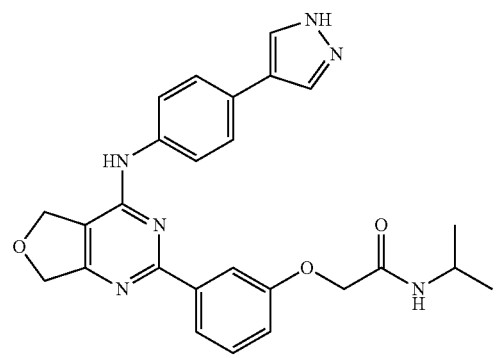 [SMILES: CC(C)NC(=O)COc1cccc(-c2nc3c(c(Nc4ccc(-c5cn[nH]c5)cc4)n2)COC3)c1]

Example 2A (Z)-3-hydroxy-2-(4-nitrophenyl)acrylaldehyde

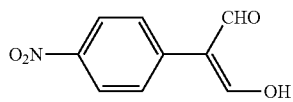

To stirring anhydrous DMF (20 mL) was added dropwise over 25 min POCl₃ (25.4 g, 165.61 mmol, 15.4 mL) at 0-10° C. After the addition was complete, it was noted that the reaction mixture was red and somewhat viscous. At this point, 4-nitrophenylacetic acid (10.0 g, 11.04 mmol) was added to the reaction and the mixture was heated to and stirred at 90° C. After about 5 min after the addition of the acid, the reaction mixture became a yellow suspension which gradually turned into a red-orange viscous liquid. After 90 min of heating, LC-MS showed one peak. At this point, the mixture was cooled to rt then placed in an ice bath and quenched dropwise with about 110 mL water that was cooled to 0° C. After the quench, the solution was basified with 1N NaOH until the pH of the solution was around 10. The mixture was then carried out directly for next step reaction. MS (ES+) m/e 194 (M+H)+.

Example 2B 4-(4-Nitrophenyl)-1H-pyrazole

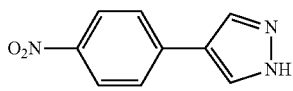 [SMILES: O=[N+]([O-])c1ccc(-c2cn[nH]c2)cc1]

To the basic solution of (Z)-3-hydroxy-2-(4-nitrophenyl)acrylaldehyde was added hydrazine (2.65 g, 82.8 mmol, 2.6 mL). The mixture was heated at 80° C. and checked by LC-MS. After 1 h, a brown precipitate was noted in the reaction vessel. LC-MS at this point showed the correct mass for the pyrazole and that the reaction was not completed yet. Heating was continued overnight then the LC-MS was checked again. The reaction was complete at this point. The reaction mixture was cooled to rt and filtered. The brown filter cake was washed with water and left on the filter to remove most of the water. Then the wet filter cake was placed on a rotovap to remove most of the water still remaining (at least 30 g) in the material. There yielded 10.3 g of the solid as the crude pyrazole. The material was then recrystallized from EtOH/ACN to give 5.96 g of dark brown crystals. The mother liquor was concentrated to remove most of the liquid. ACN was added to the mixture and the mixture was heated at 77° C. to dissolve the solid. Additional ACN was added as necessary to effect the dissolution. The solution was cooled and the resulting crystals filtered to give an additional 2.35 g of product. Total yield is 8.31 g (80%). $^1$H NMR (400 MHz, DMSO-$d_6$) δ 13.19 (b, 1H), 8.29 (s, 2H), 8.20 (d, J=8.8 Hz, 2H), 7.88 (d, J=8.8 Hz, 2H). MS (ES+) m/e 190 (M+H)+.

Example 2C 4-(1H-pyrazol-4-yl)aniline

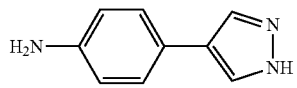

To a suspension of 4-(4-Nitrophenyl)-1H-pyrazole (8.3 g, 43.88 mmol) in MeOH/DME (2:1 v/v) was added 10% Pd/C (wet, 415 mg). The reaction flask was purged with vacuum then filled with H$_2$ from a balloon. This was done a total of 3 times. The reaction mixture was stirred at rt and checked by LC-MS for formation of the amine. After stirring for 2.5 at rt, LC-MS and tlc showed that there is a minor amount of SM in the reaction. An additional amount of catalyst (200 mg) was added to the reaction mixture and the reaction vessel was filled with H$_2$ as before. The reaction was checked after 2 h for disappearance of the remaining SM. At this time, the reaction was complete. The mixture was filtered on Celite and the Celite was washed with MeOH. The solvent was removed in vacuo to give 6.59 g (94%) of a yellow solid. $^1$H NMR (400 MHz, DMSO-$d_6$) δ 12.68 (b, 1H), 7.80 (s, 2H), 7.23 (d, J=8.0 Hz, 2H), 6.54 (d, J=8.0 Hz, 2H), 4.97 (s, 2H). MS (ES+) m/e 160 (M+H)+.

Example 2D 2-chloro-N-isopropylacetamide

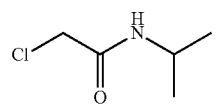

To a solution of propan-2-amine (5.9 g, 0.1 mol) in DCM (500 mL) was added 2-chloroacetyl chloride (11.1 g, 0.1 mol) drop wise at 0° C. The mixture was stirred at room temperature for 2 hrs. Then the mixture was quenched with water. The organic phase was washed with saturated brine, dried with anhydrous Na$_2$SO$_4$, filtered and concentrated in vacuum to give the product title compound (6.30 g) as a light yellow oil. $^1$H NMR (400 MHz, DMSO-$d_6$) δ 6.37 (b, 1H), 4.14-4.02 (m, 1H), 1.20 (d, J=6.8 Hz, 6H).

Example 2E 2-(3-bromophenoxy)-N-isopropylacetamide

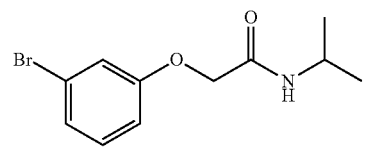

To a mixture of K$_2$CO$_3$ (13.8 g, 100 mmol) and 3-bromophenol (8.5 g, 50 mmol) in CH$_3$CN (100 mL) was stirred at room temperature for 30 min. Then 2-chloro-N-isopropylacetamide (6.3 g, 46 mmol) was added. The mixture was heated at reflux overnight. After LCMS showed the reaction was completed, the mixture was filtered and the filtrate was concentrated. The residue was dissolved in DCM and washed with NaOH solution, the organic phase was dried and concentrated to give the title compound (8.0 g) as a white solid. $^1$H NMR (400 MHz, DMSO-$d_6$) δ 7.21-7.12 (m, 3H), 6.87-6.85 (m, 1H), 6.30 (b, 1H), 4.44 (s, 2H), 4.25-4.15 (m, 1H), 1.20 (d, J=6.8 Hz, 6H).

Example 2F

N-isopropyl-2-(3-(4,4,5,5-tetramethyl-1,3,2-dioxaborolan-2-yl)phenoxy)acetamide

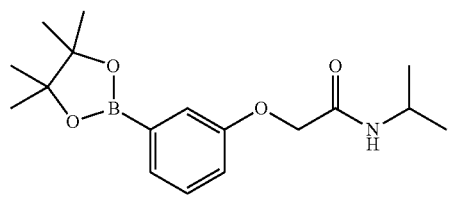 [SMILES: CC(C)NC(=O)COc1cccc(B2OC(C)(C)C(C)(C)O2)c1]

To a mixture of 2-(3-bromophenoxy)-N-isopropylacetamide (39.00 g, 143.31 mmol, 1.00 Eq), KOAc (28.13 g, 286.62 mmol) and 4,4,5,5-tetramethyl-2-(4,4,5,5-tetramethyl-1,3,2-dioxaborolan-2-yl)-1,3,2-dioxabrolane (47.31 g, 186.30 mmol) in dioxane (1 L) was added Pd(dppf)Cl$_2$ (5.32 g, 7.17 mmol) at room temperature under N$_2$. Then the reaction mixture was heated to 90° C. for 4 h. After LCMS showed the starting material was consumed completely, the mixture was filtered and the filtrate was concentrated. The residue was purified by column flash to provide the title compound (30 g) as a white solid. $^1$H NMR (400 MHz, DMSO-$d_6$) δ 7.48-7.27 (m, 3H), 7.03-7.01 (m, 1H), 6.41 (b, 1H), 4.48 (s, 2H), 4.24-4.15 (m, 1H), 1.20 (d, J=6.8 Hz, 6H). MS (ES+) m/e 320 (M+H)+.

Example 2G

N-(4-(1H-pyrazol-4-yl)phenyl)-2-chloro-5,7-dihydrofuro[3,4-d]pyrimidin-4-amine

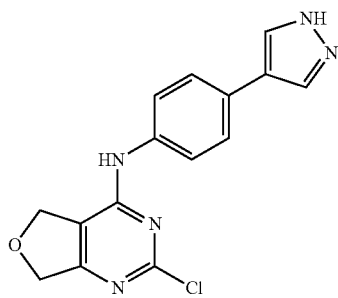 [SMILES: Clc1nc2c(c(Nc3ccc(-c4cn[nH]c4)cc3)n1)COC2]

A mixture of 2,4-dichloro-5,7-dihydrofuro[3,4-d]pyrimidine (300 mg, 1.57 mmol), 4-(1H-pyrazol-4-yl)aniline (250 mg, 1.57 mmol), and diisopropylethylamine (0.55 mL, 3.14 mmol) in DMF (3.14 mL) was heated at 100° C. for 5 h. TLC showed the reaction was complete. The mixture was then diluted with water. The resulted yellow precipitate was filtered and washed with water and dried in vacuo to provide 480 mg (97%) title compound which was used directly for next step reaction without further purification.

Example 2H 2-(3-(4-((4-(1H-pyrazol-4-yl)phenyl)amino)-5,7-dihydrofuro[3,4-d]pyrimidin-2-yl)phenoxy)-N-isopropylacetamide

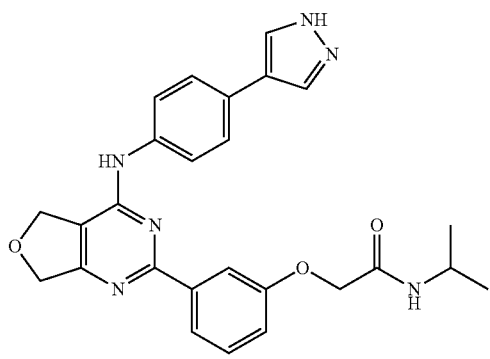 [SMILES: CC(C)NC(=O)COc1cccc(-c2nc3c(c(Nc4ccc(-c5cn[nH]c5)cc4)n2)COC3)c1]

A mixture of N-(4-(1H-pyrazol-4-yl)phenyl)-2-chloro-5,7-dihydrofuro[3,4-d]pyrimidin-4-amine (50.0 mg, 0.16 mmol), N-isopropyl-2-(3-(4,4,5,5-tetramethyl-1,3,2-dioxaborolan-2-yl)phenoxy)acetamide (50.9 mg, 0.16 mmol), Pd(PPh$_3$)$_4$ (18.4 mg, 0.02 mmol), saturated Na$_2$CO$_3$ (0.16 mL), water (0.16 mL), and dioxane (1.59 mL) was heated at 180° C. in a pressure tube for 2 h. The mixture was cooled to rt, concentrated, redissolved in DMSO and purified by reverse-phase HPLC to provide 16 mg (21%) of the title product.

$^1$H NMR (500 MHz, DMSO-d6) δ 9.30 (s, 1H), 8.07 (s, 2H), 8.03-7.92 (m, 3H), 7.81 (d, J=8.6 Hz, 2H), 7.67 (d, J=8.6 Hz, 2H), 7.44 (t, J=8.2 Hz, 1H), 7.15-7.07 (m, 1H), 5.08 (s, 2H), 4.95 (s, 2H), 4.53 (s, 2H), 3.99 (dq, J=13.3, 6.6 Hz, 1H), 1.10 (d, J=6.6 Hz, 6H). MS (ES+) m/e 471 (M+H)+.

Example 3

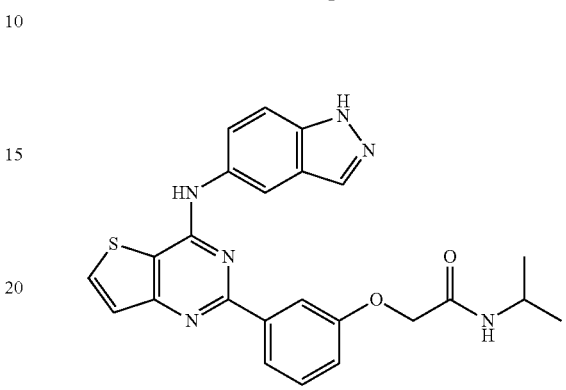

A mixture of 2-chloro-N-(1H-indazol-5-yl)thieno[3,2-d]pyrimidin-4-amine (25 mg, 0.08 mmol), N-isopropyl-2-(3-(4,4,5,5-tetramethyl-1,3,2-dioxaborolan-2-yl)phenoxy)acetamide (26.4 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product. MS (ES+) m/e 459 (M+H)+.

Example 4

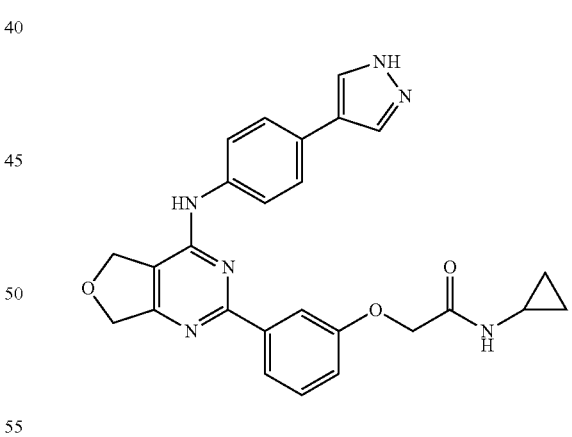

A mixture of N-(4-(1H-pyrazol-4-yl)phenyl)-2-chloro-5,7-dihydrofuro[3,4-d]pyrimidin-4-amine (25 mg, 0.08 mmol), N-cyclopropyl-2-(3-(4,4,5,5-tetramethyl-1,3,2-dioxaborolan-2-yl)phenoxy)acetamide (27.7 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (6 mg, 15%). MS (ES+) m/e 469 (M+H)+.

Example 5

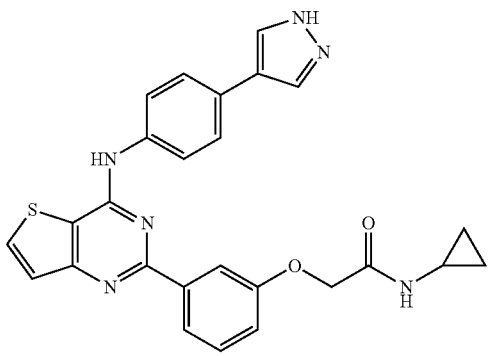 [SMILES: O=C(COc1cccc(-c2nc(Nc3ccc(-c4cn[nH]c4)cc3)c3sccc3n2)c1)NC1CC1]

A mixture of N-(4-(1H-pyrazol-4-yl)phenyl)-2-chlorothieno[3,2-d]pyrimidin-4-amine (25 mg, 0.08 mmol), N-cyclopropyl-2-(3-(4,4,5,5-tetramethyl-1,3,2-dioxaborolan-2-yl)phenoxy)acetamide (26.4 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (17 mg, 45%). MS (ES+) m/e 483 (M+H)+.

Example 6

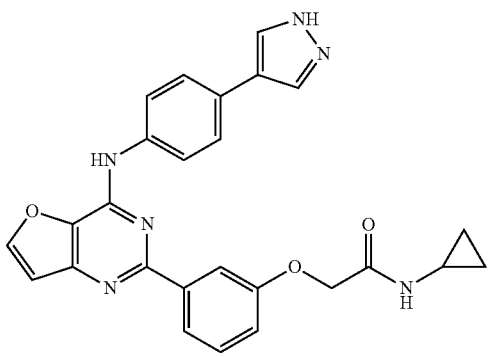 [SMILES: O=C(COc1cccc(-c2nc(Nc3ccc(-c4cn[nH]c4)cc3)c3occc3n2)c1)NC1CC1]

A mixture of N-(4-(1H-pyrazol-4-yl)phenyl)-2-chlorofuro[3,2-d]pyrimidin-4-amine (25 mg, 0.08 mmol), N-cyclopropyl-2-(3-(4,4,5,5-tetramethyl-1,3,2-dioxaborolan-2-yl)phenoxy)acetamide (27.9 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (22 mg, 55%). MS (ES+) m/e 467 (M+H)+.

Example 7

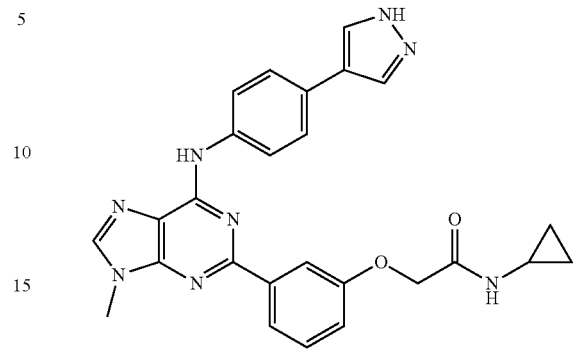

A mixture of N-(4-(1H-pyrazol-4-yl)phenyl)-2-chloro-9-methyl-9H-purin-6-amine (25 mg, 0.08 mmol), N-cyclopropyl-2-(3-(4,4,5,5-tetramethyl-1,3,2-dioxaborolan-2-yl)phenoxy)acetamide (27.9 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product. MS (ES+) m/e 481 (M+H)+.

Example 8

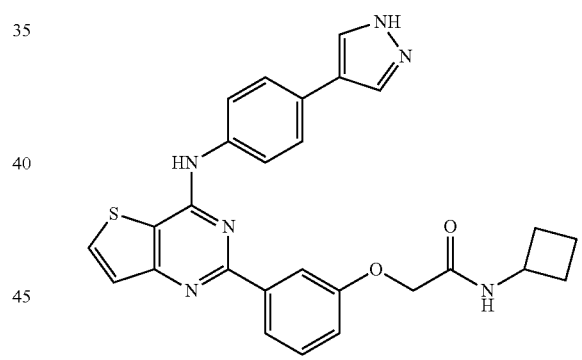

A mixture of N-(4-(1H-pyrazol-4-yl)phenyl)-2-chlorothieno[3,2-d]pyrimidin-4-amine (25 mg, 0.08 mmol), N-cyclobutyl-2-(3-(4,4,5,5-tetramethyl-1,3,2-dioxaborolan-2-yl)phenoxy)acetamide (25.2 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (16 mg, 42%). $^1$H NMR (500 MHz, DMSO-d6) δ 10.11 (s, 1H), 8.40 (d, J=8.0 Hz, 1H), 8.32 (d, J=5.4 Hz, 1H), 8.11 (s, 2H), 8.08-7.99 (m, 2H), 7.88 (d, J=8.5 Hz, 2H), 7.71 (d, J=8.6 Hz, 2H), 7.55 (d, J=5.4 Hz, 1H), 7.48 (t, J=7.9 Hz, 1H), 7.19-7.12 (m, 1H), 6.45-6.26 (m, 1H), 4.56 (s, 2H), 4.40-4.22 (m, 2H), 2.14 (m, 2H), 2.02 (m, 2H), 1.72-1.53 (m, 2H). MS (ES+) m/e 497 (M+H)+.

Example 9

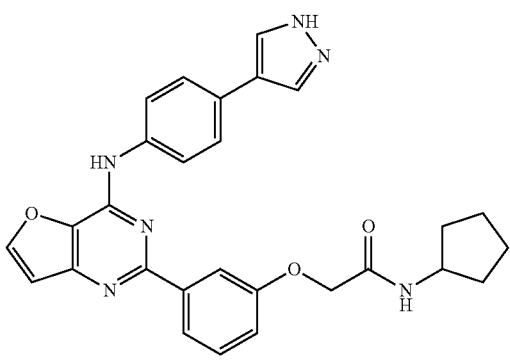 [SMILES: O=C(COc1cccc(-c2nc(Nc3ccc(-c4cn[nH]c4)cc3)c3occc3n2)c1)NC1CCCC1]

A mixture of N-(4-(1H-pyrazol-4-yl)phenyl)-2-chlorofuro[3,2-d]pyrimidin-4-amine (25 mg, 0.08 mmol), N-cyclopentyl-2-(3-(4,4,5,5-tetramethyl-1,3,2-dioxaborolan-2-yl)phenoxy)acetamide (27.7 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (12 mg, 29%). $^1$H NMR (500 MHz, DMSO-d6) δ 10.17 (s, 1H), 8.43 (s, 1H), 8.07 (d, J=9.4 Hz, 3H), 8.02-7.98 (m, 2H), 7.95 (d, J=8.6 Hz, 2H), 7.68 (d, J=8.6 Hz, 2H), 7.45 (t, J=8.1 Hz, 1H), 7.15 (d, J=2.1 Hz, 1H), 7.12-7.06 (m, 1H), 4.56 (s, 2H), 4.12 (m, 1H), 1.81 (m, 2H), 1.71-1.58 (m, 2H), 1.48 (m, 4H). MS (ES+) m/e 494 (M+H)+.

Example 10

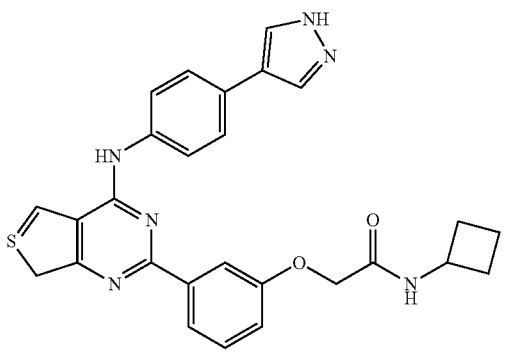

A mixture of N-(4-(1H-pyrazol-4-yl)phenyl)-2-chlorothieno[2,3-d]pyrimidin-4-amine (25 mg, 0.08 mmol), N-cyclobutyl-2-(3-(4,4,5,5-tetramethyl-1,3,2-dioxaborolan-2-yl)phenoxy)acetamide (25.3 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (9 mg, 24%). $^1$H NMR (500 MHz, DMSO-d6) δ 9.79 (s, 1H), 8.42 (d, J=8.0 Hz, 1H), 8.10 (s, 2H), 8.08-8.01 (m, 2H), 8.00-7.90 (m, 3H), 7.81-7.69 (m, 3H), 7.45 (t, J=7.9 Hz, 1H), 7.11 (dd, J=8.5, 2.3 Hz, 1H), 4.55 (s, 2H), 4.33 (m, 1H), 2.22-2.11 (m, 2H), 2.10-1.97 (m, 2H), 1.62 (m, 2H). MS (ES+) m/e 497 (M+H)+.

Example 11

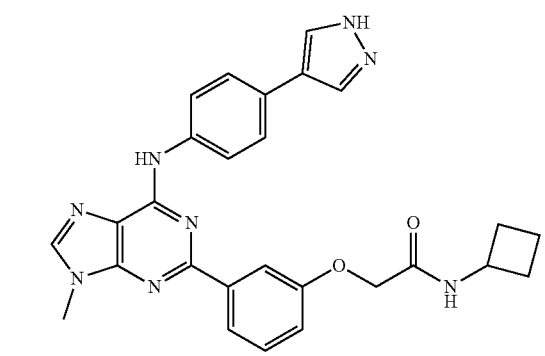 [SMILES: Cn1cnc2c(Nc3ccc(-c4cn[nH]c4)cc3)nc(-c3cccc(OCC(=O)NC4CCC4)c3)nc21]

A mixture of N-(4-(1H-pyrazol-4-yl)phenyl)-2-chloro-9-methyl-9H-purin-6-amine (25 mg, 0.08 mmol), N-cyclobutyl-2-(3-(4,4,5,5-tetramethyl-1,3,2-dioxaborolan-2-yl)phenoxy)acetamide (25.4 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (19 mg, 50%). $^1$H NMR (500 MHz, DMSO-d6) δ 9.98 (s, 1H), 8.41 (d, J=8.0 Hz, 1H), 8.35 (s, 1H), 8.07 (s, 6H), 7.66 (d, J=8.7 Hz, 2H), 7.46 (t, J=8.1 Hz, 1H), 7.09 (dd, J=7.8, 2.1 Hz, 1H), 4.57 (s, 2H), 4.33 (m, 2H), 2.22-2.10 (m, 2H), 2.09-1.95 (m, 2H), 1.62 (m, 2H). MS (ES+) m/e 495 (M+H)+.

Example 12

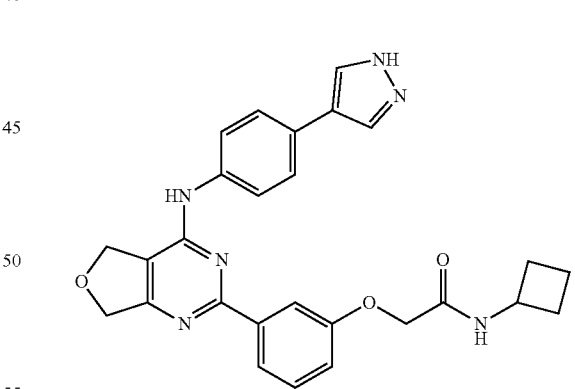

A mixture of N-(4-(1H-pyrazol-4-yl)phenyl)-2-chloro-5,7-dihydrofuro[3,4-d]pyrimidin-4-amine (25 mg, 0.08 mmol), N-cyclobutyl-2-(3-(4,4,5,5-tetramethyl-1,3,2-dioxaborolan-2-yl)phenoxy)acetamide (26.4 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (6 mg, 16%). $^1$H NMR (500 MHz, DMSO-d6) δ 9.30 (s, 1H), 8.40 (d, J=7.9 Hz, 1H), 8.08 (s, 2H), 7.97 (d, J=7.9 Hz, 2H), 7.82 (m, 2H), 7.67 (d, J=8.5 Hz, 2H), 7.44 (t, J=7.9 Hz, 1H), 7.11 (d, J=7.8 Hz, 1H), 5.09 (s, 2H), 4.96 (s, 2H), 4.53 (s, 2H), 4.32 (m, 1H), 2.14 (m, 2H), 2.03 (m, 2H), 1.62 (m, 2H). MS (ES+) m/e 483 (M+H)+.

Example 13

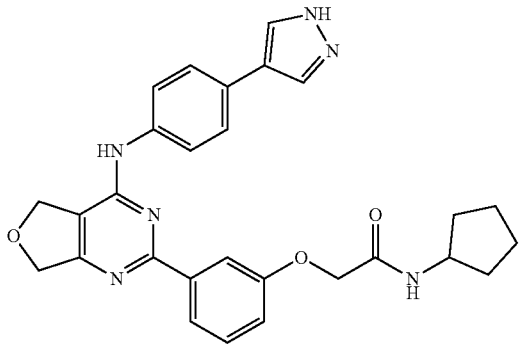 [SMILES: O=C(COc1cccc(-c2nc3c(c(Nc4ccc(-c5cn[nH]c5)cc4)n2)COC3)c1)NC1CCCC1]

A mixture of N-(4-(1H-pyrazol-4-yl)phenyl)-2-chloro-5,7-dihydrofuro[3,4-d]pyrimidin-4-amine (25 mg, 0.08 mmol), N-cyclopentyl-2-(3-(4,4,5,5-tetramethyl-1,3,2-dioxaborolan-2-yl)phenoxy)acetamide (26.4 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product. $^1$H NMR (500 MHz, DMSO-d6) δ 9.28 (s, 1H), 8.07 (s, 3H), 7.96 (d, J=6.7 Hz, 2H), 7.82 (d, J=8.4 Hz, 2H), 7.67 (d, J=8.5 Hz, 2H), 7.44 (t, J=8.1 Hz, 1H), 7.10 (d, J=8.3 Hz, 1H), 6.36 (dd, J=15.5, 7.1 Hz, 1H), 5.09 (s, 2H), 4.95 (s, 2H), 4.54 (s, 3H), 4.11 (m, 1H), 1.80 (m, 2H), 1.64 (m, 2H), 1.54-1.37 (m, 4H). MS (ES+) m/e 497 (M+H)+.

Example 14

2-(3-(4-((4-(1H-pyrazol-4-yl)phenyl)amino)pyrido[3,2-d]pyrimidin-2-yl)phenoxy)-N-isobutylacetamide

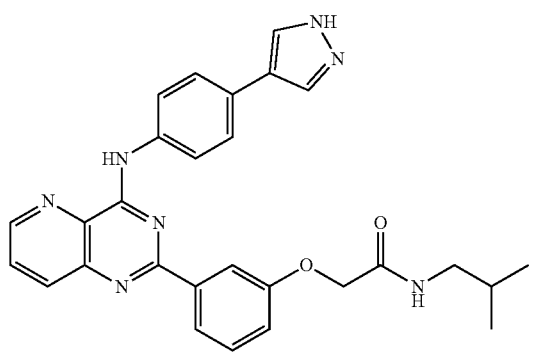 [SMILES: CC(C)CNC(=O)COc1cccc(-c2nc(Nc3ccc(-c4cn[nH]c4)cc3)c3ncccc3n2)c1]

A mixture of N-(4-(1H-pyrazol-4-yl)phenyl)-2-chloropyrido[3,2-d]pyrimidin-4-amine (25 mg, 0.08 mmol), N-isobutyl-2-(3-(4,4,5,5-tetramethyl-1,3,2-dioxaborolan-2-yl)phenoxy)acetamide (26 mg, 0.08 mmol), tetrakis(triphenylphosphine)palladium(0) (9 mg, 0.01 mmol), dioxane (0.77 mL), water (0.08 mL), and saturated Na$_2$CO$_3$ (0.08 mL) was heated in microwave at 180° C. for 2 h. The mixture was concentrated in vacuo to remove the volatiles. The residue was dissolved in DMSO and purified by reverse-phase HPLC to provide the title compound (25 mg, 65%). $^1$H NMR (400 MHz, DMSO-d$_6$) δ 10.62 (s, 1H), 8.95 (dd, J=4.2, 1.5 Hz, 1H), 8.31 (dd, J=8.4, 1.5 Hz, 1H), 8.22-8.06 (m, 8H), 7.98 (dd, J=8.5, 4.2 Hz, 1H), 7.76-7.70 (m, 2H), 7.52 (t, J=7.9 Hz, 1H), 7.25-7.13 (m, 1H), 4.64 (s, 2H), 2.98 (t, J=6.5 Hz, 2H), 1.75 (dt, J=13.6, 6.8 Hz, 1H), 0.82 (d, J=6.7 Hz, 6H). MS (ES+) m/e 494 (M+H)$^+$.

Example 15

2-(3-(4-((4-(1H-pyrazol-4-yl)phenyl)amino)-1-methyl-1H-pyrazolo[3,4-d]pyrimidin-6-yl)phenoxy)-N-cyclobutylacetamide

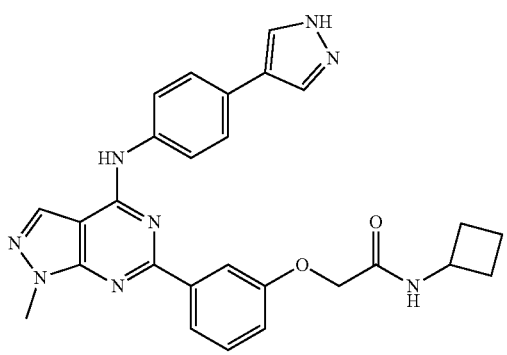 [SMILES: Cn1ncc2c(Nc3ccc(-c4cn[nH]c4)cc3)nc(-c3cccc(OCC(=O)NC4CCC4)c3)nc21]

Example 15A

N-(4-(1H-pyrazol-4-yl)phenyl)-6-chloro-1-methyl-1H-pyrazolo[3,4-d]pyrimidin-4-amine

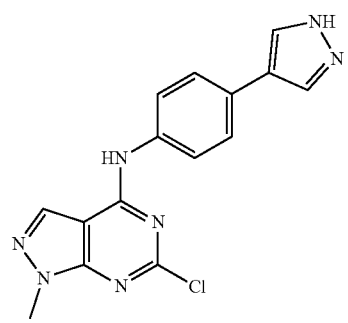 [SMILES: Cn1ncc2c(Nc3ccc(-c4cn[nH]c4)cc3)nc(Cl)nc21]

A mixture of 4,6-dichloro-1-methyl-1H-pyrazolo[3,4-d]pyrimidine (300 mg, 1.50 mmol), 4-(1H-pyrazol-4-yl)aniline (235, 1.50 mmol), and iPr2NEt (0.52 mL, 0.74 mmol) in DMF (3.0 mL) was heated at 100 C for 5 h, cooled to rt, and diluted with water. The precipitate formed was collected by filtration and washed with water and dried in vacuo to provide the title compound (470 mg, 98%). $^1$H NMR (400 MHz, DMSO-d$_6$) δ 12.95 (s, 1H), 10.48 (s, 1H), 8.26 (d, J=61.6 Hz, 2H), 7.95 (s, 1H), 7.84-7.51 (m, 4H), 3.91 (s, 3H). MS (ES+) m/e 326 (M+H)$^+$.

Example 15B 2-(3-(4-((4-(1H-pyrazol-4-yl)phenyl)amino)-1-methyl-1H-pyrazolo[3,4-d]pyrimidin-6-yl)phenoxy)-N-cyclobutylacetamide

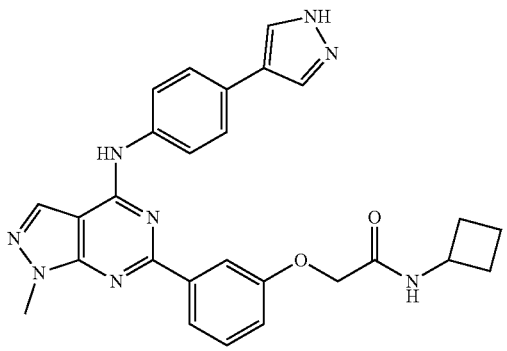 [SMILES: Cn1ncc2c(Nc3ccc(-c4cn[nH]c4)cc3)nc(-c3cccc(OCC(=O)NC4CCC4)c3)nc21]

A mixture of N-(4-(1H-pyrazol-4-yl)phenyl)-6-chloro-1-methyl-1H-pyrazolo[3,4-d]pyrimidin-4-amine (25 mg, 0.08 mmol), N-cyclobutyl-2-(3-(4,4,5,5-tetramethyl-1,3,2-dioxaborolan-2-yl)phenoxy)acetamide (24 mg, 0.08 mmol), tetrakis(triphenylphosphine)palladium(0) (9 mg, 0.01 mmol), dioxane (0.77 mL), water (0.08 mL), and saturated Na2CO3 (0.08 mL) was heated in microwave at 180° C. for 2 h. The mixture was concentrated in vacuo to remove the volatiles. The residue was dissolved in DMSO and purified by reverse-phase HPLC to provide the title compound (26 mg, 69%). $^1$H NMR (400 MHz, DMSO-$d_6$) δ 10.18 (s, 1H), 8.41 (d, J=8.0 Hz, 1H), 8.12-8.09 (m, 2H), 7.95 (d, J=7.9 Hz, 2H), 7.76-7.69 (m, 2H), 7.68-7.53 (m, 4H), 7.49-7.44 (m, 1H), 7.13 (ddd, J=8.1, 2.6, 1.1 Hz, 1H), 4.57 (s, 2H), 4.33 (q, J=8.2 Hz, 1H), 4.04 (s, 3H), 2.19-2.10 (m, 2H), 2.08-1.96 (m, 2H), 1.70-1.55 (m, 2H). MS (ES+) m/e 495 (M+H)$^+$.

Example 16

2-(3-(4-((4-(1H-pyrazol-4-yl)phenyl)amino)-1-methyl-1H-pyrazolo[3,4-d]pyrimidin-6-yl)phenoxy)-N-isopropylacetamide

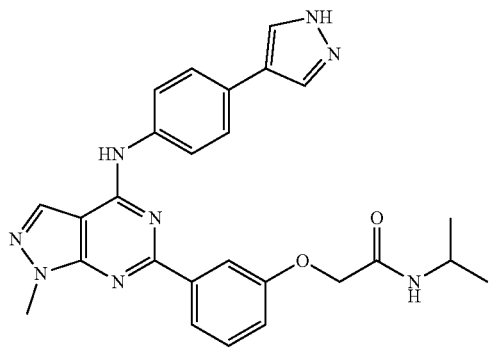 [SMILES: CC(C)NC(=O)COc1cccc(-c2nc(Nc3ccc(-c4cn[nH]c4)cc3)c3cnn(C)c3n2)c1]

A mixture of N-(4-(1H-pyrazol-4-yl)phenyl)-6-chloro-1-methyl-1H-pyrazolo[3,4-d]pyrimidin-4-amine (25 mg, 0.08 mmol), N-isopropyl-2-(3-(4,4,5,5-tetramethyl-1,3,2-dioxaborolan-2-yl)phenoxy)acetamide (24 mg, 0.08 mmol), tetrakis(triphenylphosphine)palladium(0) (9 mg, 0.01 mmol), dioxane (0.77 mL), water (0.08 mL), and saturated Na$_2$CO$_3$ (0.08 mL) was heated in microwave at 180° C. for 2 h. The mixture was concentrated in vacuo to remove the volatiles. The residue was dissolved in DMSO and purified by reverse-phase HPLC to provide the title compound (16 mg, 74%). $^1$H NMR (400 MHz, DMSO-$d_6$) δ 10.17 (s, 1H), 8.30 (s, 1H), 8.14-8.06 (m, 4H), 8.02-7.94 (m, 3H), 7.76-7.66 (m, 2H), 7.47 (t, J=8.0 Hz, 1H), 7.20-7.08 (m, 1H), 4.57 (s, 2H), 4.10-3.95 (m, 4H), 1.11 (d, J=6.6 Hz, 6H). MS(ES+) m/e 483 (M+H)$^+$.

Example 17

2-(3-(4-((4-(1H-pyrazol-4-yl)phenyl)amino)-1-methyl-1H-pyrazolo[3,4-d]pyrimidin-6-yl)phenoxy)-N-cyclopentylacetamide

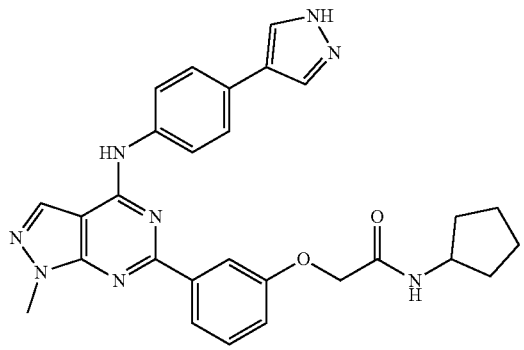 [SMILES: Cn1ncc2c(Nc3ccc(-c4cn[nH]c4)cc3)nc(-c3cccc(OCC(=O)NC4CCCC4)c3)nc21]

A mixture of N-(4-(1H-pyrazol-4-yl)phenyl)-6-chloro-1-methyl-1H-pyrazolo[3,4-d]pyrimidin-4-amine (25 mg, 0.08 mmol), N-cyclopentyl-2-(3-(4,4,5,5-tetramethyl-1,3,2-dioxaborolan-2-yl)phenoxy)acetamide (26 mg, 0.08 mmol), tetrakis(triphenylphosphine)palladium(0) (9 mg, 0.01 mmol), dioxane (0.77 mL), water (0.08 mL), and saturated Na$_2$CO$_3$ (0.08 mL) was heated in microwave at 180° C. for 2 h. The mixture was concentrated in vacuo to remove the volatiles. The residue was dissolved in DMSO and purified by reverse-phase HPLC to provide the title compound (21 mg, 54%). $^1$H NMR (500 MHz, DMSO-$d_6$) δ 10.17 (s, 1H), 8.31 (b, 1H), 8.10 (d, J=9.2 Hz, 4H), 7.95 (d, J=8.0 Hz, 2H), 7.72 (d, J=8.3 Hz, 2H), 7.46 (t, J=7.6 Hz, 1H), 7.30 (t, J=7.8 Hz, 1H), 7.17-7.07 (m, 1H), 7.01-6.90 (m, 1H), 4.58 (s, 2H), 4.44 (s, 1H), 4.19-3.96 (m, 4H), 1.89-1.33 (m, 8H). MS(ES+) m/e 509 (M+H)$^+$.

Example 18

2-(3-(4-((4-(1H-pyrazol-4-yl)phenyl)amino)-1-methyl-1H-pyrazolo[3,4-d]pyrimidin-6-yl)phenoxy)-N-isobutylacetamide

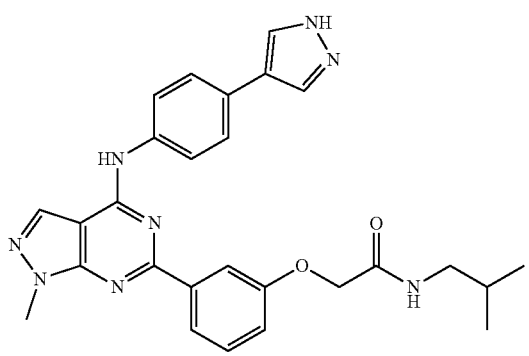 [SMILES: CC(C)CNC(=O)COc1cccc(-c2nc(Nc3ccc(-c4cn[nH]c4)cc3)c3cnn(C)c3n2)c1]

A mixture of N-(4-(1H-pyrazol-4-yl)phenyl)-6-chloro-1-methyl-1H-pyrazolo[3,4-d]pyrimidin-4-amine (25 mg, 0.08 mmol), N-isobutyl-2-(3-(4,4,5,5-tetramethyl-1,3,2-dioxaborolan-2-yl)phenoxy)acetamide (25 mg, 0.08 mmol), tetrakis(triphenylphosphine)palladium(0) (9 mg, 0.01 mmol), dioxane (0.77 mL), water (0.08 mL), and saturated Na$_2$CO$_3$ (0.08 mL) was heated in microwave at 180° C. for 2 h. The mixture was concentrated in vacuo to remove the volatiles. The residue was dissolved in DMSO and purified by reverse-phase HPLC to provide the title compound (19 mg, 50%). $^1$H NMR (500 MHz, DMSO-d$_6$) δ 10.18 (s, 1H), 8.31 (s, 1H), 8.17 (t, J=6.0 Hz, 1H), 8.10 (dd, J=7.7, 5.8 Hz, 4H), 7.95 (d, J=8.1 Hz, 2H), 7.76-7.69 (m, 2H), 7.47 (t, J=8.0 Hz, 1H), 7.16-7.10 (m, 1H), 4.62 (s, 2H), 3.00-2.94 (m, 3H), 1.75 (dh, J=13.3, 6.7 Hz, 1H), 0.81 (d, J=6.6 Hz, 6H). MS(ES+) m/e 497 (M+H)$^+$.

Example 19

2-(3-(4-((4-(1H-pyrazol-4-yl)phenyl)amino)pyrido[3,4-d]pyrimidin-2-yl)phenoxy)-N-isopropylacetamide

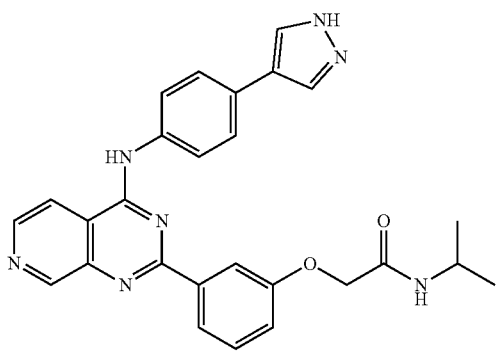 [SMILES: CC(C)NC(=O)COc1cccc(-c2nc(Nc3ccc(-c4cn[nH]c4)cc3)c3ccncc3n2)c1]

Example 19A

N-(4-(1H-pyrazol-4-yl)phenyl)-2-chloropyrido[3,4-d]pyrimidin-4-amine

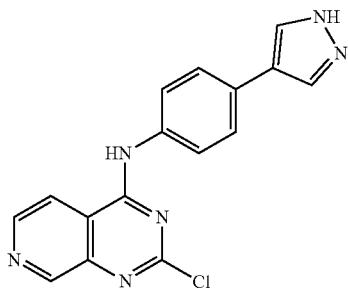 [SMILES: Clc1nc(Nc2ccc(-c3cn[nH]c3)cc2)c2ccncc2n1]

A mixture of 2,4-dichloropyrido[3,4-d]pyrimidine (250 mg, 1.25 mmol), 4-(1H-pyrazol-4-yl)aniline (199, 1.25 mmol), and iPr$_2$NEt (0.44 mL, 2.50 mmol) in DMF (2.5 mL) was heated at 100 C for 5 h, cooled to rt, and diluted with water. The precipitate formed was collected by filtration and washed with water and dried in vacuo to provide the title compound (400 mg, 99%). MS 19S+) m/e 323 (M+H)$^+$.

Example 19B 2-(3-(4-((4-(1H-pyrazol-4-yl)phenyl)amino)pyrido[3,4-d]pyrimidin-2-yl)phenoxy)-N-isopropylacetamide

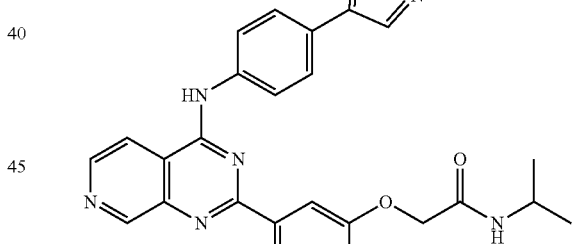

A mixture of N-(4-(1H-pyrazol-4-yl)phenyl)-2-chloropyrido[3,4-d]pyrimidin-4-amine (25 mg, 0.08 mmol), N-isopropyl-2-(3-(4,4,5,5-tetramethyl-1,3,2-dioxaborolan-2-yl)phenoxy)acetamide (26 mg, 0.08 mmol), tetrakis(triphenylphosphine)palladium(0) (9 mg, 0.01 mmol), dioxane (0.77 mL), water (0.08 mL), and saturated Na$_2$CO$_3$ (0.08 mL) was heated in microwave at 180° C. for 2 h. The mixture was concentrated in vacuo to remove the volatiles. The residue was dissolved in DMSO and purified by reverse-phase HPLC to provide the title compound (10 mg, 27%). $^1$H NMR (400 MHz, DMSO-d$_6$) δ 10.28 (s, 1H), 9.26 (s, 1H), 8.73 (d, J=5.6 Hz, 1H), 8.51 (d, J=5.7 Hz, 1H), 8.21-8.06 (m, 4H), 8.00 (dd, J=10.9, 8.2 Hz, 3H), 7.82-7.73 (m, 2H), 7.49 (t, J=8.1 Hz, 1H), 7.16 (dd, J=8.2, 2.5 Hz, 1H), 4.57 (s, 2H), 4.09-3.94 (m, 1H), 1.11 (d, J=6.6 Hz, 6H). MS(ES+) m/e 480 (M+H)$^+$.

Example 20

2-(3-(4-((4-(1H-pyrazol-4-yl)phenyl)amino)pyrido[3,4-d]pyrimidin-2-yl)phenoxy)-N-cyclobutylacetamide

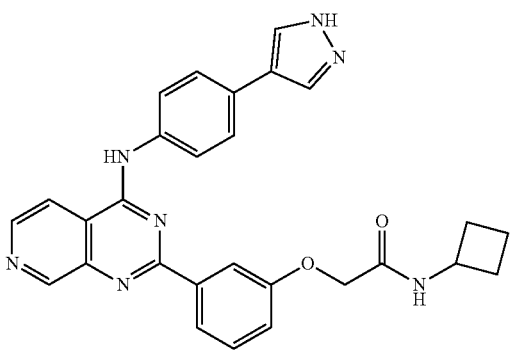 [SMILES: O=C(COc1cccc(-c2nc(Nc3ccc(-c4cn[nH]c4)cc3)c3ccncc3n2)c1)NC1CCC1]

A mixture of N-(4-(1H-pyrazol-4-yl)phenyl)-2-chloropyrido[3,4-d]pyrimidin-4-amine (25 mg, 0.08 mmol), N-cyclobutyl-2-(3-(4,4,5,5-tetramethyl-1,3,2-dioxaborolan-2-yl)phenoxy)acetamide (26 mg, 0.08 mmol), tetrakis(triphenylphosphine)palladium(0) (9 mg, 0.01 mmol), dioxane (0.77 mL), water (0.08 mL), and saturated Na$_2$CO$_3$ (0.08 mL) was heated in microwave at 180° C. for 2 h. The mixture was concentrated in vacuo to remove the volatiles. The residue was dissolved in DMSO and purified by reverse-phase HPLC to provide the title compound (11 mg, 29%). $^1$H NMR (400 MHz, DMSO-d$_6$) δ 10.28 (s, 1H), 9.26 (s, 1H), 8.73 (d, J=5.6 Hz, 1H), 8.51 (d, J=5.7 Hz, 1H), 8.43 (d, J=8.0 Hz, 1H), 8.13 (s, 2H), 8.11-8.07 (m, 2H), 7.99 (d, J=8.3 Hz, 2H), 7.77 (d, J=8.3 Hz, 2H), 7.49 (t, J=8.0 Hz, 1H), 7.19-7.13 (m, 1H), 7.06 (t, J=8.1 Hz, 1H), 6.41-6.31 (m, 2H), 4.57 (s, 2H), 4.36-4.22 (m, 2H), 2.18-1.96 (m, 4H), 1.68-1.55 (m, 2H). MS (ES+) m/e 492 (M+H)$^+$.

Example 21

2-(3-(4-((4-(1H-pyrazol-4-yl)phenyl)amino)pyrido[3,4-d]pyrimidin-2-yl)phenoxy)-N-cyclopentylacetamide

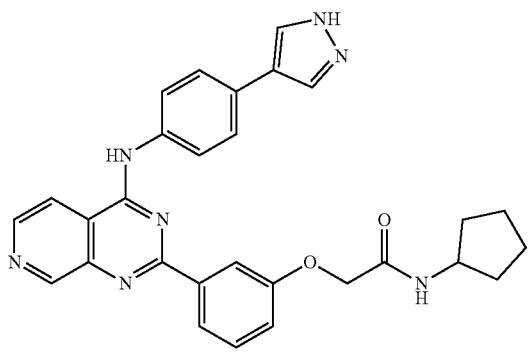 [SMILES: O=C(COc1cccc(-c2nc(Nc3ccc(-c4cn[nH]c4)cc3)c3ccncc3n2)c1)NC1CCCC1]

A mixture of N-(4-(1H-pyrazol-4-yl)phenyl)-2-chloropyrido[3,4-d]pyrimidin-4-amine (25 mg, 0.08 mmol), N-cyclopentyl-2-(3-(4,4,5,5-tetramethyl-1,3,2-dioxaborolan-2-yl)phenoxy)acetamide (26 mg, 0.08 mmol), tetrakis(triphenylphosphine)palladium(0) (9 mg, 0.01 mmol), dioxane (0.77 mL), water (0.08 mL), and saturated Na$_2$CO$_3$ (0.08 mL) was heated in microwave at 180° C. for 2 h. The mixture was concentrated in vacuo to remove the volatiles. The residue was dissolved in DMSO and purified by reverse-phase HPLC to provide the title compound (11 mg, 29%). $^1$H NMR (400 MHz, DMSO-d$_6$) δ 10.28 (s, 1H), 9.26 (s, 1H), 8.73 (d, J=5.6 Hz, 1H), 8.51 (d, J=5.7 Hz, 1H), 8.18-8.06 (m, 5H), 8.03-7.96 (m, 2H), 7.81-7.74 (m, 2H), 7.48 (t, J=8.0 Hz, 1H), 7.19-7.10 (m, 1H), 4.58 (s, 2H), 4.13 (h, J=7.2 Hz, 1H), 1.86-1.78 (m, 2H), 1.65 (ddt, J=8.5, 6.2, 2.8 Hz, 2H), 1.55-1.42 (m, 4H). MS (ES+) m/e 506 (M+H)$^+$.

Example 22

2-(3-(7-((4-(1H-pyrazol-4-yl)phenyl)amino)thiazolo[5,4-d]pyrimidin-5-yl)phenoxy)-N-isopropylacetamide

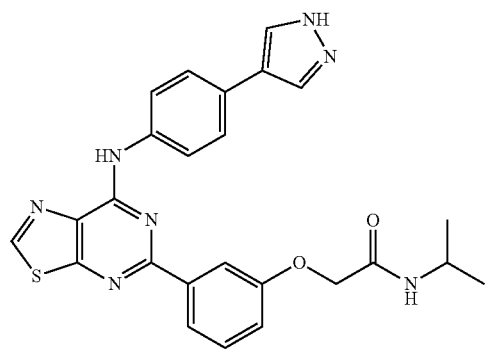 [SMILES: CC(C)NC(=O)COc1cccc(-c2nc(Nc3ccc(-c4cn[nH]c4)cc3)c3ncsc3n2)c1]

Example 22A

N-(4-(1H-pyrazol-4-yl)phenyl)-5-chlorothiazolo[5,4-d]pyrimidin-7-amine

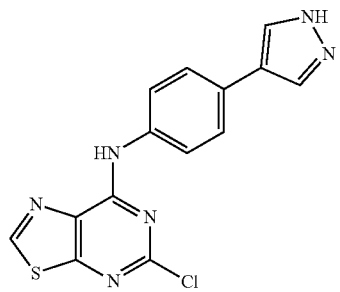 [SMILES: Clc1nc(Nc2ccc(-c3cn[nH]c3)cc2)c2ncsc2n1]

A mixture of 5,7-dichlorothiazolo[5,4-d]pyrimidine (300 mg, 1.46 mmol), 4-(1H-pyrazol-4-yl)aniline (233, 1.46 mmol), and iPr$_2$NEt (0.51 mL, 2.93 mmol) in DMF (2.9 mL) was heated at 100° C. for 5 h, cooled to rt, and diluted with water. The precipitate formed was collected by filtration and washed with water and dried in vacuo to provide the title compound (470 mg, 98%). MS (ES+) m/e 329 (M+H)$^+$.

Example 22B 2-(3-(7-((4-(1H-pyrazol-4-yl)phenyl)amino)thiazolo[5,4-d]pyrimidin-5-yl)phenoxy)-N-isopropylacetamide

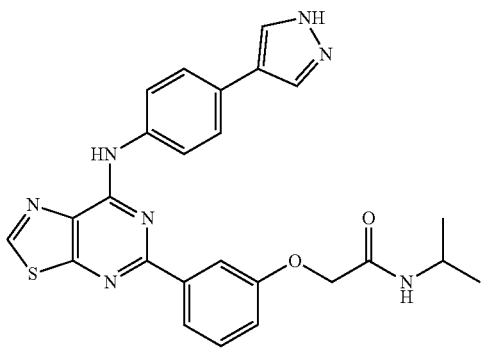 [SMILES: CC(C)NC(=O)COc1cccc(-c2nc(Nc3ccc(-c4cn[nH]c4)cc3)c3ncsc3n2)c1]

A mixture of N-(4-(1H-pyrazol-4-yl)phenyl)-5-chlorothiazolo[5,4-d]pyrimidin-7-amine (25 mg, 0.08 mmol), N-isopropyl-2-(3-(4,4,5,5-tetramethyl-1,3,2-dioxaborolan-2-yl)phenoxy)acetamide (24 mg, 0.08 mmol), tetrakis(triphenylphosphine)palladium(0) (9 mg, 0.01 mmol), dioxane (0.77 mL), water (0.08 mL), and saturated $Na_2CO_3$ (0.08 mL) was heated in microwave at 180° C. for 2 h. The mixture was concentrated in vacuo to remove the volatiles. The residue was dissolved in DMSO and purified by reverse-phase HPLC to provide the title compound (7 mg, 19%). $^1$H NMR (400 MHz, DMSO-$d_6$) δ 10.31 (s, 1H), 9.40 (s, 1H), 8.16-7.95 (m, 6H), 7.69 (d, J=8.3 Hz, 2H), 7.66-7.51 (m, 2H), 7.46 (t, J=8.0 Hz, 1H), 7.16-7.06 (m, 1H), 4.56 (s, 2H), 4.03-3.97 (m, 2H), 1.11 (d, J=6.6 Hz, 6H). MS (ES+) m/e 486 (M+H)$^+$.

Example 23

2-(3-(7-((4-(1H-pyrazol-4-yl)phenyl)amino)thiazolo[5,4-d]pyrimidin-5-yl)phenoxy)-N-cyclobutylacetamide

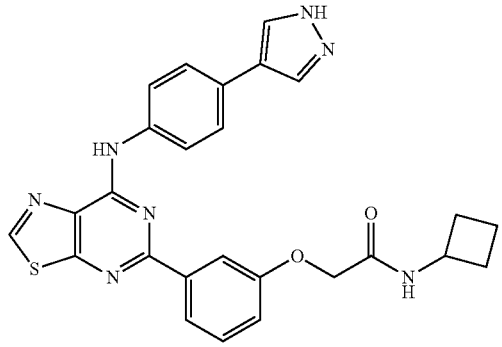 [SMILES: O=C(COc1cccc(-c2nc(Nc3ccc(-c4cn[nH]c4)cc3)c3ncsc3n2)c1)NC1CCC1]

A mixture of N-(4-(1H-pyrazol-4-yl)phenyl)-5-chlorothiazolo[5,4-d]pyrimidin-7-amine (25 mg, 0.08 mmol), N-cyclobutyl-2-(3-(4,4,5,5-tetramethyl-1,3,2-dioxaborolan-2-yl)phenoxy)acetamide (24 mg, 0.08 mmol), tetrakis(triphenylphosphine)palladium(0) (9 mg, 0.01 mmol), dioxane (0.77 mL), water (0.08 mL), and saturated $Na_2CO_3$ (0.08 mL) was heated in microwave at 180° C. for 2 h. The mixture was concentrated in vacuo to remove the volatiles. The residue was dissolved in DMSO and purified by reverse-phase HPLC to provide the title compound (8 mg, 21%). $^1$H NMR (400 MHz, DMSO-$d_6$) δ 10.31 (s, 1H), 9.40 (s, 1H), 8.41 (d, J=8.0 Hz, 1H), 8.14-7.97 (m, 6H), 7.69 (d, J=8.5 Hz, 2H), 7.47 (t, J=7.9 Hz, 1H), 7.13 (dd, J=8.3, 2.6 Hz, 1H), 4.56 (s, 2H), 4.32 (h, J=8.4 Hz, 1H), 2.17-2.00 (m, 4H), 1.65-1.58 (m, 2H). MS (ES+) m/e 498 (M+H)$^+$.

Example 24

2-(3-(7-((4-(1H-pyrazol-4-yl)phenyl)amino)thiazolo[5,4-d]pyrimidin-5-yl)phenoxy)-N-cyclopentylacetamide

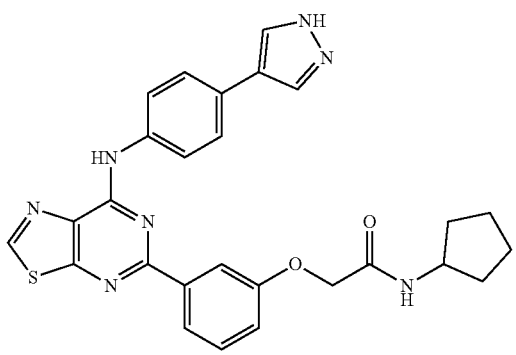 [SMILES: O=C(COc1cccc(-c2nc(Nc3ccc(-c4cn[nH]c4)cc3)c3ncsc3n2)c1)NC1CCCC1]

A mixture of N-(4-(1H-pyrazol-4-yl)phenyl)-5-chlorothiazolo[5,4-d]pyrimidin-7-amine (25 mg, 0.08 mmol), N-cyclopentyl-2-(3-(4,4,5,5-tetramethyl-1,3,2-dioxaborolan-2-yl)phenoxy)acetamide (24 mg, 0.08 mmol), tetrakis(triphenylphosphine)palladium(0) (9 mg, 0.01 mmol), dioxane (0.77 mL), water (0.08 mL), and saturated $Na_2CO_3$ (0.08 mL) was heated in microwave at 180° C. for 2 h. The mixture was concentrated in vacuo to remove the volatiles. The residue was dissolved in DMSO and purified by reverse-phase HPLC to provide the title compound (6 mg, 16%). $^1$H NMR (400 MHz, DMSO-$d_6$) δ 10.31 (s, 1H), 9.40 (s, 1H), 8.20-7.96 (m, 8H), 7.69 (d, J=8.6 Hz, 2H), 7.46 (t, J=8.1 Hz, 1H), 7.12 (dd, J=8.1, 2.6 Hz, 1H), 4.57 (s, 2H), 4.14-4.08 (m, 1H), 1.83-1.63 (m, 4H), 1.51-1.45 (m, 4H). MS (ES+) m/e 512 (M+H)$^+$.

Example 25

2-(3-(7-((4-(1H-pyrazol-4-yl)phenyl)amino)thiazolo[5,4-d]pyrimidin-5-yl)phenoxy)-N-isobutylacetamide

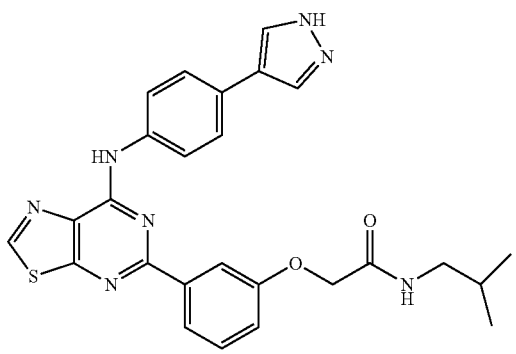 [SMILES: CC(C)CNC(=O)COc1cccc(-c2nc(Nc3ccc(-c4cn[nH]c4)cc3)c3ncsc3n2)c1]

A mixture of N-(4-(1H-pyrazol-4-yl)phenyl)-5-chlorothiazolo[5,4-d]pyrimidin-7-amine (25 mg, 0.08 mmol), N-isobutyl-2-(3-(4,4,5,5-tetramethyl-1,3,2-dioxaborolan-2-yl)phenoxy)acetamide (24 mg, 0.08 mmol), tetrakis(triphenylphosphine)palladium(0) (9 mg, 0.01 mmol), dioxane (0.77 mL), water (0.08 mL), and saturated Na$_2$CO$_3$ (0.08 mL) was heated in microwave at 180° C. for 2 h. The mixture was concentrated in vacuo to remove the volatiles. The residue was dissolved in DMSO and purified by reverse-phase HPLC to provide the title compound (10 mg, 26%). $^1$H NMR (400 MHz, DMSO-d$_6$) δ 10.31 (s, 1H), 9.40 (s, 1H), 8.17 (t, J=6.0 Hz, 1H), 8.12-7.99 (m, 6H), 7.69 (d, J=8.3 Hz, 2H), 7.46 (t, J=8.1 Hz, 1H), 7.13 (dd, J=8.2, 2.5 Hz, 1H), 4.61 (s, 2H), 2.97 (t, J=6.5 Hz, 2H), 1.75 (hept, J=6.7 Hz, 1H), 0.81 (d, J=6.7 Hz, 6H). MS (ES+) m/e 500 (M+H)$^+$.

Example 26

2-(3-(4-((4-(1H-pyrazol-4-yl)phenyl)amino)-5,7-dihydrofuro[3,4-d]pyrimidin-2-yl)phenoxy)-N-(tert-butyl)acetamide dihydrochloride

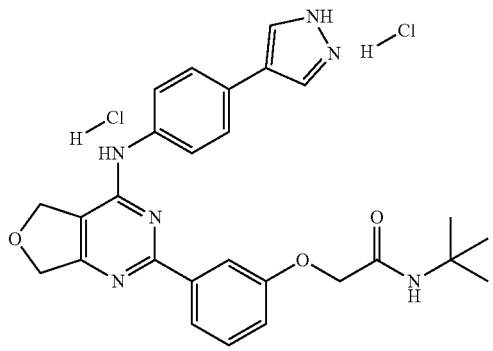

Example 26A

N-(tert-butyl)-2-chloroacetamide

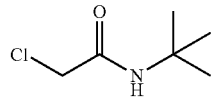

To the mixture of 2-methylpropan-2-amine (4.21 g, 57.55 mmol, 6.01 mL) and TEA (13.44 g, 132.81 mmol, 18.41 mL) in CH$_2$Cl$_2$ (100.00 mL) was added 2-chloroacetyl chloride (5.00 g, 44.27 mmol, 3.52 mL) drop-wise at 0° C. The mixture was stirred under N$_2$ at 23° C. for 3 h. TLC (petroleum ether/EtOAc=0:1, Rf=0.65) showed that one new main spot was detected. The mixture was diluted with CH$_2$Cl$_2$ (50 mL) and washed with water (50 mL×2), citric acid (10%, 50 mL×3), sat.NaHCO$_3$ (50 mL×2), brine (50 mL×2). The organic layer was dried over Na$_2$SO$_4$, filtered and concentrated under reduced pressure to give the title compound (3.49 g, crude) as a black brown solid which was used in the next step without further purification. $^1$H NMR (400 MHz, DMSO-d$_6$) δ 7.80 (s, 1H), 3.95 (s, 2H), 1.32 (s, 9H).

Example 26B 2-(3-bromophenoxy)-N-(tert-butyl)acetamide

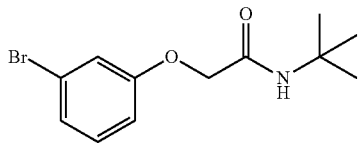 [SMILES: CC(C)(C)NC(=O)COc1cccc(Br)c1]

To a mixture of N-(tert-butyl)-2-chloroacetamide (3.48 g, 23.26 mmol) and 3-bromophenol (3.62 g, 20.93 mmol) in MeCN (40.00 mL) was added K$_2$CO$_3$ (6.43 g, 46.52 mmol). The mixture was stirred at 70° C. for 16 h. TLC (petroleum ether/EtOAc=5:1, Rf=0.62) showed one new main spot was detected. The reaction mixture was diluted with water (50 mL) and extracted with EtOAc (50 mL×3). The combined organic layers were dried over Na$_2$SO$_4$, filtered, and concentrated under reduced pressure to give a residue. The residue was purified by column chromatography (SiO$_2$) to give the title compound (3.52 g, 53%) as a white solid. $^1$H NMR (400 MHz, DMSO-d$_6$) δ 7.55 (s, 1H), 7.25 (t, J=8.4 Hz, 1H), 7.15-7.13 (m, 2H), 6.95-6.93 (m, 1H), 4.43 (s, 2H), 1.28 (m, 9H).

Example 26C

N-(tert-butyl)-2-(3-(4,4,5,5-tetramethyl-1,3,2-dioxaborolan-2-yl)phenoxy)acetamide

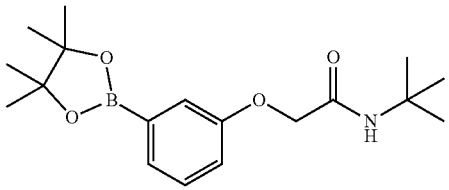 [SMILES: CC(C)(C)NC(=O)COc1cccc(B2OC(C)(C)C(C)(C)O2)c1]

To a mixture of 2-(3-bromophenoxy)-N-(tert-butyl)acetamide (3.50 g, 12.23 mmol) and 4,4,4',4',5,5,5',5'-octamethyl-2,2'-bi(1,3,2-dioxaborolane) (4.66 g, 18.35 mmol) in dioxane (70.00 mL) was added AcOK (2.40 g, 24.46 mmol), Pd(dppf)Cl$_2$ (447.44 mg, 611.50 umol). The mixture was stirred under N$_2$ at 90° C. for 16 h. TLC (petroleum ether/EtOAc=5:1, Rf=0.61) showed that one main spot was detected. The reaction mixture was diluted with water (50 mL) and the mixture was extracted with EtOAc (50 mL×3). The combined organic layers were dried over Na$_2$SO$_4$, filtered and concentrated under reduced pressure to give a residue. The residue was purified by column chromatography (SiO$_2$, petroleum ether/EtOAc=1:0 to 10:1) to give the title compound (3.88 g, 95%) as a white solid.

$^1$H NMR (400 MHz, DMSO-d$_6$) δ 7.55 (s, 1H), 7.33-7.25 (m, 2H), 7.20-7.19 (m, 1H), 7.07-7.05 (m, 1H), 4.40 (s, 2H), 1.29-1.28 (m, 21H).

Example 26D

N-(tert-butyl)-2-(3-(4-((4-(1-(tetrahydro-2H-pyran-2-yl)-1H-pyrazol-4-yl)phenyl)amino)-5,7-dihydrofuro[3,4-d]pyrimidin-2-yl)phenoxy)acetamide

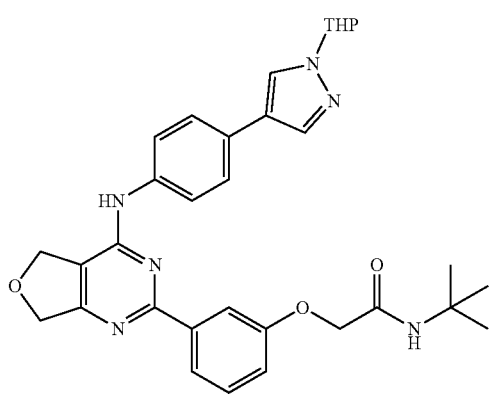

To a mixture of N-(tert-butyl)-2-(3-(4,4,5,5-tetramethyl-1,3,2-dioxaborolan-2-yl)phenoxy)acetamide (700.00 mg, 2.10 mmol) and 2-chloro-N-(4-(1-(tetrahydro-2H-pyran-2-yl)-1H-pyrazol-4-yl)phenyl)-5,7-dihydrofuro[3,4-d]pyrimidin-4-amine (751.96 mg, 1.89 mmol) in dioxane (15.00 mL), H$_2$O (1.50 mL) was added K$_2$CO$_3$ (580.48 mg, 4.20 mmol), Pd(dppf)Cl$_2$ (153.66 mg, 210.00 umol). The mixture was stirred under N$_2$ at 100° C. for 16 h. TLC (petroleum ether/EtOAc=1:2, Rf=0.63) showed one new main spot was detected. The reaction mixture was cooled to room temperature, diluted with water (40 mL) and the mixture was extracted with EtOAc (40 mL×3). The combined organic layers were washed with brine (30 mL×2), dried over Na$_2$SO$_4$, filtered, and concentrated under reduced pressure to give a residue. The residue was purified by column chromatography (SiO$_2$, petroleum ether/EtOAc=1:0 to 1:2) to give the title compound (760 mg, 58%) as a yellow solid.

$^1$H NMR (400 MHz, DMSO-d$_6$) δ 9.24 (s, 1H), 8.35 (s, 1H), 7.96-7.94 (m, 3H), 7.82 (d, J=8.0 Hz, 2H), 7.66 (d, J=8.8 Hz, 2H), 7.52 (s, 1H), 7.43-7.39 (m, 1H), 7.09-7.07 (m, 1H), 5.41 (d, J=8.4 Hz, 1H), 5.08 (s, 2H), 4.94 (s, 2H), 4.49 (s, 2H), 3.96-3.94 (m, 1H), 3.68-3.62 (m, 1H), 2.19-2.10 (m, 1H), 1.97-1.94 (m, 2H), 1.70-1.65 (m, 1H), 1.57-1.56 (m, 2H), 1.30 (s, 9H).

Example 26E 2-(3-(4-((4-(1H-pyrazol-4-yl)phenyl)amino)-5,7-dihydrofuro[3,4-d]pyrimidin-2-yl)phenoxy)-N-(tert-butyl)acetamide

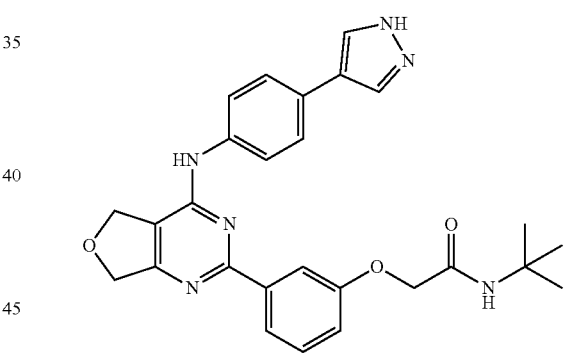

To a mixture of N-(tert-butyl)-2-(3-(4-((4-(1-(tetrahydro-2H-pyran-2-yl)-1H-pyrazol-4-yl)phenyl)amino)-5,7-dihydrofuro[3,4-d]pyrimidin-2-yl)phenoxy)acetamide (760.00 mg, 1.34 mmol) in CH$_2$Cl$_2$ (30.00 mL) was added HCl/dioxane (4 M, 30.00 mL). The mixture was stirred at 20° C. for 5 h. LCMS showed it had about 83% of desired product and about 9.8% of starting material. The mixture was concentrated under reduced pressure to give a residue. The residue was purified by prep-HPLC (FA conditions) to give the title compound (195 mg, 30%) as an off-white solid. $^1$H NMR (400 MHz, DMSO-d$_6$) δ 9.24 (s, 1H), 7.96-7.93 (m, 4H), 7.80 (d, J=8.4 Hz, 2H), 7.65 (d, J=8.4 Hz, 2H), 7.54 (s, 1H), 7.42 (t, J=7.8 Hz, 1H), 7.08-7.06 (m, 2H), 5.07 (s, 2H), 4.93 (s, 2H), 4.48 (s, 2H), 1.29 (s, 9H).

Example 26F 2-(3-(4-((4-(1H-pyrazol-4-yl)phenyl)amino)-5,7-dihydrofuro[3,4-d]pyrimidin-2-yl)phenoxy)-N-(tert-butyl)acetamide dihydrochloride

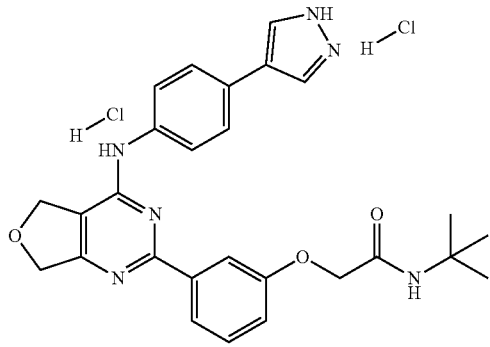

To the solution of 2-(3-(4-((4-(1H-pyrazol-4-yl)phenyl)amino)-5,7-dihydrofuro[3,4-d]pyrimidin-2-yl)phenoxy)-N-(tert-butyl)acetamide (193.00 mg, 398.31 umol) in THF (10.00 mL) was added HCl/dioxane (4 M, 497.89 uL). The mixture was stirred at 18° C. for 3 h. When a large amount of precipitate separated out after the addition of HCl/dioxane, Deionized water (50 mL) was added. The resulting mixture was concentrated under reduce pressure to remove the organic solvent. The aqueous layer was lyophilized to give the title compound (182.70 mg, 87%) as a deep yellow solid. $^1$H NMR (400 MHz, DMSO-d$_6$) δ 9.99 (s, 1H), 8.19 (s, 2H), 7.96-7.94 (m, 2H), 7.81 (d, J=8.4 Hz, 2H), 7.70 (d, J=8.8 Hz, 2H), 7.58 (s, 1H), 7.47 (t, J=8.0 Hz, 1H), 7.16-7.14 (m, 1H), 5.10 (s, 2H), 5.02 (s, 2H), 4.52 (s, 2H), 1.28 (s, 9H). (ES+) m/e 485.2 (M+H)$^+$.

Example 27

2-(3-(4-((4-(1H-pyrazol-4-yl)phenyl)amino)-5,7-dihydrofuro[3,4-d]pyrimidin-2-yl)phenoxy)-N-(pentan-3-yl)acetamide dihydrochloride

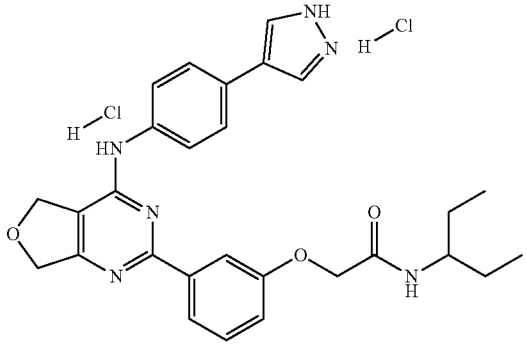

Example 27A 2-chloro-N-(pentan-3-yl)acetamide

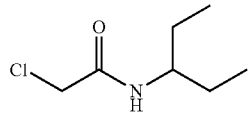

To a mixture of pentan-3-amine (5.79 g, 66.41 mmol, 7.72 mL) and TEA (13.44 g, 132.81 mmol, 18.41 mL) in CH$_2$Cl$_2$ (100.00 mL) was added 2-chloroacetyl chloride (5.00 g, 44.27 mmol, 3.52 mL) dropwise at 0° C. The mixture was stirred under N$_2$ at 23° C. for 3 h. TLC (petroleum ether/EtOAc=0:1, Rf=0.6) showed one new main spot. The mixture was diluted with CH$_2$Cl$_2$ (40 mL) and washed with water (50 mL×2), citric acid (10%, 50 mL×3), sat.NaHCO$_3$ (50 mL×2), brine (50 mL×2). The organic layer was dried over Na$_2$SO$_4$, filtered and concentrated under reduced pressure to give the title compound (5.21 g, crude) as a black brown solid. $^1$H NMR (400 MHz, DMSO-d$_6$) δ 7.89 (d, J=8.0 Hz, 1H), 4.02 (s, 2H), 3.55-3.48 (m, 1H), 1.48-1.42 (m, 2H), 1.36-1.30 (m, 2H), 0.81 (t, J=7.4 Hz, 6H).

Example 27B 2-(3-bromophenoxy)-N-(pentan-3-yl)acetamide

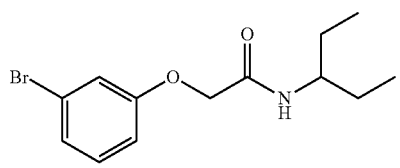 [SMILES: CCC(CC)NC(=O)COc1cccc(Br)c1]

To the mixture of 2-chloro-N-(pentan-3-yl)acetamide (2.00 g, 12.22 mmol) and 3-bromophenol (1.90 g, 11.00 mmol) in MeCN (40.00 mL) was added K$_2$CO$_3$ (3.38 g, 24.44 mmol). The mixture was stirred at 70° C. for 16 h. TLC (petroleum ether/EtOAc=2:1, Rf=0.72) showed one main spot was detected. The reaction mixture was diluted with water (50 mL) and extracted with EtOAc (50 mL×3). The combined organic layers were dried over Na$_2$SO$_4$, filtered and concentrated under reduced pressure to give a residue. The residue was purified by column chromatography (SiO$_2$) to give the title compound (2.41, 66%) as a light yellow solid. $^1$H NMR (400 MHz, DMSO-d$_6$) δ 7.74 (d, J=8.8 Hz, 1H), 7.25 (d, J=8.2 Hz, 1H), 7.15-7.13 (m, 2H), 6.98-6.95 (m, 1H), 4.53 (s, 2H), 3.62-3.55 (m, 1H), 1.47-1.32 (m, 4H), 0.78 (t, J=7.4 Hz, 6H).

Example 27C

N-(pentan-3-yl)-2-(3-(4,4,5,5-tetramethyl-1,3,2-dioxaborolan-2-yl)phenoxy)acetamide

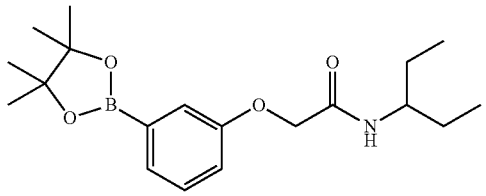 [SMILES: CCC(CC)NC(=O)COc1cccc(B2OC(C)(C)C(C)(C)O2)c1]

To a mixture of 2-(3-bromophenoxy)-N-(pentan-3-yl)acetamide (2.40 g, 7.99 mmol) and 4,4,4',4',5,5,5',5'-octamethyl-2,2'-bi(1,3,2-dioxaborolane) (3.05 g, 11.99 mmol) in dioxane (30.00 mL) was added Pd(dppf)Cl$_2$ (292.32 mg, 399.50 umol) and AcOK (1.57 g, 15.99 mmol). The mixture was stirred under N$_2$ at 90° C. for 16 h. TLC (petroleum ether/EtOAc=3:1, Rf=0.52) detected one new main spot. The reaction mixture was cooled to room temperature, diluted with water (50 mL) and the mixture was extracted with EtOAc (50 mL×3). The combined organic layers were dried over Na$_2$SO$_4$, filtered and concentrated under reduced pressure to give a residue. The residue was purified by column chromatography (SiO$_2$, petroleum ether/EtOAc=1:0 to 8:1) to give the title compound (3.05 g, 74%) as a light yellow solid. $^1$H NMR (400 MHz, DMSO-d$_6$) δ 7.72 (d, J=8.8 Hz, 1H), 7.33-7.25 (m, 2H), 7.21-7.20 (m, 1H), 7.08 (d, J=1.2 Hz, 1H), 4.49 (s, 2H), 3.64-3.58 (m, 1H), 1.46-1.33 (m, 4H), 1.28 (s, 12H), 0.79 (t, J=7.4 Hz, 6H).

Example 27D

N-(pentan-3-yl)-2-(3-(4-((4-(1-(tetrahydro-2H-pyran-2-yl)-1H-pyrazol-4-yl)phenyl)amino)-5,7-dihydrofuro[3,4-d]pyrimidin-2-yl)phenoxy)acetamide

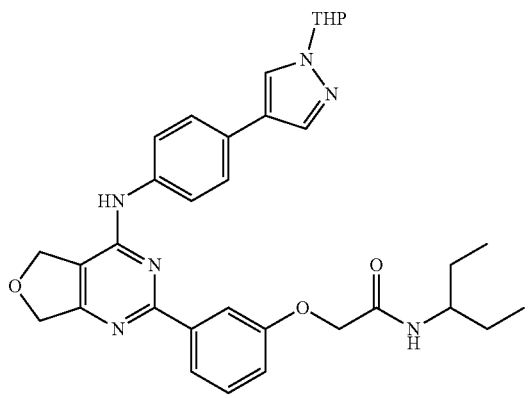

To the mixture of N-(pentan-3-yl)-2-(3-(4,4,5,5-tetramethyl-1,3,2-dioxaborolan-2-yl)phenoxy)acetamide (400.00 mg, 1.15 mmol) and 2-chloro-N-(4-(1-(tetrahydro-2H-pyran-2-yl)-1H-pyrazol-4-yl)phenyl)-5,7-dihydrofuro[3,4-d]pyrimidin-4-amine (434.66 mg, 1.09 mmol) in dioxane (15.00 mL) and H$_2$O (1.50 mL) was added K$_2$CO$_3$ (317.88 mg, 2.30 mmol), Pd(dppf)Cl$_2$ (84.15 mg, 115.00 umol). The mixture was stirred under N$_2$ at 100° C. for 6 h. TLC (petroleum ether/EtOAc=1:2, Rf=0.51) detected one new main spot. The mixture (two small experiments were combined together) was cooled to room temperature, diluted with water (40 mL) and the mixture was extracted with EtOAc (40 mL×3). The combined organic layers were washed with brine (40 mL×2), dried over Na$_2$SO$_4$, filtered and concentrated under reduced pressure to give a residue. The residue was purified by column chromatography (SiO$_2$, petroleum ether/EtOAc=1:0 to 1:1) to give the title compound (690 mg) as a yellow solid. $^1$H NMR (400 MHz, DMSO-d$_6$) δ 9.24 (s, 1H), 8.34 (s, 1H), 7.97-7.95 (m, 3H), 7.83-7.80 (m, 2H), 7.68-7.62 (m, 5H), 7.42-7.40 (m, 1H), 7.10 (d, J=8.0 Hz, 1H), 5.40 (d, J=9.6 Hz, 1H), 5.08 (s, 2H), 4.93 (s, 2H), 4.58 (s, 2H), 3.96-3.93 (m, 1H), 3.68-3.58 (m, 2H), 2.16-2.10 (m, 1H), 1.97-1.92 (m, 2H), 1.71-1.66 (m, 1H), 1.57-1.52 (m, 2H), 1.48-1.36 (m, 1H), 0.78 (t, J=7.4 Hz, 6H).

Example 27E 2-(3-(4-((4-(1H-pyrazol-4-yl)phenyl)amino)-5,7-dihydrofuro[3,4-d]pyrimidin-2-yl)phenoxy)-N-(pentan-3-yl)acetamide

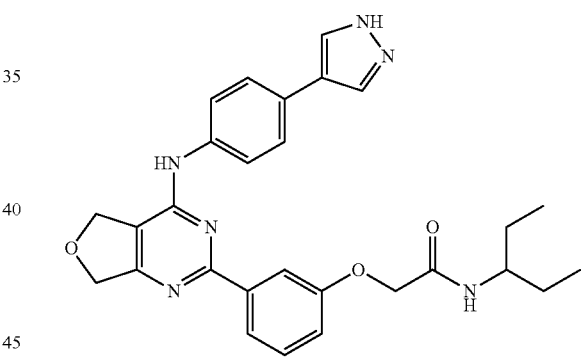

To a mixture of N-(pentan-3-yl)-2-(3-(4-((4-(1-(tetrahydro-2H-pyran-2-yl)-1H-pyrazol-4-yl)phenyl)amino)-5,7-dihydrofuro[3,4-d]pyrimidin-2-yl)phenoxy)acetamide (590.00 mg, 1.01 mmol) in CH$_2$Cl$_2$ (4.00 mL) was added HCl/dioxane (4 M, 6.00 mL). The mixture was stirred at 30° C. for 2.5 h. LCMS showed about 87% of desired product and 2% of starting material. The mixture was concentrated under reduced pressure to give a residue. The residue (about 100 mg crude product was used together) was purified by prep-HPLC (FA conditions). But HNMR showed the product contained some MeCN. The product was suspended in distilled water and the mixture was stirred at 95° C. for 16 h and collected by filtration. The product was resuspended in water and stirred at 120° C. for another 16 h and was lyophilized to provide the title compound (195 mg) as an off-white solid. $^1$H NMR (400 MHz, DMSO-d$_6$) δ 9.22 (s, 1H), 8.17 (s, 1H), 7.97-7.92 (m, 3H), 7.81-7.74 (m, 3H), 7.65 (d, J=8.4 Hz, 2H), 7.42 (t, J=8.0 Hz, 1H), 7.10-7.08 (m, 1H), 5.07 (s, 2H), 4.93 (s, 2H), 4.58 (s, 2H), 3.65-3.61 (m, 1H), 1.47-1.34 (m, 4H), 0.78 (t, J=7.4 Hz, 6H).

Example 27F 2-(3-(4-((4-(1H-pyrazol-4-yl)phenyl)amino)-5,7-dihydrofuro[3,4-d]pyrimidin-2-yl)phenoxy)-N-(pentan-3-yl)acetamide dihydrochloride

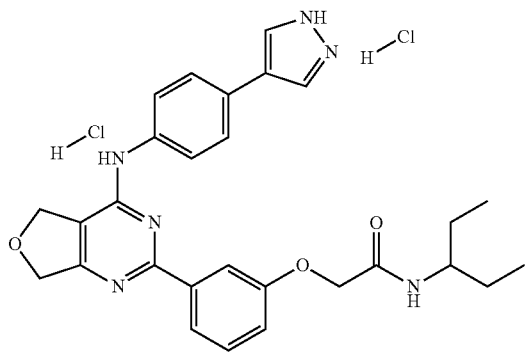

To the mixture of 2-(3-(4-((4-(1H-pyrazol-4-yl)phenyl)amino)-5,7-dihydrofuro[3,4-d]pyrimidin-2-yl)phenoxy)-N-(pentan-3-yl)acetamide (195.00 mg, 391.11 umol) in THF (300.00 mL) was added HCl/dioxane (4 M, 488.89 uL). The mixture was stirred at 18° C. for 16 h. Precipitates formed after the addition of HCl/dioxane. A small amount of mixture was concentrated under reduce pressure to provide a residue. HNMR showed the product was HCl salt. Deion water (20 mL) was added to the mixture. The resulting mixture was concentrated under reduce pressure to remove the organic solvent. To the mixture was added deion water (60 mL). The mixture was lyophilized to give the product as yellow solid. HNMR showed the product contained some organic solvents. The product was redissolved with deion water (50 mL) and CH$_2$Cl$_2$ (50 mL). The mixture was stirred at 18° C. for 13 h. Three layers were observed after standing for 30 min. Lactescence in middle layer was lyophilized to afford the title compound (135.1 mg) as a yellow solid. $^1$H NMR (400 MHz, DMSO-d$_6$) δ 9.54 (s, 1H), 8.11 (s, 2H), 7.94 (s, 2H), 7.82-7.76 (m, 3H), 7.68 (d, J=8.4 Hz, 2H), 7.45 (t, J=8.0 Hz, 1H), 7.13 (d, J=8.0 Hz, 1H), 5.08 (s, 2H), 4.97 (s, 2H), 4.59 (s, 2H), 3.63-3.61 (m, 1H), 1.47-1.34 (m, 4H), 0.78 (t, J=7.4 Hz, 6H). (ES+) m/e 499.3 (M+H)$^+$.

Example 28

2-(3-(4-((4-(1H-pyrazol-4-yl)phenyl)amino)-5,7-dihydrofuro[3,4-d]pyrimidin-2-yl)phenoxy)-N-(sec-butyl)acetamide

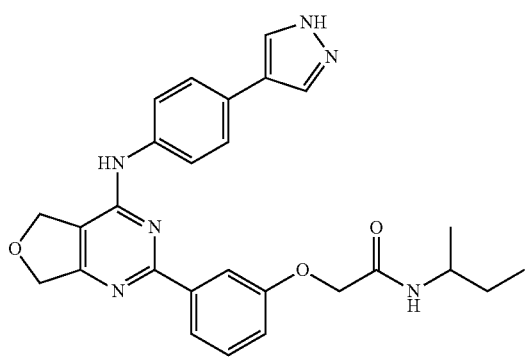 [SMILES: CCC(C)NC(=O)COc1cccc(-c2nc3c(c(Nc4ccc(-c5cn[nH]c5)cc4)n2)COC3)c1]

Example 28A

N-(sec-butyl)-2-chloroacetamide

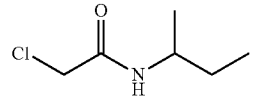

To the mixture of 2-methylpropan-1-amine (1.94 g, 26.57 mmol, 2.70 mL) and TEA (5.38 g, 53.12 mmol, 7.37 mL) in CH$_2$Cl$_2$ (30.00 mL) was added dropwise 2-chloroacetyl chloride (2.00 g, 17.71 mmol, 1.41 mL) at 0° C. The mixture was stirred at 28° C. for 2 h. TLC (petroleum ether/EtOAc=2:1, Rf=0.7) detected one new main spot. The mixture was diluted with CH$_2$Cl$_2$ (30 mL) and washed with water (40 mL×2), citric acid (10%, 40 mL×2), NaHCO$_3$ (40 mL×2), brine (40 mL×2). The organic layer was dried over Na$_2$SO$_4$, filtered and concentrated under reduced pressure to give the title compound (2.60 g, crude) as a black oil and used for the next step reaction without further purification. $^1$H NMR (400 MHz, DMSO-d$_6$) δ 8.00-7.98 (m, 1H), 4.00 (s, 2H), 3.71-3.61 (m, 1H), 1.43-1.36 (m, 2H), 1.03 (d, J=6.8 Hz, 3H), 0.82 (t, J=7.4 Hz, 3H).

Example 28B

N-(sec-butyl)-2-(3-(4,4,5,5-tetramethyl-1,3,2-dioxaborolan-2-yl)phenoxy)acetamide

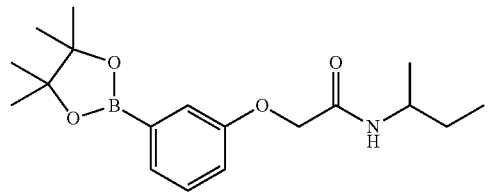 [SMILES: CCC(C)NC(=O)COc1cccc(B2OC(C)(C)C(C)(C)O2)c1]

To the mixture of 3-(4,4,5,5-tetramethyl-1,3,2-dioxaborolan-2-yl)phenol (1.00 g, 4.54 mmol) and N-(sec-butyl)-2-chloroacetamide (815.85 mg, 5.45 mmol) in MeCN (30.00 mL) was added K$_2$CO$_3$ (1.25 g, 9.08 mmol). The mixture was stirred at 70° C. for 16 h. TLC (petroleum ether/EtOAc=3:1, Rf=0.51) detected one new main spot. The reaction mixture was cooled to room temperature, diluted with water (30 mL) and the mixture was extracted with EtOAc (30 mL×3). The combined organic layers were dried over Na$_2$SO$_4$, filtered and concentrated under reduced pressure to give a residue. The residue was purified by column chromatography (SiO$_2$, petroleum ether/EtOAc=100:1 to 5:1) to give the title compound (481 mg, 32%) as a light yellow solid. $^1$H NMR (400 MHz, DMSO-d$_6$) δ 7.84-7.81 (m, 1H), 7.33-7.25 (m, 2H), 7.22-7.21 (m, 1H), 7.08-7.06

(m, 1H), 4.46 (s, 2H), 3.80-3.73 (m, 1H), 1.46-1.38 (m, 2H), 1.28 (s, 12H), 1.08-1.06 (m, 3H), 0.80 (t, J=7.4 Hz, 3H).

Example 28C tert-butyl 4-(4-((tert-butoxycarbonyl)(2-(3-(2-(sec-butylamino)-2-oxoethoxy)phenyl)-5,7-dihydrofuro[3,4-d]pyrimidin-4-yl)amino)phenyl)-1H-pyrazole-1-carboxylate

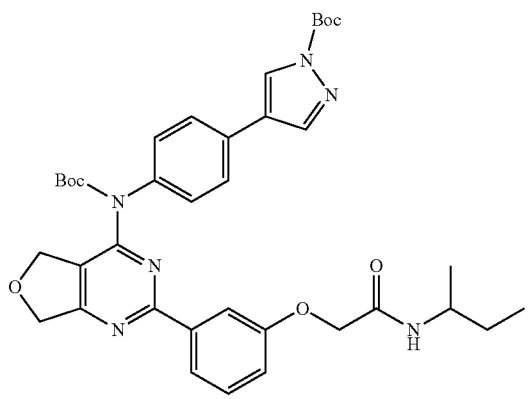 [SMILES: CCC(C)NC(=O)COc1cccc(-c2nc3c(c(N(C(=O)OC(C)(C)C)c4ccc(-c5cnn(C(=O)OC(C)(C)C)c5)cc4)n2)COC3)c1]

To the mixture of N-(sec-butyl)-2-(3-(4,4,5,5-tetramethyl-1,3,2-dioxaborolan-2-yl)phenoxy)acetamide (150.00 mg, 450.14 umol) and tert-butyl 4-(4-((tert-butoxycarbonyl)(2-chloro-5,7-dihydrofuro[3,4-d]pyrimidin-4-yl)amino)phenyl)-1H-pyrazole-1-carboxylate (210.33 mg, 409.22 umol) in dioxane (3.00 mL), H₂O (300.00 uL) was added K₂CO₃ (113.12 mg, 818.44 umol) and Pd(dppf)Cl₂ (29.94 mg, 40.92 umol). The mixture was stirred under N₂ at 100° C. for 16 h. TLC (petroleum ether/EtOAc=1:2, Rf=0.35) detected one main new spot. The reaction mixture was cooled to room temperature, water (30 mL) was added and the mixture was extracted with EtOAc (30 mL×3). The combined organic layers were dried over Na₂SO₄, filtered and concentrated under reduced pressure to give a residue. The residue was purified by prep-TLC (petroleum ether/EtOAc=1:2) to give the title compound (190 mg, mono-Boc product) as a light yellow solid. ¹H NMR (400 MHz, DMSO-d₆) δ 12.98 (s, 1H), 8.24 (s, 1H), 7.84 (s, 1H), 7.81-7.75 (m, 3H), 7.66 (d, J=8.8 Hz, 2H), 7.36-7.34 (m, 1H), 7.29-7.27 (m, 2H), 7.07-7.06 (m, 1H), 5.03 (s, 2H), 4.86 (s, 2H), 4.47 (s, 2H), 3.79-3.72 (m, 1H), 1.55-1.37 (m, 11H), 1.04 (d, J=6.8 Hz, 3H), 0.80-0.76 (m, 3H).

Example 28D 2-(3-(4-((4-(1H-pyrazol-4-yl)phenyl)amino)-5,7-dihydrofuro[3,4-d]pyrimidin-2-yl)phenoxy)-N-(sec-butyl)acetamide

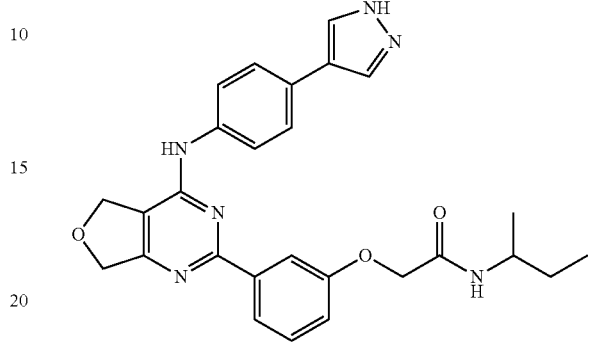

To a mixture of tert-butyl 4-(4-((tert-butoxycarbonyl)(2-(3-(2-(sec-butylamino)-2-oxoethoxy)phenyl)-5,7-dihydrofuro[3,4-d]pyrimidin-4-yl)amino)phenyl)-1H-pyrazole-1-carboxylate (mono-Boc product, 190.00 mg) in CH₂Cl₂ (6.00 mL) was added HCl/dioxane (4 M, 3.00 mL). The mixture was stirred at 28° C. for 11 h. LCMS showed about 58% of desired product and about 31% of starting material. To the mixture was added additional HCl/dioxane (4 M, 2 mL) and the mixture was stirred at 28° C. for another 5 h. LCMS showed about 75% of desired product and about 15% of starting material. The mixture was concentrated under reduced pressure to give a residue. The residue was purified by prep-HPLC (FA conditions) to give the title compound (27.30 mg, 17%) as a white solid. ¹H NMR (400 MHz, DMSO-d₆) δ 12.90 (s, 1H), 9.22 (s, 1H), 8.17 (s, 1H), 7.97-7.79 (m, 4H), 7.80 (d, J=8.8 Hz, 2H), 7.65 (d, J=8.8 Hz, 2H), 7.42 (t, J=8.0 Hz, 1H), 7.10-7.08 (m, 1H), 5.07 (s, 2H), 4.93 (s, 2H), 4.55 (s, 2H), 3.83-3.78 (m, 1H), 1.44-1.40 (m, 1H), 1.06 (d, J=6.4 Hz, 3H), 0.79 (t, J=7.4 Hz, 3H). (ES+) m/e 485.2 (M+H)⁺.

Example 29

2-(3-(4-((4-(1H-pyrazol-4-yl)phenyl)amino)-5,7-dihydrofuro[3,4-d]pyrimidin-2-yl)phenoxy)-N-isobutylacetamide

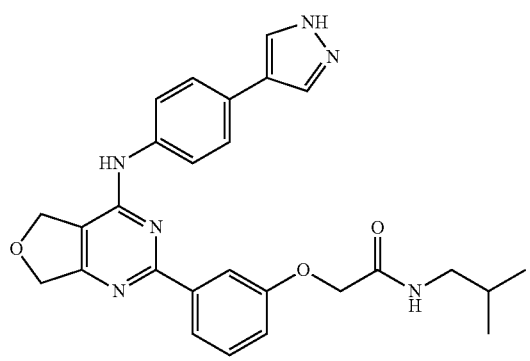 [SMILES: CC(C)CNC(=O)COc1cccc(-c2nc3c(c(Nc4ccc(-c5cn[nH]c5)cc4)n2)COC3)c1]

Example 29A 2-chloro-N-isobutylacetamide

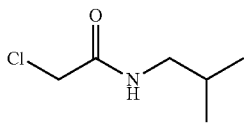

To the mixture of 2-methylpropan-1-amine (1.94 g, 26.57 mmol, 2.63 mL) and TEA (5.38 g, 53.12 mmol, 7.37 mL) in CH$_2$Cl$_2$ (30.00 mL) was added 2-chloroacetyl chloride (2.00 g, 17.71 mmol, 1.41 mL) dropwise at 0° C. The mixture was stirred at 28° C. for 2 h. TLC (petroleum ether/EtOAc=2:1, Rf=0.7) showed one new main spot. The mixture was diluted with CH$_2$Cl$_2$ (30 mL) and washed with water (40 mL×2), citric acid (10%, 40 mL×2), sat.NaHCO$_3$ (40 mL×2), brine (40 mL×2). The organic layer was dried over Na$_2$SO$_4$, filtered and concentrated under reduced pressure to give the title compound (1.83 g, crude) as a black oil which was used in the next step without further purification. $^1$H NMR (400 MHz, DMSO-d$_6$) δ 8.18-8.07 (m, 1H), 4.04 (s, 2H), 2.91 (t, J=6.4 Hz, 2H), 1.73-1.67 (m, 1H), 0.83 (t, J=6.0 Hz, 6H).

Example 29B

N-isobutyl-2-(3-(4,4,5,5-tetramethyl-1,3,2-dioxaborolan-2-yl)phenoxy)acetamide

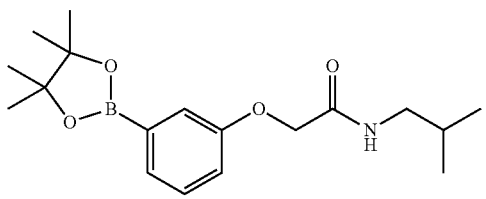 [SMILES: CC(C)CNC(=O)COc1cccc(B2OC(C)(C)C(C)(C)O2)c1]

To the mixture of 3-(4,4,5,5-tetramethyl-1,3,2-dioxaborolan-2-yl)phenol (1.00 g, 4.54 mmol) and 2-chloro-N-isobutylacetamide (815.13 mg, 5.45 mmol) in MeCN (30.00 mL) was added K$_2$CO$_3$ (1.25 g, 9.08 mmol). The mixture was stirred at 70° C. for 16 h. The reaction mixture was cooled to room temperature. Water (30 mL) was added and the mixture was extracted with EtOAc (30 mL×3). The combined organic layers were dried over Na$_2$SO$_4$, filtered and concentrated under reduced pressure to give a residue. The residue was purified by column chromatography (SiO$_2$, petroleum ether/EtOAc=100:1 to 5:1) to give the title compound (540 mg, 36%) as a light yellow solid. $^1$H NMR (400 MHz, DMSO-d$_6$) δ 8.08-8.05 (m, 1H), 7.33-7.26 (m, 2H), 7.22 (d, J=2.4 Hz, 1H), 7.09 (d, J=1.6 Hz, 1H), 4.48 (s, 2H), 2.96-2.91 (m, 2H), 1.76-1.67 (m, 1H), 1.29 (s, 12H), 0.82 (t, J=5.4 Hz, 6H).

Example 29C tert-butyl 4-(4-((tert-butoxycarbonyl)(2-(3-(2-(isobutylamino)-2-oxoethoxy)phenyl)-5,7-dihydrofuro[3,4-d]pyrimidin-4-yl)amino)phenyl)-1H-pyrazole-1-carboxylate

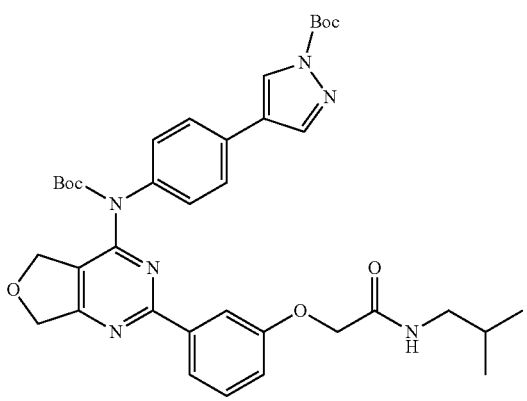 [SMILES: CC(C)CNC(=O)COc1cccc(-c2nc3c(c(N(C(=O)OC(C)(C)C)c4ccc(-c5cnn(C(=O)OC(C)(C)C)c5)cc4)n2)COC3)c1]

To the mixture of N-isobutyl-2-(3-(4,4,5,5-tetramethyl-1,3,2-dioxaborolan-2-yl)phenoxy)acetamide (200.00 mg, 600.19 umol), tert-butyl 4-(4-((tert-butoxycarbonyl)(2-chloro-5,7-dihydrofuro[3,4-d]pyrimidin-4-yl)amino)phenyl)-1H-pyrazole-1-carboxylate (280.44 mg, 545.63 umol) in dioxane (3.00 mL), H$_2$O (300.00 uL) was added K$_2$CO$_3$ (150.82 mg, 1.09 mmol) and Pd(dppf)Cl$_2$ (39.92 mg, 54.56 umol). The mixture was stirred under N$_2$ at 100° C. for 16 h. TLC (petroleum ether/EtOAc=1:2, Rf=0.35, 0.62) detected two main spots. The reaction mixture was cooled to room temperature. Water (30 mL) was added and the mixture was extracted with EtOAc (30 mL×3). The combined organic layers were dried over Na$_2$SO$_4$, filtered and concentrated under reduced pressure to give a residue. The residue was purified by prep-TLC (petroleum ether/EtOAc=1:2) to give the title compound (65.00 mg, mono-Boc product: 136 mg) as a white solid. $^1$H NMR (400 MHz, DMSO-d$_6$) δ 12.98 (s, 1H), 8.24 (s, 1H), 8.10 (s, 1H), 7.97 (s, 1H), 7.82-7.76 (m, 2H), 7.70-7.66 (m, 2H), 7.37-7.33 (m, 2H), 7.29-7.27 (m, 1H), 7.09-7.06 (m, 1H), 5.03 (s, 2H), 4.91-4.86 (m, 2H), 4.49 (d, J=1.2 Hz, 2H), 2.98-2.92 (m, 2H), 1.76-1.66 (m, 1H), 1.43 (m, 4H), 0.80-0.79 (m, 6H).

Example 29D 2-(3-(4-((4-(1H-pyrazol-4-yl)phenyl)amino)-5,7-dihydrofuro[3,4-d]pyrimidin-2-yl)phenoxy)-N-isobutylacetamide

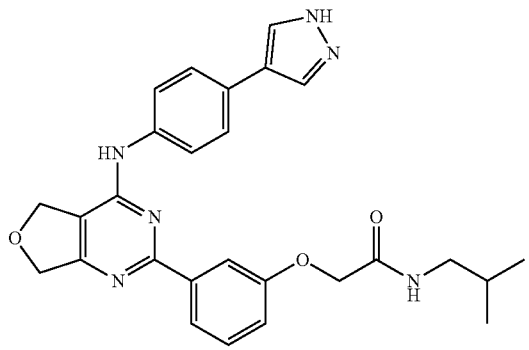 [SMILES: CC(C)CNC(=O)COc1cccc(-c2nc3c(c(Nc4ccc(-c5cn[nH]c5)cc4)n2)COC3)c1]

To a mixture of compound tert-butyl 4-(4-((tert-butoxycarbonyl)(2-(3-(2-(isobutylamino)-2-oxoethoxy)phenyl)-5,7-dihydrofuro[3,4-d]pyrimidin-4-yl)amino)phenyl)-1H-pyrazole-1-carboxylate (65 mg, 136 mg of mono-Boc product was used together) in CH₂Cl₂ (6.00 mL) was added HCl/dioxane (4 M, 3.00 mL). The mixture was stirred at 28° C. for 11 h. The mixture was concentrated under reduced pressure to give a residue. The residue was suspended with sat.NaHCO₃ (20 mL) and the mixture was extracted with EtOAc (30 mL×3). The organic layers were dried over Na₂SO₄, filtered and concentrated under reduced pressure to give a residue. The residue was purified by prep-HPLC (FA conditions) to afford the title compound (9.00 mg, 8%) as a white solid. ¹H NMR (400 MHz, DMSO-d₆) δ 12.92 (s, 1H), 9.25 (s, 1H), 8.15-7.95 (m, 5H), 7.80 (d, J=8.8 Hz, 2H), 7.65 (d, J=8.4 Hz, 2H), 7.42 (d, J=8.0 Hz, 1H), 7.09 (d, J=6.4 Hz, 1H), 5.07 (s, 2H), 4.93 (s, 2H), 4.57 (s, 2H), 2.96 (t, J=6.4 Hz, 2H), 1.78-1.70 (m, 1H), 0.80 (d, J=6.8 Hz, 6H). (ES+) m/e 485.2 (M+H)⁺.

Example 30

2-(3-(4-((4-(1H-pyrazol-4-yl)phenyl)amino)-5,7-dihydrofuro[3,4-d]pyrimidin-2-yl)phenoxy)-N-neopentylacetamide

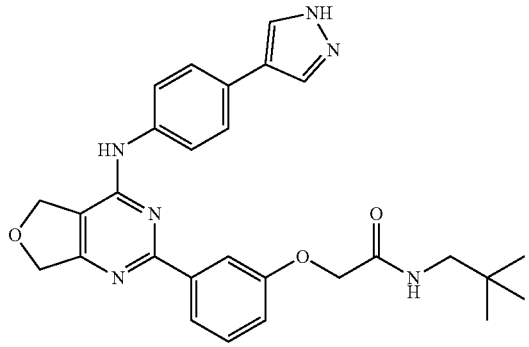 [SMILES: CC(C)(C)CNC(=O)COc1cccc(-c2nc3c(c(Nc4ccc(-c5cn[nH]c5)cc4)n2)COC3)c1]

Example 30A 2-chloro-N-neopentylacetamide

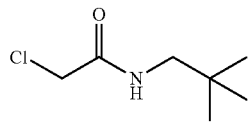

To a mixture of 2,2-dimethylpropan-1-amine (2.32 g, 26.57 mmol) and TEA (5.38 g, 53.12 mmol, 7.37 mL) in CH₂Cl₂ (30.00 mL) was added 2-chloroacetyl chloride (2.00 g, 17.71 mmol, 1.41 mL) dropwise at 0° C. The mixture was stirred at 25° C. for 2 h. The mixture was diluted with CH₂Cl₂ (30 mL) and washed with water (40 mL×2), citric acid (10%, 40 mL×2), sat.NaHCO₃ (40 mL×2), brine (40 mL×2). The organic layer was dried over Na₂SO₄, filtered and concentrated under reduced pressure to give the crude product (2.34 g, crude) as a black oil which was used in the next step reaction without further purification. ¹H NMR (400 MHz, DMSO-d₆) δ 8.08 (s, 1H), 4.06 (s, 2H), 2.96-2.91 (m, 2H), 0.84 (s, 9H).

Example 30B

N-neopentyl-2-(3-(4,4,5,5-tetramethyl-1,3,2-dioxaborolan-2-yl)phenoxy)acetamide

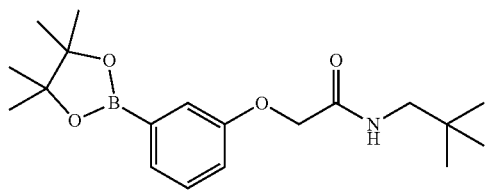 [SMILES: CC(C)(C)CNC(=O)COc1cccc(B2OC(C)(C)C(C)(C)O2)c1]

To the mixture of 2-chloro-N-neopentylacetamide (800.00 mg, 4.89 mmol) and 3-(4,4,5,5-tetramethyl-1,3,2-dioxaborolan-2-yl)phenol (978.01 mg, 4.45 mmol) in MeCN (20.00 mL) was added K₂CO₃ (1.23 g, 8.89 mmol). The mixture was stirred at 70° C. for 16 h. TLC (petroleum ether/EtOAc=3:1, Rf=0.55) showed one new main spot was detected. The reaction mixture was diluted with water (30 mL) and the mixture was extracted with EtOAc (30 mL×3). The combined organic layers were dried over Na₂SO₄, filtered and concentrated under reduced pressure to give a residue. The residue was purified by column chromatography (SiO₂, petroleum ether/EtOAc=1:1 to 5:1) to give the title compound (615 mg, 40%) as a yellow solid. ¹H NMR (400 MHz, DMSO-d₆) δ 7.96-7.92 (m, 1H), 7.33-7.26 (m, 2H), 7.20 (d, J=2.4 Hz, 1H), 7.08 (d, J=8.0 Hz, 1H), 4.53 (s, 2H), 2.94-2.91 (m, 2H), 1.28 (s, 12H), 0.80 (s, 9H).

Example 30C tert-butyl 4-(4-((tert-butoxycarbonyl)(2-(3-(2-(neopentylamino)-2-oxoethoxy)phenyl)-5,7-dihydrofuro[3,4-d]pyrimidin-4-yl)amino)phenyl)-1H-pyrazole-1-carboxylate

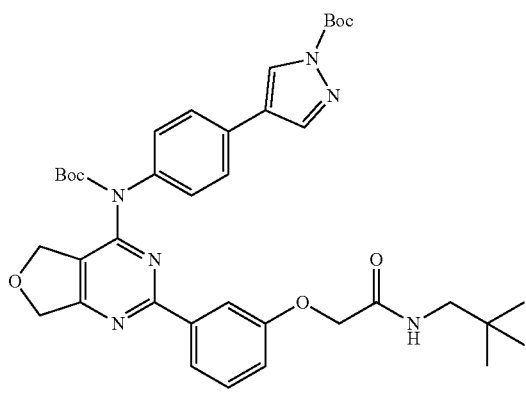 [SMILES: CC(C)(C)CNC(=O)COc1cccc(-c2nc3c(c(N(C(=O)OC(C)(C)C)c4ccc(-c5cnn(C(=O)OC(C)(C)C)c5)cc4)n2)COC3)c1]

To the mixture of N-neopentyl-2-(3-(4,4,5,5-tetramethyl-1,3,2-dioxaborolan-2-yl)phenoxy)acetamide (200.00 mg, 600.19 umol), tert-butyl 4-(4-((tert-butoxycarbonyl)(2-chloro-5,7-dihydrofuro[3,4-d]pyrimidin-4-yl)amino)phenyl)-1H-pyrazole-1-carboxylate (296.01 mg, 575.94 umol) in dioxane (3.00 mL), H$_2$O (300.00 uL) was added K$_2$CO$_3$ (159.20 mg, 1.15 mmol) and Pd(dppf)Cl$_2$ (42.14 mg, 57.59 umol). The mixture was stirred under N$_2$ at 100° C. for 16 h. TLC (petroleum ether/EtOAc=1:1.5, Rf=0.32, 0.78) detected two main spots (desired product and mono-Boc product). The reaction mixture was diluted with (30 mL) and the mixture was extracted with EtOAc (30 mL×3). The combined organic layers were dried over Na$_2$SO$_4$, filtered and concentrated under reduced pressure to give a residue. The residue was purified by prep-TLC (petroleum ether/EtOAc=1:2) to give the title compound (56.00 mg, mono-Boc: 122 mg) as a white solid.

Example 30D 2-(3-(4-((4-(1H-pyrazol-4-yl)phenyl)amino)-5,7-dihydrofuro[3,4-d]pyrimidin-2-yl)phenoxy)-N-neopentylacetamide

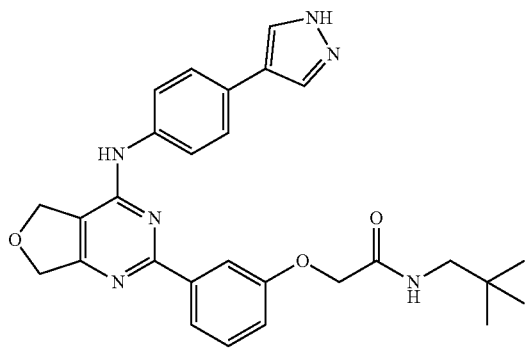 [SMILES: CC(C)(C)CNC(=O)COc1cccc(-c2nc3c(c(Nc4ccc(-c5cn[nH]c5)cc4)n2)COC3)c1]

To a mixture of tert-butyl 4-(4-((tert-butoxycarbonyl)(2-(3-(2-(neopentylamino)-2-oxoethoxy)phenyl)-5,7-dihydrofuro[3,4-d]pyrimidin-4-yl)amino)phenyl)-1H-pyrazole-1-carboxylate (56 mg, 122.00 mg of mono-Boc product was used together) in CH$_2$Cl$_2$ (4.00 mL) was added HCl/dioxane (4 M, 3.5 mL). The mixture was stirred at 25° C. for 17 h. LCMS showed 46% of desired product and 45% of starting material. To the mixture was added additional amount of HCl/dioxane (4M, 2 mL). The mixture was stirred at 25° C. for another 21 h. LCMS about 50% of desired product and about 37% of starting material. To the mixture was added HCl/dioxane (4M, 4 mL), then the mixture was stirred at 25° C. for another 3 h. LCMS showed 49% of desired product and 36% of starting material. The mixture was concentrated under reduced pressure to give a residue. The residue was purified by prep-HPLC (FA conditions) to give the title compound (19.50 mg, 13%) as an off-white solid. $^1$H NMR (400 MHz, DMSO-d$_6$) δ 12.91 (s, 1H), 9.24 (s, 1H), 8.15 (s, 1H), 7.98-7.95 (m, 4H), 7.80 (d, J=8.8 Hz, 2H), 7.42 (d, J=8.2 Hz, 1H), 7.09 (d, J=8.8 Hz, 1H), 5.07 (s, 2H), 4.93 (s, 2H), 4.62 (s, 2H), 2.96 (d, J=6.0 Hz, 2H), 0.80 (s, 9H). (ES+) m/e 499.2 (M+H)$^+$.

Example 31

2-(3-(4-((4-(1H-pyrazol-4-yl)phenyl)amino)-5,7-dihydrofuro[3,4-d]pyrimidin-2-yl)phenoxy)-N-(tert-pentyl)acetamide

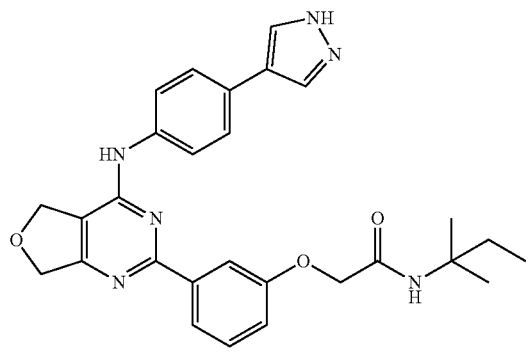 [SMILES: CCC(C)(C)NC(=O)COc1cccc(-c2nc3c(c(Nc4ccc(-c5cn[nH]c5)cc4)n2)COC3)c1]

Example 31A 2-chloro-N-(tert-pentyl)acetamide

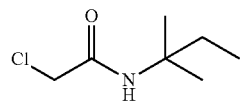

To a mixture of 2-methylbutan-2-amine (1.39 g, 15.94 mmol, 1.85 mL) and TEA (2.69 g, 26.56 mmol, 3.68 mL) in CH$_2$Cl$_2$ (30.00 mL) was added 2-chloroacetyl chloride (1.50 g, 13.28 mmol, 1.06 mL) dropwise at 0° C. The mixture was stirred at 23° C. for 2 h. The mixture was diluted with CH$_2$Cl$_2$ (30 mL) and washed with water (40 mL×2), citric acid (10%, 40 mL×2), NaHCO$_3$ (40 mL×2), brine (40 mL×2). The organic layer was dried over Na$_2$SO$_4$, filtered and concentrated under reduced pressure to give the title compound (1.96 g, crude) as yellow solid which was used in the next step reaction without further purification. $^1$H NMR (400 MHz, DMSO-$d_6$) δ 7.62 (s, 1H), 3.96 (s, 2H), 1.66-1.61 (m, 2H), 1.20 (s, 6H), 0.77 (t, J=7.6 Hz, 3H).

Example 31B

N-(tert-pentyl)-2-(3-(4,4,5,5-tetramethyl-1,3,2-dioxaborolan-2-yl)phenoxy)acetamide

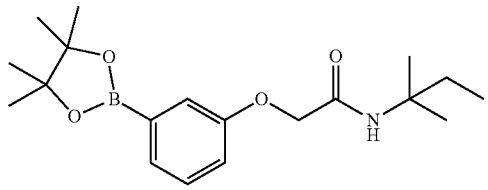 [SMILES: CCC(C)(C)NC(=O)COc1cccc(B2OC(C)(C)C(C)(C)O2)c1]

To the mixture of 2-chloro-N-(tert-pentyl)acetamide (800.00 mg, 4.89 mmol) and 3-(4,4,5,5-tetramethyl-1,3,2-dioxaborolan-2-yl)phenol (896.51 mg, 4.07 mmol) in MeCN (20.00 mL) was added $K_2CO_3$ (1.13 g, 8.15 mmol). The mixture was stirred at 70° C. for 16 h. TLC (petroleum ether/EtOAc=2:1, Rf=0.78) detected one new main spot. The reaction mixture was cooled to room temperature and diluted with water (30 mL). The mixture was extracted with EtOAc (30 mL×3). The combined organic layers were dried over $Na_2SO_4$, filtered and concentrated under reduced pressure to give a residue. The residue was purified by column chromatography ($SiO_2$, petroleum ether/EtOAc=1:1 to 8:1) to give the title compound (892 mg) as a yellow oil. $^1$H NMR (400 MHz, DMSO-$d_6$) δ 7.30-7.26 (m, 2H), 7.17-7.16 (m, 1H), 7.09-7.07 (m, 2H), 4.42 (s, 2H), 1.28-1.27 (m, 12H), 1.23 (s, 3H), 1.20 (s, 3H), 0.77 (t, J=7.4 Hz, 3H).

Example 31C tert-butyl (4-(1H-pyrazol-4-yl)phenyl)(2-(3-(2-oxo-2-(tert-pentylamino)ethoxy)phenyl)-5,7-dihydrofuro[3,4-d]pyrimidin-4-yl)carbamate

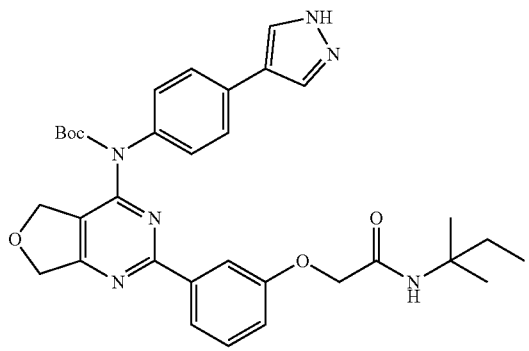 [SMILES: CCC(C)(C)NC(=O)COc1cccc(-c2nc3c(c(N(C(=O)OC(C)(C)C)c4ccc(-c5cn[nH]c5)cc4)n2)COC3)c1]

To the mixture of N-(tert-pentyl)-2-(3-(4,4,5,5-tetramethyl-1,3,2-dioxaborolan-2-yl)phenoxy)acetamide (150.00 mg, 431.95 umol) and tert-butyl 4-(4-((tert-butoxycarbonyl)(2-chloro-5,7-dihydrofuro[3,4-d]pyrimidin-4-yl)amino)phenyl)-1H-pyrazole-1-carboxylate (201.83 mg, 392.68 umol) in dioxane (4.00 mL), $H_2O$ (400.00 uL) was added $K_2CO_3$ (108.55 mg, 785.36 umol) and Pd(dppf)$Cl_2$ (28.73 mg, 39.27 umol). The mixture was stirred under $N_2$ at 100° C. for 16 h. TLC (petroleum ether/EtOAc=1:1, Rf=0.34, 0.76) detected two main spots. The reaction mixture was cooled to room temperature and diluted with (20 mL). The resulting mixture was extracted with EtOAc (30 mL×3). The combined organic layers were dried over $Na_2SO_4$, filtered and concentrated under reduced pressure to give a residue. The residue was purified by prep-TLC (petroleum ether/EtOAc=1:1) to give the title compound (68.00 mg, mono-Boc product: 48 mg) as a white solid.

Example 31D 2-(3-(4-((4-(1H-pyrazol-4-yl)phenyl)amino)-5,7-dihydrofuro[3,4-d]pyrimidin-2-yl)phenoxy)-N-(tert-pentyl)acetamide

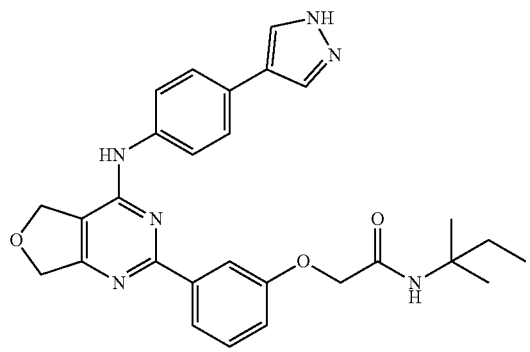 [SMILES: CCC(C)(C)NC(=O)COc1cccc(-c2nc3c(c(Nc4ccc(-c5cn[nH]c5)cc4)n2)COC3)c1]

To a mixture of tert-butyl (4-(1H-pyrazol-4-yl)phenyl)(2-(3-(2-oxo-2-(tert-pentylamino)ethoxy)phenyl)-5,7-dihydrofuro[3,4-d]pyrimidin-4-yl)carbamate (68.00 mg, 48 mg mono-Boc product was used together) in DMF (5.00 mL) and $CH_2Cl_2$ (1.00 mL) was added TFA (15.40 g, 135.06 mmol, 10.00 mL). The mixture was stirred at 25° C. for 16 h. LCMS showed about 34% of desired product and 51% of mono-Boc starting material. The mixture was concentrated under reduced pressure to remove $CH_2Cl_2$. The solution was diluted with sat.NaHCO$_3$ (30 mL) and extracted with EtOAc (30 mL×3). The organic layers were dried over $Na_2SO_4$, filtered and concentrated under reduced pressure to give a residue. The residue was purified by prep-HPLC (FA conditions) to give the title compound (6.8 mg) as a light yellow solid. $^1$H NMR (400 MHz, DMSO-$d_6$) δ 12.93 (s, 1H), 9.24 (s, 1H), 8.04-7.92 (m, 4H), 7.80 (d, J=8.4 Hz, 2H), 7.65 (d, J=8.0 Hz, 2H), 7.43-7.35 (m, 2H), 7.07 (d, J=7.2 Hz, 1H), 5.07 (s, 2H), 4.93 (s, 2H), 4.50 (s, 2H), 1.67-1.64 (m, 2H), 1.23 (s, 6H), 0.75 (t, J=7.2 Hz, 3H). (ES+) m/e 499.2 (M+H)$^+$.

Example 32

2-(3-(4-((4-(1H-pyrazol-4-yl)phenyl)amino)-5,7-dihydrofuro[3,4-d]pyrimidin-2-yl)phenoxy)-N-(3,3-difluorocyclobutyl)acetamide

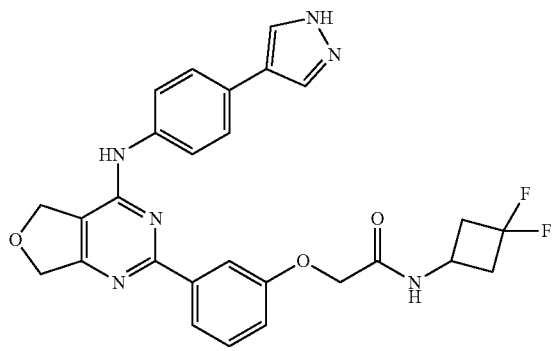 [SMILES: O=C(COc1cccc(-c2nc3c(c(Nc4ccc(-c5cn[nH]c5)cc4)n2)COC3)c1)NC1CC(F)(F)C1]

Example 32A 2-chloro-N-(3,3-difluorocyclobutyl)acetamide

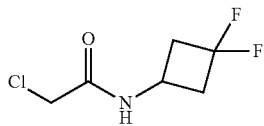 [SMILES: O=C(CCl)NC1CC(F)(F)C1]

To a mixture of 3,3-difluorocyclobutanamine (340.00 mg, 2.37 mmol, HCl) and TEA (456.80 mg, 4.51 mmol, 625.75 uL) in $CH_2Cl_2$ (15.00 mL) was added dropwise 2-chloroacetyl chloride (254.92 mg, 2.26 mmol, 179.52 uL) at 0° C. under $N_2$. The mixture was stirred at 23° C. for 2 h, diluted with $CH_2Cl_2$ (30 mL), and washed with water (40 mL×2), citric acid (10%, 40 mL×2), $NaHCO_3$ (40 mL×2), brine (40 mL×2). The organic layer was dried over $Na_2SO_4$, filtered and concentrated under reduced pressure to give the title compound (318 mg, crude) as a yellow solid and used in the next step reaction without further purification. $^1$H NMR (400 MHz, DMSO-$d_6$) δ 7.62 (s, 1H), 3.96 (s, 2H), 1.66-1.61 (m, 2H), 1.20 (s, 6H), 0.77 (t, J=7.6 Hz, 3H).

Example 32B

N-(3,3-difluorocyclobutyl)-2-(3-(4,4,5,5-tetramethyl-1,3,2-dioxaborolan-2-yl)phenoxy)acetamide

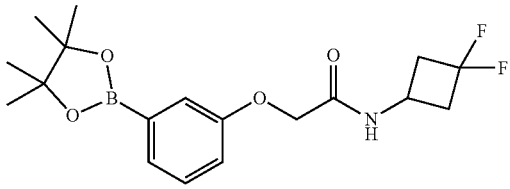 [SMILES: CC1(C)OB(c2cccc(OCC(=O)NC3CC(F)(F)C3)c2)OC1(C)C]

To a mixture of 2-chloro-N-(3,3-difluorocyclobutyl)acetamide (318.00 mg, 1.73 mmol) and 3-(4,4,5,5-tetramethyl-1,3,2-dioxaborolan-2-yl)phenol (380.72 mg, 1.73 mmol) in MeCN (15.00 mL) was added $K_2CO_3$ (478.21 mg, 3.46 mmol). The mixture was stirred at 70° C. for 15 h. TLC (petroleum ether/EtOAc=2:1, Rf=0.68) detected one new main spot. The reaction mixture was cooled to room temperature and diluted with water (40 mL). The resulting mixture was extracted with EtOAc (40 mL×3). The combined organic layers were dried over $Na_2SO_4$, filtered and concentrated under reduced pressure to give a residue. The residue was purified by column chromatography ($SiO_2$, petroleum ether/EtOAc=1:0 to 5:1) to give the title compound (172 mg, 12%) as a white solid. $^1$H NMR (400 MHz, DMSO-$d_6$) δ 7.30-7.26 (m, 2H), 7.17-7.16 (m, 1H), 7.09-7.07 (m, 2H), 4.42 (s, 2H), 1.28-1.27 (m, 12H), 1.23 (s, 3H), 1.20 (s, 3H), 0.77 (t, J=7.4 Hz, 3H).

Example 32C tert-butyl 4-(4-((tert-butoxycarbonyl)(2-(3-(2-((3,3-difluorocyclobutyl)amino)-2-oxoethoxy)phenyl)-5,7-dihydrofuro[3,4-d]pyrimidin-4-yl)amino)phenyl)-1H-pyrazole-1-carboxylate

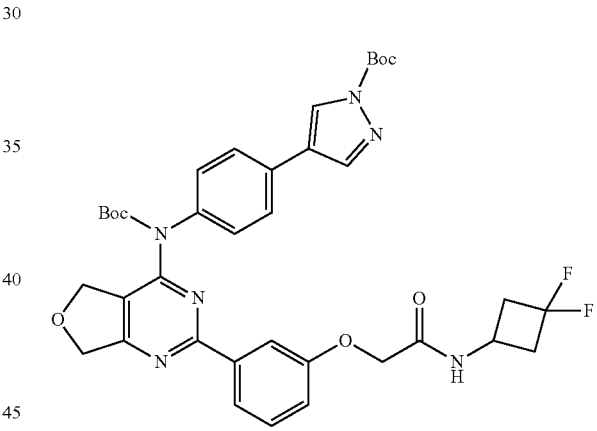

To the mixture of N-(3,3-difluorocyclobutyl)-2-(3-(4,4,5,5-tetramethyl-1,3,2-dioxaborolan-2-yl)phenoxy)acetamide (150.00 mg, 408.50 umol) and tert-butyl 4-(4-((tert-butoxycarbonyl)(2-chloro-5,7-dihydrofuro[3,4-d]pyrimidin-4-yl)amino)phenyl)-1H-pyrazole-1-carboxylate (174.96 mg, 340.42 umol) in dioxane (4.00 mL), $H_2O$ (400.00 uL) was added $K_2CO_3$ (94.10 mg, 680.83 umol) and Pd(dppf)$Cl_2$ (24.91 mg, 34.04 umol). The mixture was stirred under $N_2$ at 100° C. for 15 h. TLC (petroleum ether/EtOAc=1:1, Rf=0.30, 0.76) detected two new main spots. The reaction mixture was cooled to room temperature and diluted with water (30 mL). The resulting mixture was extracted with EtOAc (30 mL×3). The combined organic layers were dried over $Na_2SO_4$, filtered and concentrated under reduced pressure to give a residue. The residue was purified by prep-TLC (petroleum ether/EtOAc=1:1) to give the title compound (62.00 mg, mono-Boc product: 30 mg) all as a light yellow solid.

Example 32D 2-(3-(4-((4-(1H-pyrazol-4-yl)phenyl)amino)-5,7-dihydrofuro[3,4-d]pyrimidin-2-yl)phenoxy)-N-(3,3-difluorocyclobutyl)acetamide

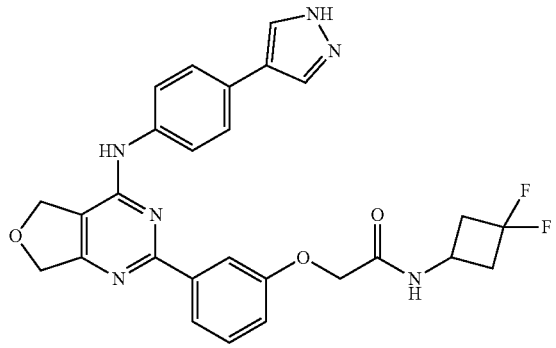 [SMILES: O=C(COc1cccc(-c2nc3c(c(Nc4ccc(-c5cn[nH]c5)cc4)n2)COC3)c1)NC1CC(F)(F)C1]

To a mixture of tert-butyl 4-(4-((tert-butoxycarbonyl)(2-(3-(2-((3,3-difluorocyclobutyl)amino)-2-oxoethoxy)phenyl)-5,7-dihydrofuro[3,4-d]pyrimidin-4-yl)amino)phenyl)-1H-pyrazole-1-carboxylate (62.00 mg, 13 mg mono-Boc product was used together) in CH$_2$Cl$_2$ (4.00 mL) was added HCl/dioxane (4 M, 8.00 mL). The mixture was stirred at 23° C. for 2 h. LCMS showed mono-Boc starting material was the major product. The mixture was stirred at 30° C. for another 2 h. LCMS showed that mono-Boc starting material remained and no peak of desired product formed. The mixture was concentrated under reduced pressure to give a residue. The residue was dissolved with CH$_2$Cl$_2$ (6 mL) and HCl/dioxane (8 mL) was added. The mixture was stirred at 30° C. for 3.5 h. LCMS showed about 33% of desired product and 35% of starting material. The mixture was concentrated under reduced pressure to give a residue. The residue was purified by prep-HPLC (FA conditions) to give the title compound (4.8 mg) as a light yellow solid. $^1$H NMR (400 MHz, DMSO-d$_6$) δ 12.93 (s, 1H), 9.27 (s, 1H), 8.67 (d, J=7.2 Hz, 1H), 8.45 (s, 1H), 7.98-7.96 (m, 4H), 7.80 (d, J=8.4 Hz, 2H), 7.65 (d, J=8.4 Hz, 2H), 7.44 (t, J=8.0 Hz, 1H), 7.12-7.09 (m, 1H), 5.07 (s, 2H), 4.94 (s, 2H), 4.58 (s, 2H), 4.21-4.17 (m, 1H), 2.88-2.84 (m, 2H), 2.75-2.69 (m, 2H). (ES+) m/e 519.1 (M+H)$^+$.

Example 33

2-(3-(4-((4-(1H-pyrazol-4-yl)phenyl)amino)-5,7-dihydrofuro[3,4-d]pyrimidin-2-yl)phenoxy)-N-(2,2,2-trifluoroethyl)acetamide

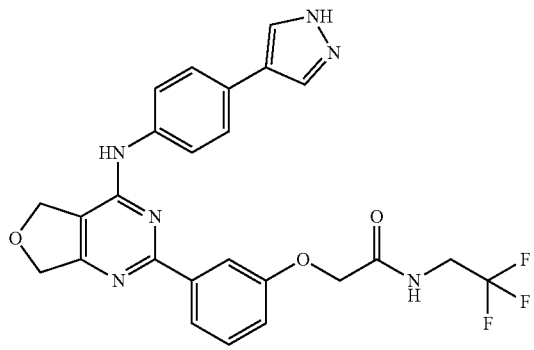 [SMILES: O=C(COc1cccc(-c2nc3c(c(Nc4ccc(-c5cn[nH]c5)cc4)n2)COC3)c1)NCC(F)(F)F]

Example 33A 2-chloro-N-(2,2,2-trifluoroethyl)acetamide

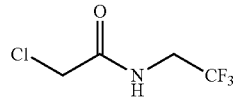

To a mixture of 2,2,2-trifluoroethanamine (1.58 g, 15.94 mmol, 1.25 mL) and TEA (2.69 g, 26.56 mmol, 3.68 mL, 2.00 eq) in CH$_2$Cl$_2$ (20.00 mL) was added dropwise 2-chloroacetyl chloride (1.50 g, 13.28 mmol, 1.06 mL) at 0° C. under N$_2$. The mixture was stirred at 23° C. for 2 h. The mixture was diluted with CH$_2$Cl$_2$ (30 mL) and washed with water (40 mL×2), citric acid (10%, 40 mL×2), NaHCO$_3$ (40 mL×2), brine (40 mL×2). The organic layer was dried over Na$_2$SO$_4$, filtered and concentrated under reduced pressure to give the title compound (780 mg, crude) as a yellow solid which was used for the next step reaction without further purification. $^1$H NMR (400 MHz, DMSO-d$_6$) δ 8.89 (s, 1H), 4.16 (s, 2H), 3.99-3.92 (m, 2H).

Example 33B 2-(3-(4,4,5,5-tetramethyl-1,3,2-dioxaborolan-2-yl)phenoxy)-N-(2,2,2-trifluoroethyl)acetamide

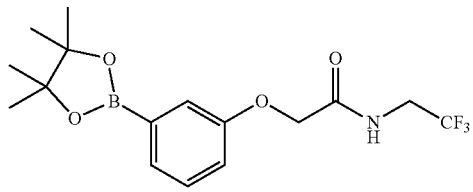 [SMILES: CC1(C)OB(c2cccc(OCC(=O)NCC(F)(F)F)c2)OC1(C)C]

To a mixture of 2-chloro-N-(2,2,2-trifluoroethyl)acetamide (500.00 mg, 2.85 mmol) and 3-(4,4,5,5-tetramethyl-1,3,2-dioxaborolan-2-yl)phenol (569.85 mg, 2.59 mmol) in MeCN (15.00 mL) was added K$_2$CO$_3$ (716.18 mg, 5.18 mmol). The mixture was stirred at 70° C. for 16 h. TLC (petroleum ether/EtOAc=2:1, Rf=0.68) detected one new main spot. The reaction mixture was cooled to room temperature and diluted with water (30 mL) and extracted with EtOAc (30 mL×3). The combined organic layers were dried over Na$_2$SO$_4$, filtered and concentrated under reduced pressure to give a residue. The residue was purified by column chromatography (SiO$_2$, petroleum ether/EtOAc=1:0 to 8:1) to give the title compound (728 mg, 62%) as a yellow solid. $^1$H NMR (400 MHz, DMSO-d$_6$) δ 8.79-8.76 (m, 1H), 7.34-7.24 (m, 3H), 7.09 (d, J=2.4 Hz, 1H), 4.59 (s, 2H), 3.94-3.93 (m, 2H), 1.28 (s, 12H).

Example 33C tert-butyl 4-(4-((tert-butoxycarbonyl)(2-(3-(2-oxo-2-((2,2,2-trifluoroethyl)amino)ethoxy)phenyl)-5,7-dihydrofuro[3,4-d]pyrimidin-4-yl)amino)phenyl)-1H-pyrazole-1-carboxylate

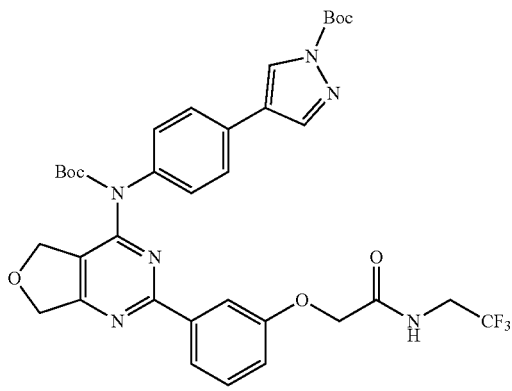 [SMILES: CC(C)(C)OC(=O)N(c1ccc(-c2cnn(C(=O)OC(C)(C)C)c2)cc1)c1nc(-c2cccc(OCC(=O)NCC(F)(F)F)c2)nc2c1COC2]

To the mixture of 2-(3-(4,4,5,5-tetramethyl-1,3,2-dioxaborolan-2-yl)phenoxy)-N-(2,2,2-trifluoroethyl)acetamide (150.00 mg, 417.65 umol) and tert-butyl 4-(4-((tert-butoxycarbonyl)(2-chloro-5,7-dihydrofuro[3,4-d]pyrimidin-4-yl)amino)phenyl)-1H-pyrazole-1-carboxylate (178.88 mg, 348.04 umol) in dioxane (4.00 mL), H$_2$O (400.00 uL) was added K$_2$CO$_3$ (96.21 mg, 696.08 umol) and Pd(dppf)Cl$_2$ (25.47 mg, 34.80 umol). The mixture was stirred under N$_2$ at 100° C. for 16 h. TLC (petroleum ether/EtOAc=1:1, Rf=0.32, 0.76) showed two main spots. The reaction mixture was cooled to room temperature and diluted with (30 mL). The resulting mixture was extracted with EtOAc (30 mL×3). The combined organic layers were dried over Na$_2$SO$_4$, filtered and concentrated under reduced pressure to give a residue. The residue was purified by prep-TLC (petroleum ether/EtOAc=1:1) to give the title compound (71.00 mg, mono-Boc product: 36 mg) all as a light yellow solid.

Example 33D 2-(3-(4-((4-(1H-pyrazol-4-yl)phenyl)amino)-5,7-dihydrofuro[3,4-d]pyrimidin-2-yl)phenoxy)-N-(2,2,2-trifluoroethyl)acetamide

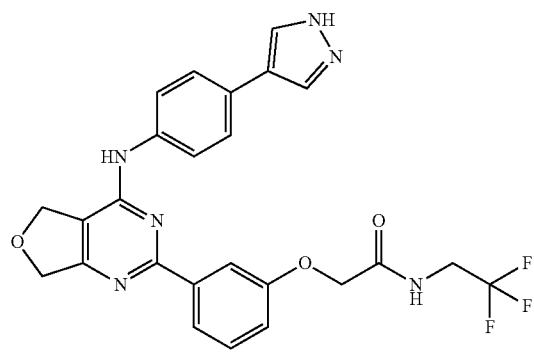 [SMILES: O=C(COc1cccc(-c2nc3c(c(Nc4ccc(-c5cn[nH]c5)cc4)n2)COC3)c1)NCC(F)(F)F]

To a mixture of tert-butyl 4-(4-((tert-butoxycarbonyl)(2-(3-(2-oxo-2-((2,2,2-trifluoroethyl)amino)ethoxy)phenyl)-5,7-dihydrofuro[3,4-d]pyrimidin-4-yl)amino)phenyl)-1H-pyrazole-1-carboxylate (71.00 mg, 36 mg mono-Boc product was used together) in CH$_2$Cl$_2$ (4.00 mL) was added HCl/dioxane (4 M, 8.00 mL). The mixture was stirred at 23° C. for 2 h. LCMS showed about 25% of desired product and 63% of mono-Boc starting material. The mixture was stirred at 30° C. for another 2 h. LCMS showed about 26% of desired product and 58% of mono-Boc starting material. The mixture was stirred at 30° C. for 3.5 h. LCMS showed about 43% of desired product and 47% of mono-Boc starting material. The mixture was concentrated under reduced pressure to give a residue. The residue was purified by prep-HPLC (FA conditions) to afford the title compound (19.3 mg) as a yellow solid. $^1$H NMR (400 MHz, DMSO-d$_6$) δ 8.34 (s, 2H), 7.85-7.84 (m, 2H), 7.81-7.75 (m, 4H), 7.59 (d, J=8.2 Hz, 1H), 7.38 (d, J=7.2 Hz, 1H), 5.22-5.15 (m, 4H), 4.73 (s, 2H), 4.02-3.95 (m, 2H). (ES+) m/e 511.1 (M+H)$^+$.

Example 34

2-(3-(4-((4-(1H-pyrazol-4-yl)phenyl)amino)-5,7-dihydrothieno[3,4-d]pyrimidin-2-yl)phenoxy)-N-isopropylacetamide

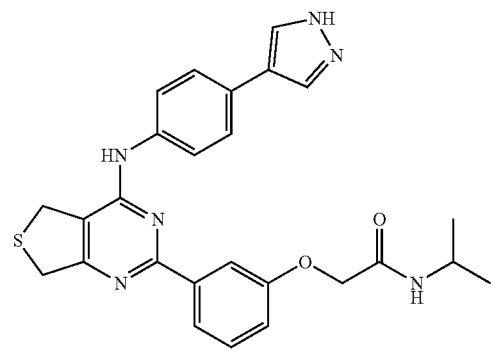 [SMILES: CC(C)NC(=O)COc1cccc(-c2nc3c(c(Nc4ccc(-c5cn[nH]c5)cc4)n2)CSC3)c1]

Example 34A 1-(tetrahydro-2H-pyran-2-yl)-4-(4,4,5,5-tetramethyl-1,3,2-dioxaborolan-2-yl)-1H-pyrazole

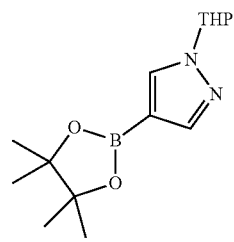

To a solution of 4-(4,4,5,5-tetramethyl-1,3,2-dioxaborolan-2-yl)-1H-pyrazole (10.00 g, 51.54 mmol) in CH$_2$Cl$_2$ (100.00 mL) was added DHP (8.67 g, 103.08 mmol, 9.42 mL) and TsOH.H$_2$O (4.90 g, 25.77 mmol). The mixture was stirred at 30° C. for 4 hour. LCMS showed 4-(4,4,5,5-tetramethyl-1,3,2-dioxaborolan-2-yl)-1H-pyrazole was consumed completely and one main peak with desired mass was detected. The reaction mixture was concentrated under reduced pressure to remove solvent. The residue was diluted with sat.NaHCO₃ (35 mL) and the mixture was extracted with EtOAc (100 mL). The organic layer was dried over Na₂SO₄, filtered and concentrated under reduced pressure to give a residue. The residue was purified by column chromatography (SiO₂, Petroleum ether/Ethyl acetate=20/1 to 1/1) to afford the title compound (10.5 g, 73%) as colorless oil. ¹H NMR (400 MHz, DMSO-d₆) δ 8.06 (s, 1H), 7.62 (s, 1H), 5.44-5.41 (m, 1H), 3.94-3.89 (m, 1H), 3.76-3.58 (m, 2H), 3.46-3.41 (m, 1H), 2.15-2.06 (m, 1H), 1.95-1.84 (m, 2H), 1.76-1.40 (m, 9H), 1.26 (s, 12H).

Example 34B 4-(1-(tetrahydro-2H-pyran-2-yl)-1H-pyrazol-4-yl) aniline

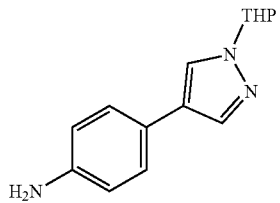

A mixture of 1-(tetrahydro-2H-pyran-2-yl)-4-(4,4,5,5-tetramethyl-1,3,2-dioxaborolan-2-yl)-1H-pyrazole (9.50 g, 34.15 mmol), 4-bromoaniline (5.58 g, 32.45 mmol), K₂CO₃ (9.44 g, 68.31 mmol) and Pd(dppf)Cl₂ (1.25 g, 1.71 mmol) in dioxane (100.00 mL)/H₂O (10.00 mL) was degassed and purged with N₂ 3 times, then the mixture was stirred at 100° C. for 16 hour under N₂ atmosphere. TLC (Petroleum ether/Ethyl acetate=1/1) showed starting materials were consumed completely, and there was a new spot (Rf=0.15). The reaction mixture was cooled to room temperature. After addition of water (200 mL) and EtOAc (200 mL), the mixture was stirred for 5 min. The resulting suspension was filtered through celatom, and the filtrate collected. The aqueous layer was extracted with EtOAc (200 mL×2). The combined organic layers were washed with brine (100 mL×2), dried over Na₂SO₄, filtered and concentrated to give a residue. The residue was purified by column chromatography (SiO₂, Petroleum ether/Ethyl acetate=1/0 to 1/2) to afford the title compound (7.5 g, 90%) as an off-white solid.

Example 34C 2,4-dichloro-5,7-dihydrothieno[3,4-d]pyrimidine

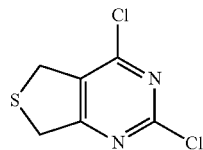 [SMILES: Clc1nc(Cl)c2c(n1)CSC2]

A mixture of 5,7-dihydrothieno[3,4-d]pyrimidine-2,4-diol (700.00 mg, 4.11 mmol) and DIPEA (1.06 g, 8.23 mmol, 1.44 mL) in POCl₃ (13.20 g, 86.09 mmol, 8.00 mL) was stirred at 80° C. for 2 hour under N₂ atmosphere. TLC (Petroleum ether/Ethyl acetate=5/1) showed starting materials were consumed completely, and there was a new spot (Rf=0.8) forming. The mixture was concentrated under reduced pressure to give a residue. And then ice water (30 mL) was poured into the residue. The resulting mixture was extracted with EtOAc (30 mL×2). The combined organic layers was washed with sat.NaHCO₃ (20 mL×2), dried over Na₂SO₄, filtered and concentrated to give the crude title compound (600 mg, 71%) as black brown oil.

Example 34E 2-chloro-N-(4-(1-(tetrahydro-2H-pyran-2-yl)-1H-pyrazol-4-yl)phenyl)-5,7-dihydrothieno[3,4-d]pyrimidin-4-amine

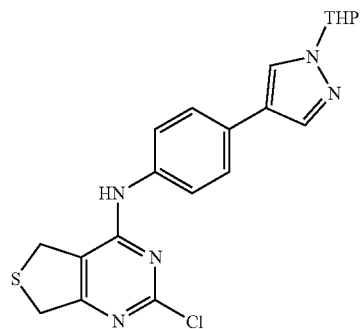

A mixture of 2,4-dichloro-5,7-dihydrothieno[3,4-d]pyrimidine (600.00 mg, 2.90 mmol), 4-(1-(tetrahydro-2H-pyran-2-yl)-1H-pyrazol-4-yl)aniline (704.94 mg, 2.90 mmol) and DIPEA (748.93 mg, 5.79 mmol, 1.01 mL) in n-BuOH (10.00 mL) was stirred at 100° C. for 16 hours under N₂ atmosphere. LCMS showed 2,4-dichloro-5,7-dihydrothieno[3,4-d]pyrimidine was consumed completely and 90% of desired product was detected. The reaction mixture was concentrated under reduced pressure to remove n-BuOH. The residue was purified by column chromatography (SiO₂, Petroleum ether/Ethyl acetate=10/1 to 1/1) to afford the title compound (1.05 g, 87%) as a yellow solid.

Example 34F

N-isopropyl-2-(3-(4-((4-(1-(tetrahydro-2H-pyran-2-yl)-1H-pyrazol-4-yl)phenyl)amino)-5,7-dihydrothieno[3,4-d]pyrimidin-2-yl)phenoxy)acetamide

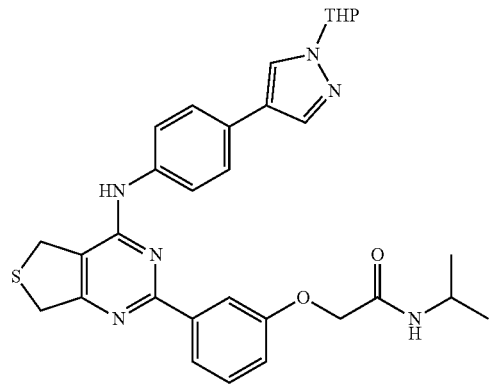

A mixture of 2-chloro-N-(4-(1-(tetrahydro-2H-pyran-2-yl)-1H-pyrazol-4-yl)phenyl)-5,7-dihydrothieno[3,4-d]pyrimidin-4-amine (210.00 mg, 507.34 umol), N-isopropyl-2-(3-(4,4,5,5-tetramethyl-1,3,2-dioxaborolan-2-yl)phenoxy)acetamide (161.94 mg, 507.34 umol), Pd(dppf)Cl$_2$ (37.12 mg, 50.73 umol) and K$_2$CO$_3$ (140.24 mg, 1.01 mmol) in dioxane (10.00 mL)/H$_2$O (1.00 mL) was degassed and purged with N$_2$ 3 times, and then the mixture was stirred at 95° C. for 16 hour under N$_2$ atmosphere. LCMS showed 2-chloro-N-(4-(1-(tetrahydro-2H-pyran-2-yl)-1H-pyrazol-4-yl)phenyl)-5,7-dihydrothieno[3,4-d]pyrimidin-4-amine was consumed completely and one new main peak with desired mass was detected. The reaction mixture was quenched by addition H$_2$O (30 mL) at 25° C. and the resulting mixture was extracted with EtOAc (30 mL×3). The combined organic layers were washed with brine (30 mL×3), dried over Na$_2$SO$_4$, filtered and concentrated under reduced pressure to give a residue. The residue was purified by prep-TLC (SiO$_2$, Petroleum ether/Ethyl acetate=1:2, Rf=0.35) to afford the title compound (120 mg) as a yellow solid.

Example 34G 2-(3-(4-((4-(1H-pyrazol-4-yl)phenyl)amino)-5,7-dihydrothieno[3,4-d]pyrimidin-2-yl)phenoxy)-N-isopropylacetamide

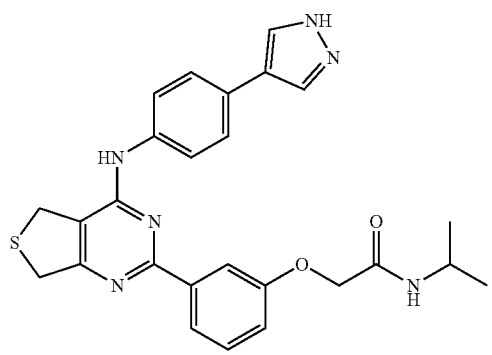 [SMILES: CC(C)NC(=O)COc1cccc(-c2nc3c(c(Nc4ccc(-c5cn[nH]c5)cc4)n2)CSC3)c1]

To a solution of N-isopropyl-2-(3-(4-((4-(1-(tetrahydro-2H-pyran-2-yl)-1H-pyrazol-4-yl)phenyl)amino)-5,7-dihydrothieno[3,4-d]pyrimidin-2-yl)phenoxy)acetamide (120.00 mg, 210.26 umol) in CH$_2$Cl$_2$ (1.00 mL) was added HCl/dioxane (4 M, 2.00 mL). The mixture was stirred at 25° C. for 16 hour. LCMS showed N-isopropyl-2-(3-(4-((4-(1-(tetrahydro-2H-pyran-2-yl)-1H-pyrazol-4-yl)phenyl)amino)-5,7-dihydrothieno[3,4-d]pyrimidin-2-yl)phenoxy)acetamide was consumed completely and a new main peak with the desired mass was detected. The reaction mixture was concentrated under reduced pressure to give a residue. The residue was purified by prep-HPLC (FA conditions). The title compound (10.4 mg) was obtained by lyophilization as an off-white solid. $^1$H NMR (400 MHz, DMSO-d$_6$) δ 12.92 (s, 1H), 8.98 (s, 1H), 8.48 (s, 1H), 8.19 (s, 1H), 8.00-7.93 (m, 4H), 7.83 (d, J=8.4 Hz, 2H), 7.67 (d, J=8.4 Hz, 2H), 7.42 (t, J=8.0 Hz, 1H), 7.09 (dd, J=7.6, 1.6 Hz, 1H), 4.52 (s, 2H), 4.25-4.24 (m, 4H), 4.03-3.95 (m, 1H), 1.10 (d, J=6.4 Hz, 3H). (ES+) m/e 487.3 (M+H)$^+$.

Example 35

2-(3-(4-((4-(1H-pyrazol-4-yl)phenyl)amino)-5,7-dihydrothieno[3,4-d]pyrimidin-2-yl)phenoxy)-N-cyclobutylacetamide

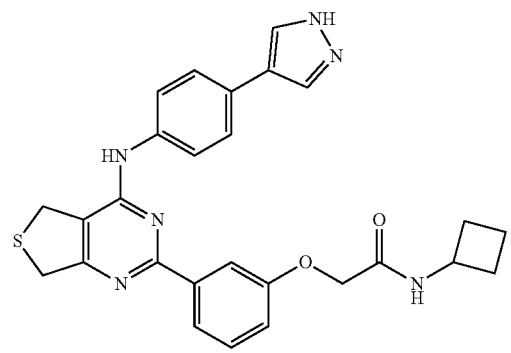

Example 35A

N-cyclobutyl-2-(3-(4-((4-(1-(tetrahydro-2H-pyran-2-yl)-1H-pyrazol-4-yl)phenyl)amino)-5,7-dihydrothieno[3,4-d]pyrimidin-2-yl)phenoxy)acetamide

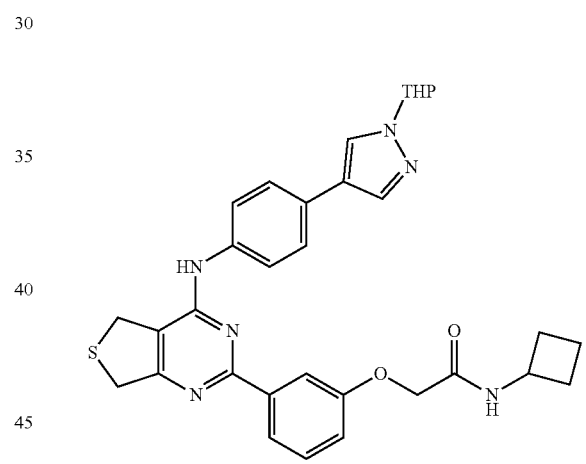

A mixture of 2-chloro-N-(4-(1-(tetrahydro-2H-pyran-2-yl)-1H-pyrazol-4-yl)phenyl)-5,7-dihydrothieno[3,4-d]pyrimidin-4-amine (200.00 mg, 483.19 umol), N-cyclobutyl-2-(3-(4,4,5,5-tetramethyl-1,3,2-dioxaborolan-2-yl)phenoxy)acetamide (160.04 mg, 483.19 umol), Pd(dppf)Cl$_2$ (35.36 mg, 48.32 umo) and K$_2$CO$_3$ (133.56 mg, 966.38 umol) in dioxane (5.00 mL)/H$_2$O (500.00 uL) was degassed and purged with N$_2$ 3 times, then the mixture was stirred at 95° C. for 16 hour under N$_2$ atmosphere. LCMS showed 2-chloro-N-(4-(1-(tetrahydro-2H-pyran-2-yl)-1H-pyrazol-4-yl)phenyl)-5,7-dihydrothieno[3,4-d]pyrimidin-4-amine was consumed completely and ~76% peak with desired mass was detected. The reaction mixture was cooled to room temperature and quenched by addition H$_2$O (30 mL) at 25° C., then the resulting mixture was extracted with EtOAc (30 mL×3). The combined organic layers were washed with brine (30 mL×3), dried over Na$_2$SO$_4$, filtered and concentrated under reduced pressure to give a residue. The residue was purified by prep-TLC (SiO$_2$, Petroleum ether/Ethyl acetate=1:2, Rf=0.35) to afford the title compound (75 mg, 27%; LCMS: EW3123-109-P1C) as an off-white solid.

Example 35B 2-(3-(4-((4-(1H-pyrazol-4-yl)phenyl)amino)-5,7-dihydrothieno[3,4-d]pyrimidin-2-yl)phenoxy)-N-cyclobutylacetamide

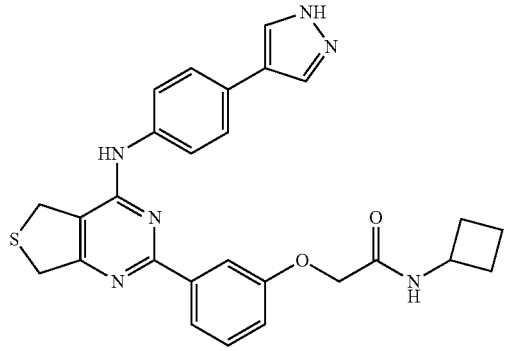

To a solution of N-cyclobutyl-2-(3-(4-((4-(1-(tetrahydro-2H-pyran-2-yl)-1H-pyrazol-4-yl)phenyl)amino)-5,7-dihydrothieno[3,4-d]pyrimidin-2-yl)phenoxy)acetamide (75.00 mg, 128.71 umol) in CH$_2$Cl$_2$ (2.00 mL) was added HCl/dioxane (4 M, 4.00 mL). The mixture was stirred at 25° C. for 16 hour. LCMS showed ~65% peak with desired mass. The reaction mixture was concentrated under reduced pressure to give a residue. The residue was purified by prep-HPLC (FA conditions). The product of EW3123-99 was combined with the product of this page and residual MeCN was removed under reduced pressure. The title compound (12.7 mg) was obtained by lyophilization as an off-white solid. $^1$H NMR (400 MHz, DMSO-d$_6$) δ 8.98 (s, 1H), 8.40 (d, J=7.6 Hz, 2H), 8.07 (s, 2H), 7.95-7.93 (m, 2H), 7.82 (d, J=8.4 Hz, 2H), 7.66 (d, J=8.4 Hz, 2H), 7.42 (t, J=8.0 Hz, 1H), 7.10-7.07 (m, 1H), 4.51 (s, 2H), 4.32-4.23 (m, 5H), 2.14-2.00 (m, 4H), 1.63-1.60 (m, 2H). (ES+) m/e 499.3 (M+H)$^+$.

Example 36

2-(3-(4-((4-(1H-pyrazol-4-yl)phenyl)amino)-5,7-dihydrothieno[3,4-d]pyrimidin-2-yl)phenoxy)-N-cyclopentylacetamide

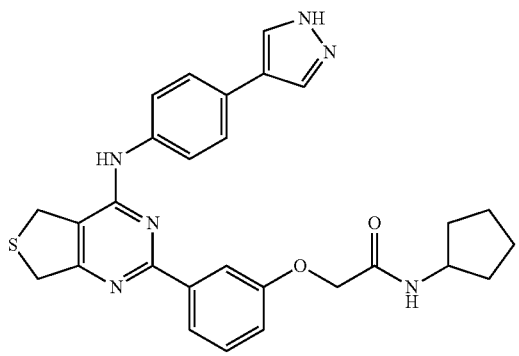 [SMILES: O=C(COc1cccc(-c2nc3c(c(Nc4ccc(-c5cn[nH]c5)cc4)n2)CSC3)c1)NC1CCCC1]

Example 36A

N-cyclopentyl-2-(3-(4-((4-(1-(tetrahydro-2H-pyran-2-yl)-1H-pyrazol-4-yl)phenyl)amino)-5,7-dihydrothieno[3,4-d]pyrimidin-2-yl)phenoxy)acetamide

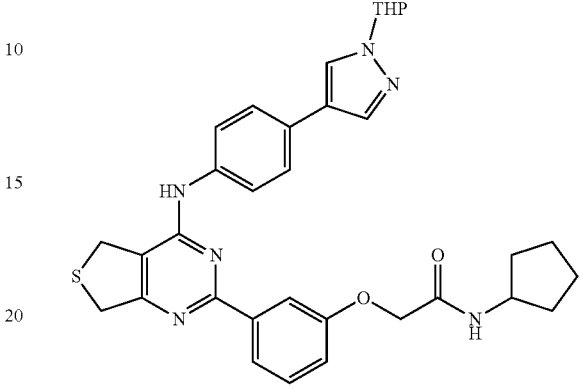

A mixture of 2-chloro-N-(4-(1-(tetrahydro-2H-pyran-2-yl)-1H-pyrazol-4-yl)phenyl)-5,7-dihydrothieno[3,4-d]pyrimidin-4-amine (200.00 mg, 483.19 umol), N-cyclopentyl-2-(3-(4,4,5,5-tetramethyl-1,3,2-dioxaborolan-2-yl)phenoxy)acetamide (166.81 mg, 483.19 umol), Pd(dppf)Cl$_2$ (35.36 mg, 48.32 umol), K$_2$CO$_3$ (133.56 mg, 966.38 umol) in dioxane (5.00 mL)/H$_2$O (500.00 uL) was degassed and purged with N$_2$ 3 times and the mixture was stirred at 95° C. for 16 hour under N$_2$ atmosphere. LCMS showed 2-chloro-N-(4-(1-(tetrahydro-2H-pyran-2-yl)-1H-pyrazol-4-yl)phenyl)-5,7-dihydrothieno[3,4-d]pyrimidin-4-amine was consumed completely and ~63% peak with desired product was detected. The reaction mixture was cooled to room temperature and quenched by addition H$_2$O (30 mL) and the resulting mixture was extracted with EtOAc (30 mL×3). The combined organic layers were washed with brine (30 mL×3), dried over Na$_2$SO$_4$, filtered and concentrated under reduced pressure to give a residue. The residue was purified by prep-TLC (SiO$_2$, Petroleum ether/Ethyl acetate=1:2, Rf=0.35) to afford the title compound (70.00 mg, 24%) as an off-white solid.

Example 36B 2-(3-(4-((4-(1H-pyrazol-4-yl)phenyl)amino)-5,7-dihydrothieno[3,4-d]pyrimidin-2-yl)phenoxy)-N-cyclopentylacetamide

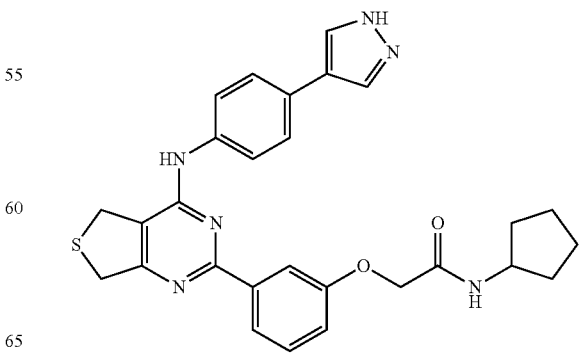

To a solution of N-cyclopentyl-2-(3-(4-((4-(1-(tetrahydro-2H-pyran-2-yl)-1H-pyrazol-4-yl)phenyl)amino)-5,7-dihydrothieno[3,4-d]pyrimidin-2-yl)phenoxy)acetamide (65.00 mg, 108.93 umol) in CH₂Cl₂ (2.00 mL) was added HCl/dioxane (4 M, 4.00 mL). The mixture was stirred at 25° C. for 16 hour. LCMS showed N-cyclopentyl-2-(3-(4-((4-(1-(tetrahydro-2H-pyran-2-yl)-1H-pyrazol-4-yl)phenyl)amino)-5,7-dihydrothieno[3,4-d]pyrimidin-2-yl)phenoxy)acetamide was consumed completely and ~52% peak with desired mass was detected. The reaction mixture was concentrated under reduced pressure to give a residue. The residue was purified by prep-HPLC (FA conditions). The product of EW3123-100 was combined with this page. The residual acetonitrile after prep-HPLC separation was removed under reduced pressure. The title compound (10.9 mg) was obtained by lyophilization as off-white solid. ¹H NMR (400 MHz, DMSO-d₆) δ 8.98 (s, 1H), 8.42 (s, 2H), 8.07 (d, J=7.2 Hz, 2H), 7.95-7.93 (m, 2H), 7.82 (d, J=8.8 Hz, 2H), 7.67 (d, J=8.4 Hz, 2H), 7.42 (t, J=8.0 Hz, 1H), 7.10-7.08 (m, 1H), 4.53 (s, 2H), 4.25-4.24 (m, 4H), 4.12-4.10 (m, 1H), 1.81-1.80 (m, 2H), 1.63-1.62 (m, 2H), 1.51-1.46 (m, 4H). (ES+) m/e 513.3 (M+H)⁺.

Example 37

2-(3-(4-((4-(1H-pyrazol-4-yl)phenyl)amino)-6-methyl-5,6,7,8-tetrahydropyrido[4,3-d]pyrimidin-2-yl)phenoxy)-N-(tert-butyl)acetamide

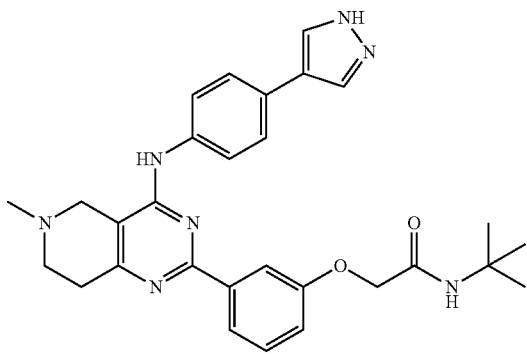 [SMILES: CN1CCc2nc(-c3cccc(OCC(=O)NC(C)(C)C)c3)nc(Nc3ccc(-c4cn[nH]c4)cc3)c2C1]

To the mixture of 2-(3-(4-((4-(1H-pyrazol-4-yl)phenyl)amino)-5,6,7,8-tetrahydropyrido[4,3-d]pyrimidin-2-yl)phenoxy)-N-(tert-butyl)acetamide (200.00 mg, 374.50 umol, HCl salt) in MeOH (2.00 mL) was added TEA (75.79 mg, 748.99 umol, 103.82 uL). The mixture was stirred at 15° C. for 10 min. Then to the mixture was added HCHO (84.35 mg, 1.12 mmol, 77.38 uL, 40% purity), HOAc (89.95 mg, 1.50 mmol, 85.67 uL). The mixture was stirred at 15° C. for 20 min. Then to the mixture was added NaBH₃CN (117.67 mg, 1.87 mmol). The resulting mixture was stirred at 15° C. for 15.5 h. LCMS showed one main peak of desired product. The reaction mixture was diluted with water (30 mL) and the mixture was extracted with EtOAc (30 mL×3). The combined organic layers were dried over Na₂SO₄, filtered and concentrated under reduced pressure to give a residue. The residue was purified by prep-HPLC (FA conditions) to afford the title compound (74.4 mg, 32%) as a light yellow solid. ¹H NMR (400 MHz, DMSO-d₆) δ 8.44 (s, 1H), 8.20 (s, 1H), 8.05 (s, 2H), 7.95-7.90 (m, 3H), 7.78 (d, J=8.8 Hz, 2H), 7.38 (t, J=8.2 Hz, 1H), 7.06-7.04 (m, 1H), 4.50 (s, 2H), 4.02-3.94 (m, 1H), 3.50 (s, 2H), 2.83 (d, J=5.2 Hz, 2H), 2.73 (d, J=5.2 Hz, 2H), 2.47 (s, 3H), 1.09 (d, J=6.4 Hz, 6H). (ES+) m/e 512.2 (M+H)⁺.

Example 38

2-(3-(4-((4-(1H-pyrazol-4-yl)phenyl)amino)-6-methyl-5,6,7,8-tetrahydropyrido[4,3-d]pyrimidin-2-yl)phenoxy)-N-(pentan-3-yl)acetamide

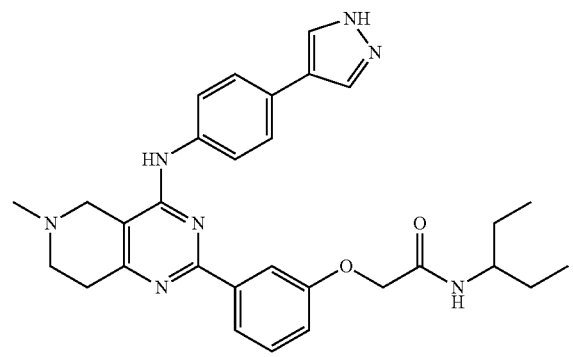 [SMILES: CCC(CC)NC(=O)COc1cccc(-c2nc3c(c(Nc4ccc(-c5cn[nH]c5)cc4)n2)CN(C)CC3)c1]

The title compound was synthesized using essentially the same procedure as described for the synthesis of Example 37.

Yellow solid; Yield: 11% (3 steps). ¹H NMR (400 MHz, DMSO-d₆) δ 8.43 (s, 1H), 8.25 (s, 1H), 8.04 (s, 2H), 7.91-7.90 (m, 2H), 7.79-7.72 (m, 3H), 7.63 (d, J=8.4 Hz, 2H), 7.38 (t, J=8.2 Hz, 1H), 7.06-7.03 (m, 1H), 4.56 (s, 2H), 3.64-3.60 (m, 1H), 3.50 (s, 2H), 2.82 (d, J=5.2 Hz, 2H), 2.73 (d, J=5.2 Hz, 2H), 2.47 (s, 3H), 1.48-1.34 (m, 4H), 0.77 (t, J=7.4 Hz, 6H). (ES+) m/e 526.4 (M+H)⁺.

Example 39

2-(3-(4-((4-(1H-pyrazol-4-yl)phenyl)amino)-6-methyl-5,6,7,8-tetrahydropyrido[4,3-d]pyrimidin-2-yl)phenoxy)-N-isopropylacetamide

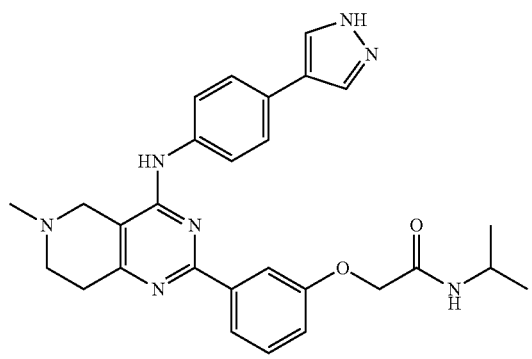 [SMILES: CC(C)NC(=O)COc1cccc(-c2nc3c(c(Nc4ccc(-c5cn[nH]c5)cc4)n2)CN(C)CC3)c1]

The title compound was synthesized using essentially the same procedure as described for the synthesis of Example 37.

Light Yellow solid; Yield: 19% (3 steps). ¹H NMR (400 MHz, DMSO-d₆) δ 8.44 (s, 1H), 8.20 (s, 1H), 8.05 (s, 2H), 7.95-7.90 (m, 3H), 7.78 (d, J=8.8 Hz, 2H), 7.38 (t, J=8.2 Hz, 1H), 7.06-7.04 (m, 1H), 4.50 (s, 2H), 4.02-3.94 (m, 1H), 3.50 (s, 2H), 2.83 (d, J=5.2 Hz, 2H), 2.73 (d, J=5.2 Hz, 2H), 2.47 (s, 3H), 1.09 (d, J=6.4 Hz, 6H). (ES+) m/e 498.3 (M+H)+.

Example 40

2-(3-(4-((4-(1H-pyrazol-4-yl)phenyl)amino)-7,8-dihydro-5H-pyrano[4,3-d]pyrimidin-2-yl)phenoxy)-N-isopropylacetamide

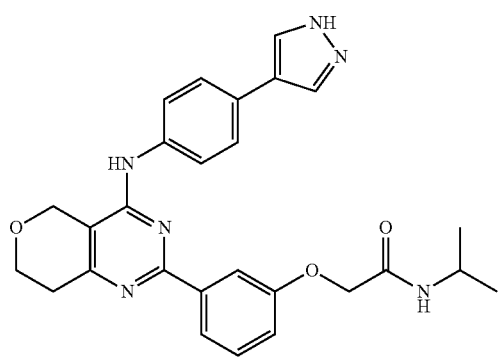 [SMILES: CC(C)NC(=O)COc1cccc(-c2nc3c(c(Nc4ccc(-c5cn[nH]c5)cc4)n2)COCC3)c1]

Example 40A methyl 4-oxotetrahydro-2H-pyran-3-carboxylate

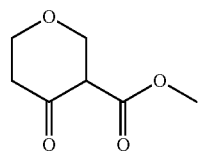

To the mixture of tetrahydro-4H-pyran-4-one (15.00 g, 149.82 mmol), dimethyl carbonate (33.74 g, 374.55 mmol) in THF (300.00 mL) was added NaH (14.98 g, 374.55 mmol, 60% purity) by portions at 0° C. The mixture was stirred under N₂ at 0° C. for 30 min, then at 15° C. for 30 min. Then the mixture was warmed to 45° C. and stirred for 15 h. TLC (petroleum ether/EtOAc=3:1, Rf=0.6) showed one new main spot. The reaction mixture was poured into the mixture of icy 1 N HCl (600 mL) and extracted with EtOAc (600 mL×3). The combined organic layers were washed with brine (800 mL×2), dried over Na₂SO₄, filtered and concentrated under reduced pressure to give a residue. The residue was purified by column chromatography (SiO₂, petroleum ether/EtOAc=1:0 to 10:1) to afford the title compound (7.75 g 33%) as colorless oil. ¹H NMR (400 MHz, DMSO-d₆) δ 11.78 (s, 1H), 4.14-4.10 (m, 1H), 4.07-3.95 (m, 1H), 3.86 (t, J=5.6 Hz, 2H), 3.78-3.77 (m, 3H), 2.40 (t, J=5.6 Hz, 2H).

Example 40B 2-(ethylthio)-7,8-dihydro-5H-pyrano[4,3-d]pyrimidin-4-ol

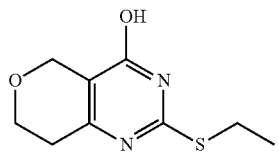

To the mixture of 2-ethylisothiourea (9.07 g, 49.00 mmol, HBr salt) in H₂O (50.00 mL) under dark was added Na₂CO₃ (5.19 g, 49.00 mmol). Then to the mixture was added methyl 4-oxotetrahydro-2H-pyran-3-carboxylate (7.75 g, 49.00 mmol). The mixture was stirred under dark at 25° C. for 16 h TLC (petroleum ether/EtOAc=1:1, Rf=0.3) showed one new main spot. The mixture was filtered, the solid was washed with water (30 mL), petroleum ether/EtOAc=20:1 (20 mL). Then the solid was dried under reduced pressure to afford the title compound (8.01 g, crude) as an off-white solid. ¹H NMR (400 MHz, DMSO-d₆) δ 10.69 (s, 1H), 5.87 (s, 1H), 3.83 (s, 1H), 3.63-3.49 (m, 3H), 3.00-2.89 (m, 2H), 2.40 (s, 1H), 1.24 (t, J=7.2 Hz, 3H).

Example 40C 7,8-dihydro-5H-pyrano[4,3-d]pyrimidine-2,4-diol

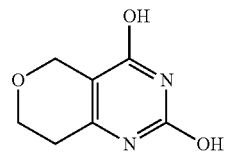 [SMILES: Oc1nc(O)c2c(n1)CCOC2]

To the mixture of 2-(ethylthio)-7,8-dihydro-5H-pyrano[4,3-d]pyrimidin-4-ol (8.01 g, 37.73 mmol) in H₂O (100.00 mL) was added conc.HCl (3.82 g, 37.73 mmol, 3.75 mL), AcOH (13.60 g, 226.38 mmol, 12.95 mL). The mixture was stirred at 100° C. for 16 h. The mixture was cooled to room temperature and filtered. The solid was washed with water (80 mL), dried over with toluene to affort the title compound (5.30 g, crude) as a white solid. ¹H NMR (400 MHz, DMSO-d₆) δ 10.99 (s, 1H), 10.85 (s, 1H), 4.19 (s, 2H), 3.77 (t, J=5.2 Hz, 2H), 2.38 (t, J=5.0 Hz, 2H).

Example 40D 2,4-dichloro-7,8-dihydro-5H-pyrano[4,3-d]pyrimidine

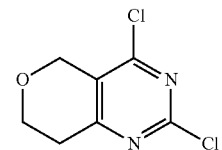 [SMILES: Clc1nc(Cl)c2c(n1)CCOC2]

To POCl₃ (50.00 mL) was added 7,8-dihydro-5H-pyrano[4,3-d]pyrimidine-2,4-diol (4.80 g, 28.55 mmol), DIPEA (7.38 g, 57.10 mmol, 9.97 mL). The mixture was stirred under N₂ at 80° C. for 16 h. TLC (petroleum ether/EtOAc=3:1, Rf=0.55) showed one main spot was detected. The mixture was concentrated under reduced pressure to remove most of POCl₃ to give a residue. With the addition of ice, the residue was neutralized with sat.NaHCO₃ to pH-7 and the resulting mixture was extracted with EtOAc (100 mL×3). The combined organic layers were dried over Na₂SO₄, filtered and concentrated under reduced pressure to give a residue. The residue was purified by column chromatography (SiO₂, petroleum ether/EtOAc=10:1 to 3:1) to give the title compound (5.10 g, 87%) as a light yellow solid.

Example 40E 2-chloro-N-(4-(1-(tetrahydro-2H-pyran-2-yl)-1H-pyrazol-4-yl)phenyl)-7,8-dihydro-5H-pyrano[4,3-d]pyrimidin-4-amine

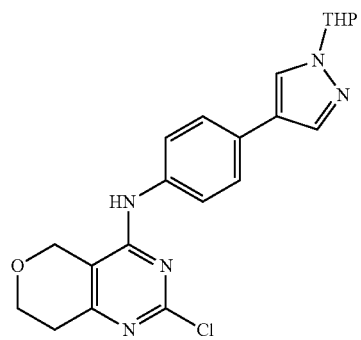

To the mixture of 2,4-dichloro-7,8-dihydro-5H-pyrano[4,3-d]pyrimidine (5.10 g, 24.87 mmol) and 4-(1-(tetrahydro-2H-pyran-2-yl)-1H-pyrazol-4-yl)aniline (6.05 g, 24.87 mmol) in n-BuOH (40.00 mL) was added DIPEA (6.43 g, 49.74 mmol, 8.69 mL). The mixture was stirred under N₂ at 100° C. for 16 h. TLC (petroleum ether/EtOAc=1:2, Rf=0.46) showed one main spot was detected. The mixture was cooled to room temperature and filtered. The solid was purified by recrystallization (petroleum ether/EtOAc=10:1, 200 mL) to give the title compound (4.93 g) as a light yellow solid. ¹H NMR (400 MHz, DMSO-d₆) δ 8.71 (s, 1H), 8.31 (s, 1H), 7.93 (s, 1H), 7.62-7.55 (m, 4H), 5.42-5.39 (m, 1H), 4.61 (s, 2H), 3.95-3.91 (m, 3H), 3.68-3.61 (m, 1H), 2.71 (t, J=5.2 Hz, 2H), 2.14-2.07 (m, 1H), 1.95-1.94 (m, 2H), 1.71-1.66 (m, 1H), 1.56-1.55 (m, 1H).

Example 40F 2-(3-(4-((4-(1H-pyrazol-4-yl)phenyl)amino)-7,8-dihydro-5H-pyrano[4,3-d]pyrimidin-2-yl)phenoxy)-N-isopropylacetamide

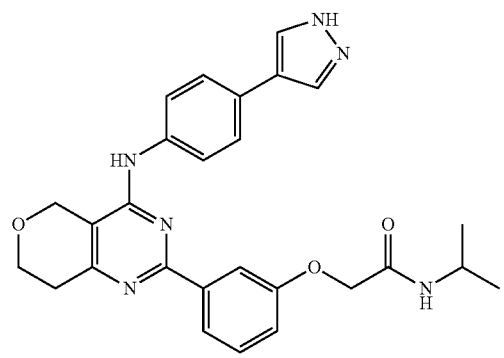 [SMILES: CC(C)NC(=O)COc1cccc(-c2nc3c(c(Nc4ccc(-c5cn[nH]c5)cc4)n2)COCC3)c1]

To the mixture of 2-chloro-N-(4-(1-(tetrahydro-2H-pyran-2-yl)-1H-pyrazol-4-yl)phenyl)-7,8-dihydro-5H-pyrano[4,3-d]pyrimidin-4-amine (1.00 eq) and N-isopropyl-2-(3-(4,4,5,5-tetramethyl-1,3,2-dioxaborolan-2-yl)phenoxy)acetamide (1.20 eq) in dioxane (3.00 mL), H₂O (300.00 uL) was added K₂CO₃ (2.00 eq) and Pd(dppf)Cl₂ (0.10 eq). The mixture was stirred under N₂ at 90° C. for 16 h. The reaction mixture was cooled to room temperature and diluted with water. The resulting mixture was extracted with EtOAc. The combined organic layers were washed with brine, dried over Na₂SO₄, filtered and concentrated under reduced pressure to give a residue. The residue was purified by column chromatography to afford N-isopropyl-2-(3-(4-((4-(1-(tetrahydro-2H-pyran-2-yl)-1H-pyrazol-4-yl)phenyl)amino)-7,8-dihydro-5H-pyrano[4,3-d]pyrimidin-2-yl)phenoxy)acetamide.

To the mixture of N-isopropyl-2-(3-(4-((4-(1-(tetrahydro-2H-pyran-2-yl)-1H-pyrazol-4-yl)phenyl)amino)-7,8-dihydro-5H-pyrano[4,3-d]pyrimidin-2-yl)phenoxy)acetamide (1.00 eq) in CH₂Cl₂ was added HCl/dioxane. The mixture was stirred at 15° C. for 0.5-16 h. The mixture was concentrated under reduced pressure to give a residue. The residue was purified by prep-HPLC (FA conditions) to afford the title compound. Yellow solid; Yield: 23% (2 steps). ¹H NMR (400 MHz, DMSO-d₆) δ 8.42 (s, 1H), 8.06 (s, 2H), 7.97 (d, J=8.0 Hz, 1H), 7.91 (d, J=7.2 Hz, 2H), 7.76 (d, J=8.8 Hz, 2H), 7.64 (d, J=8.4 Hz, 2H), 7.39 (t, J=8.2 Hz, 1H), 7.07-7.04 (m, 1H), 4.71 (s, 2H), 4.50 (s, 2H), 4.01-3.96 (m, 3H), 2.82 (t, J=5.0 Hz, 2H), 1.09 (d, J=6.8 Hz, 6H). (ES+) m/e 485.1 (M+H)⁺.

Example 41

2-(3-(4-((4-(1H-pyrazol-4-yl)phenyl)amino)-7,8-dihydro-5H-pyrano[4,3-d]pyrimidin-2-yl)phenoxy)-N-(sec-butyl)acetamide

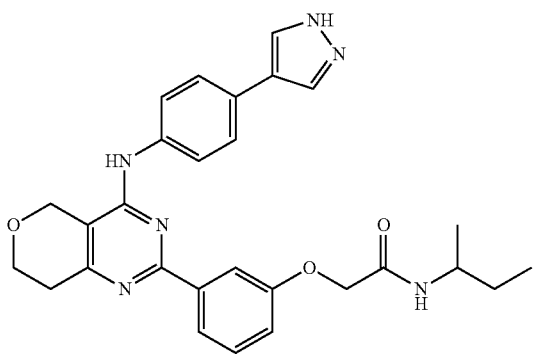 [SMILES: CCC(C)NC(=O)COc1cccc(-c2nc3c(c(Nc4ccc(-c5cn[nH]c5)cc4)n2)COCC3)c1]

The compound was synthesized using essentially the same procedure described for the synthesis of Example 40.

Yellow solid; Yield: 13% (2 steps). $^1$H NMR (400 MHz, DMSO-$d_6$) δ 12.77 (s, 1H), 8.40 (s, 1H), 8.05 (s, 2H), 7.92-7.86 (m, 3H), 7.75 (d, J=8.4 Hz, 2H), 7.39 (t, J=8.2 Hz, 1H), 7.07-7.04 (m, 1H), 4.71 (s, 2H), 4.53 (s, 2H), 3.99 (t, J=5.4 Hz, 2H), 3.80-3.77 (m, 1H), 2.82 (d, J=4.8 Hz, 2H), 1.44-1.40 (m, 2H), 1.05 (d, J=6.8 Hz, 3H), 0.78 (t, J=7.4 Hz, 3H). (ES+) m/e 499.1 (M+H)$^+$.

Example 42

2-(3-(4-((4-(1H-pyrazol-4-yl)phenyl)amino)thieno[3,2-d]pyrimidin-2-yl)phenoxy)-N-(tert-butyl)acetamide

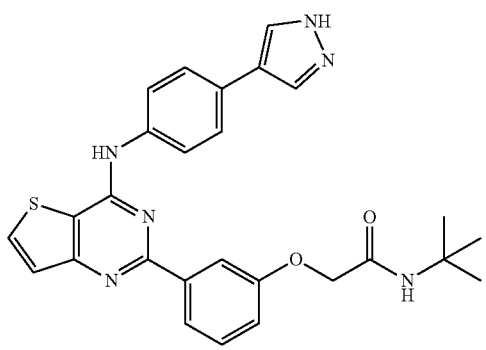 [SMILES: CC(C)(C)NC(=O)COc1cccc(-c2nc(Nc3ccc(-c4cn[nH]c4)cc3)c3sccc3n2)c1]

To the mixture of 2-chloro-N-(4-(1-(tetrahydro-2H-pyran-2-yl)-1H-pyrazol-4-yl)phenyl)thieno[3,2-d]pyrimidin-4-amine (1.00 eq) and N-(tert-butyl)-2-(3-(4,4,5,5-tetramethyl-1,3,2-dioxaborolan-2-yl)phenoxy)acetamide (1.20 eq) in dioxane (5.00 mL), H$_2$O (500.00 uL) was added K$_2$CO$_3$ (2.00 eq), Pd(dppf)Cl$_2$ (0.10 eq). The mixture was stirred under N$_2$ at 90° C. for 16 h. The reaction mixture was cooled to room temperature and diluted with water. The resulting mixture was extracted with EtOAc. The combined organic layers were washed with brine, dried over Na$_2$SO$_4$, filtered and concentrated under reduced pressure to give a residue. The residue was purified by column chromatography to afford N-(tert-butyl)-2-(3-(4-((4-(1-(tetrahydro-2H-pyran-2-yl)-1H-pyrazol-4-yl)phenyl)amino)thieno[3,2-d]pyrimidin-2-yl)phenoxy)acetamide.

To the mixture of N-(tert-butyl)-2-(3-(4-((4-(1-(tetrahydro-2H-pyran-2-yl)-1H-pyrazol-4-yl)phenyl)amino) thieno[3,2-d]pyrimidin-2-yl)phenoxy)acetamide (1.00 eq) in CH$_2$Cl$_2$ (5.00 mL) was added HCl/dioxane (4 M, 5.00 mL). The mixture was stirred at 20° C. for 0.5 h. The mixture was concentrated under reduced pressure to give a residue. The residue was purified by prep-HPLC (FA conditions) to provide the title compound. $^1$H NMR (400 MHz, DMSO-$d_6$) δ 9.82 (s, 1H), 8.26 (d, J=5.2 Hz, 1H), 8.08-8.02 (m, 4H), 7.89 (d, J=8.4 Hz, 2H), 7.69 (d, J=8.4 Hz, 2H), 7.56 (s, 1H), 7.52 (d, J=5.2 Hz, 1H), 7.43 (t, J=7.4 Hz, 1H), 7.08-7.06 (m, 1H), 4.50 (s, 2H), 1.31 (s, 9H). (ES+) m/e 499.2 (M+H)$^+$.

Example 43

2-(3-(4-((4-(1H-pyrazol-4-yl)phenyl)amino)thieno[3,2-d]pyrimidin-2-yl)phenoxy)-N-(tert-pentyl)acetamide

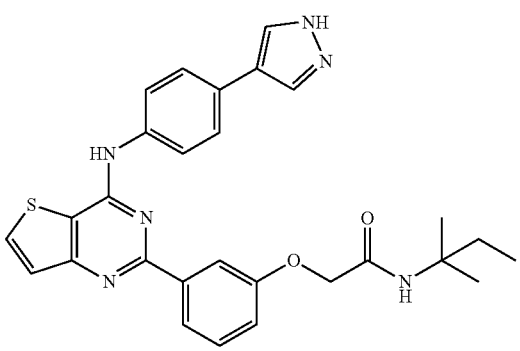 [SMILES: CCC(C)(C)NC(=O)COc1cccc(-c2nc(Nc3ccc(-c4cn[nH]c4)cc3)c3sccc3n2)c1]

The compound was synthesized using essentially the same procedure described for the synthesis of Example 42.

Yellow solid; Yield: 8.8% (2 steps). $^1$H NMR (400 MHz, DMSO-$d_6$) δ 9.82 (s, 1H), 8.26 (d, J=5.2 Hz, 1H), 8.08-8.02 (m, 4H), 7.89 (d, J=8.4 Hz, 2H), 7.68 (d, J=8.4 Hz, 2H), 7.52 (d, J=5.6 Hz, 1H), 7.45-7.38 (m, 2H), 7.08-7.05 (m, 1H), 4.52 (s, 2H), 1.70-1.65 (m, 2H), 1.24 (s, 6H), 0.76 (t, J=7.4 Hz, 3H). (ES+) m/e 513.2 (M+H)$^+$.

Example 44

2-(3-(4-((4-(1H-pyrazol-4-yl)phenyl)amino)-6-acetyl-5,6,7,8-tetrahydropyrido[4,3-d]pyrimidin-2-yl)phenoxy)-N-isopropylacetamide

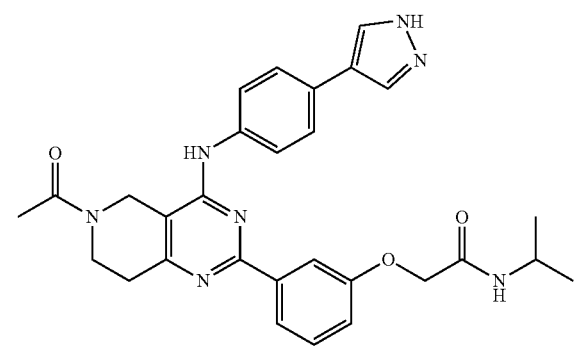 [SMILES: CC(=O)N1CCc2nc(-c3cccc(OCC(=O)NC(C)C)c3)nc(Nc3ccc(-c4cn[nH]c4)cc3)c2C1]

To the mixture of acetic acid (20.79 mg, 346.14 umol, 19.80 uL), HATU (164.52 mg, 432.67 umol) and DIPEA (74.56 mg, 576.90 umol, 100.76 uL) in DMF (2 mL) was added the mixture of 2-(3-(4-((4-(1H-pyrazol-4-yl)phenyl)amino)-5,6,7,8-tetrahydropyrido[4,3-d]pyrimidin-2-yl)phenoxy)-N-isopropylacetamide (150.00 mg, 288.45 umol, HCl salt) and DIPEA (74.56 mg, 576.90 umol, 100.76 uL) in DMF (1 mL). The mixture was stirred at 25° C. for 16 h. LCMS showed one peak with desired mass and one peak of Ms+1=610. The reaction mixture was diluted with water (30 mL) and extracted with EtOAc (30 mL×3). The combined organic layers were washed with brine (40 mL×2), dried over Na$_2$SO$_4$, filtered and concentrated under reduced pressure to give a residue. The residue was dissolved with CH$_2$Cl$_2$ (5 mL) and HCl/dioxane (5 mL, 4 N) was added. The mixture was stirred at 25° C. for 0.5 h. LCMS showed one main peak of desired product. The mixture was concentrated under reduced pressure to give a residue. The residue was purified by prep-HPLC (FA conditions) to afford the title compound (34.5 mg, 22%) as a light yellow solid. $^1$H NMR (400 MHz, DMSO-d$_6$) δ 7.98-7.96 (m, 3H), 7.89-7.87 (m, 2H), 7.76-7.73 (m, 2H), 7.63 (t, J=9.4 Hz, 2H), 7.53 (s, 1H), 7.38 (t, J=7.8 Hz, 1H), 7.05 (d, J=8.0 Hz, 1H), 4.59 (s, 2H), 4.48 (s, 2H), 3.99-3.91 (m, 1H), 3.80-3.77 (m, 2H), 2.89 (s, 1H), 2.76 (s, 1H), 2.16 (d, J=11.2 Hz, 3H), 1.06 (d, J=6.8 Hz, 6H). (ES+) m/e 526.4 (M+H)$^+$.

Example 45

2-(3-(4-((4-(1H-pyrazol-4-yl)phenyl)amino)-6-acetyl-5,6,7,8-tetrahydropyrido[4,3-d]pyrimidin-2-yl)phenoxy)-N-(pentan-3-yl)acetamide

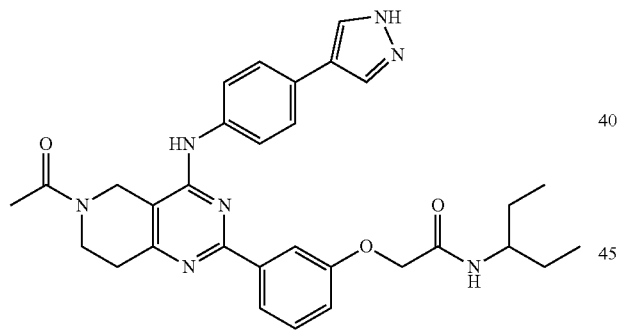

To the mixture of acetic acid (19.72 mg, 328.42 umol, 18.78 uL), HATU (156.09 mg, 410.52 umol) and DIPEA (70.74 mg, 547.36 umol, 95.59 uL) in DMF (2 mL) was added the mixture of 2-(3-(4-((4-(1H-pyrazol-4-yl)phenyl)amino)-5,6,7,8-tetrahydropyrido[4,3-d]pyrimidin-2-yl)phenoxy)-N-(pentan-3-yl)acetamide (150.00 mg, 273.68 umol, HCl salt) and DIPEA (70.74 mg, 547.36 umol, 95.59 uL) in DMF (1 mL). The mixture was stirred at 25° C. for 16 h. LCMS showed one peak with desired mass and one peak of Ms+1=638. The reaction mixture was diluted with water (30 mL) and the resulting mixture was extracted with EtOAc (30 mL×3). The combined organic layers were washed with brine (40 mL×2), dried over Na$_2$SO$_4$, filtered and concentrated under reduced pressure to give a residue. The residue was dissolved with CH$_2$Cl$_2$ (5 mL) and HCl/dioxane (5 mL, 4 N) was added. The mixture was stirred at 25° C. for 0.5 h. LCMS showed one main peak of desired product. The mixture was concentrated under reduced pressure to give a residue. The residue was purified by prep-HPLC (FA conditions) to afford the title compound (29.1 mg, 19%) as a light yellow solid. $^1$H NMR (400 MHz, DMSO-d$_6$) δ 8.46 (s, 1H), 7.97-7.92 (m, 4H), 7.79 (d, J=8.4 Hz, 2H), 7.61 (d, J=8.4 Hz, 2H), 7.40-7.36 (m, 2H), 7.08-7.06 (m, 1H), 4.64 (s, 2H), 4.54 (s, 2H), 3.83-3.80 (m, 2H), 3.68-3.63 (m, 1H), 2.88 (s, 2H), 2.18 (s, 3H), 1.51-1.38 (m, 4H), 0.81 (t, J=7.4 Hz, 6H). (ES+) m/e 554.1 (M+H)$^+$.

Example 46

2-(3-(4-((4-(1H-pyrazol-4-yl)phenyl)amino)-7,8-dihydro-5H-pyrano[4,3-d]pyrimidin-2-yl)phenoxy)-N-isobutylacetamide

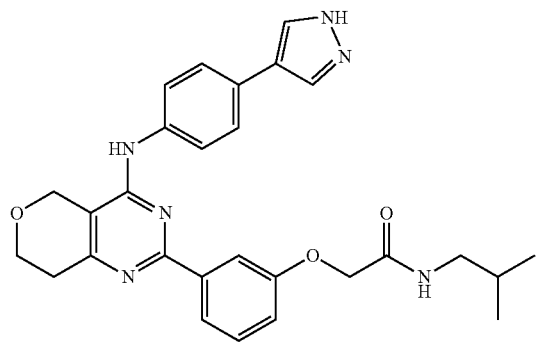 [SMILES: CC(C)CNC(=O)COc1cccc(-c2nc3c(c(Nc4ccc(-c5cn[nH]c5)cc4)n2)COCC3)c1]

The compound was synthesized using essentially the same procedure described for the synthesis of Example 40.
Light Yellow solid; Yield: 9.3% (2 steps). $^1$H NMR (400 MHz, DMSO-d$_6$) δ 12.90 (s, 1H), 8.40 (s, 1H), 8.14-8.05 (m, 3H), 7.92-7.90 (m, 2H), 7.75 (d, J=8.4 Hz, 2H), 7.63 (d, J=8.4 Hz, 2H), 7.39 (t, J=8.2 Hz, 1H), 7.07-7.05 (m, 1H), 4.71 (s, 2H), 4.55 (s, 2H), 3.99 (t, J=5.6 Hz, 2H), 2.96 (t, J=6.4 Hz, 2H), 2.82 (t, J=5.2 Hz, 2H), 1.78-1.70 (m, 1H), 0.80 (d, J=6.8 Hz, 6H). (ES+) m/e 499.2 (M+H)$^+$.

Example 47

2-(3-(4-((4-(1H-pyrazol-4-yl)phenyl)amino)-7,8-dihydro-5H-pyrano[4,3-d]pyrimidin-2-yl)phenoxy)-N-neopentylacetamide

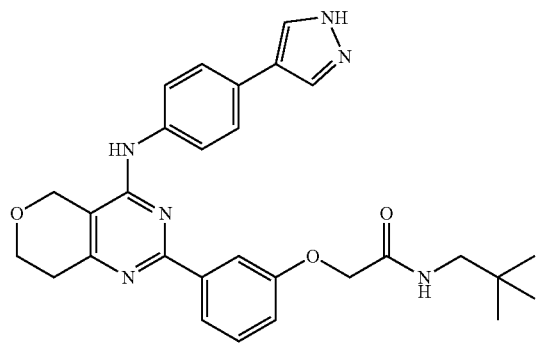 [SMILES: CC(C)(C)CNC(=O)COc1cccc(-c2nc3c(c(Nc4ccc(-c5cn[nH]c5)cc4)n2)COCC3)c1]

The compound was synthesized using essentially the same procedure described for the synthesis of Example 40.
Light Yellow solid; Yield: 39% (2 steps). $^1$H NMR (400 MHz, DMSO-d$_6$) δ 12.90 (s, 1H), 8.39 (s, 1H), 8.04-7.95 (m, 3H), 7.92-7.90 (m, 2H), 7.75 (d, J=8.4 Hz, 2H), 7.63 (d, J=8.8 Hz, 2H), 7.39 (t, J=8.2 Hz, 1H), 7.07-7.04 (m, 1H), 4.71 (s, 2H), 4.60 (s, 2H), 3.99 (t, J=5.6 Hz, 2H), 2.95 (d, J=6.4 Hz, 2H), 2.81 (t, J=5.2 Hz, 2H), 0.80 (s, 9H). (ES+) m/e 513.2 (M+H)+.

Example 48

2-(3-(4-((4-(1H-pyrazol-4-yl)phenyl)amino)-6-acetyl-5,6,7,8-tetrahydropyrido[4,3-d]pyrimidin-2-yl)phenoxy)-N-(tert-butyl)acetamide

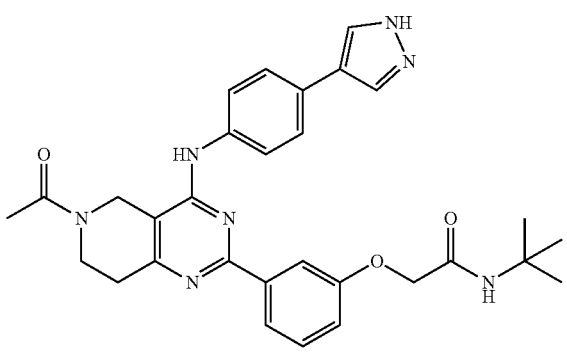 [SMILES: CC(=O)N1CCc2nc(-c3cccc(OCC(=O)NC(C)(C)C)c3)nc(Nc3ccc(-c4cn[nH]c4)cc3)c2C1]

To the mixture of acetic acid (13.49 mg, 224.70 umol, 12.85 uL), HATU (106.80 mg, 280.88 umol) and DIPEA (48.40 mg, 374.50 umol, 65.41 uL) in DMF (1 mL) was added the mixture of 2-(3-(4-((4-(1H-pyrazol-4-yl)phenyl)amino)-5,6,7,8-tetrahydropyrido[4,3-d]pyrimidin-2-yl)phenoxy)-N-(tert-butyl)acetamide (100.00 mg, 187.25 umol, HCl salt) and DIPEA (48.40 mg, 374.50 umol, 65.41 uL) in DMF (1 mL). The mixture was stirred at 15° C. for 16 h. LCMS showed two main peaks. The reaction mixture was diluted with water (30 mL) and extracted with EtOAc (30 mL×3). The combined organic layers were washed with brine (40 mL×2), dried over Na$_2$SO$_4$, filtered and concentrated under reduced pressure to give a residue. The residue was purified by prep-HPLC (FA conditions) to separate the two peaks. (1). HPLC and LCMS showed one peak was the mixture of desired product and THP-protected product. The solid after lyophilization was used into next step. To the solid in CH$_2$Cl$_2$ (2.00 mL) was added HCl/dioxane (4 N, 3.00 mL). The mixture was stirred at 25° C. for 1 h. LCMS showed one main peak of desired product. The mixture was concentrated under reduced pressure to give a residue (Part A). HPLC and LCMS showed the other peak was the mixture of desired product and bi-substituted product. The solid after lyophilization was used into next step. To the solid in THF (2.00 mL) and MeOH (2.00 mL) was added NaOH (2 M, 2.00 mL). The mixture was stirred at 25° C. for 1 h. LCMS showed one main peak of desired product. The reaction was diluted with water (20 mL) and the mixture was extracted with EtOAc (30 mL×3). The combined organic layers were dried over Na2SO4, filtered and concentrated under reduced pressure to give a residue (Part B). The residue which was combined with Part A was purified by prep-HPLC (FA conditions) to afford the title compound (11.6 mg) as a light yellow solid. $^1$H NMR (400 MHz, DMSO-d$_6$) δ 7.88-7.84 (m, 4H), 7.76-7.73 (m, 2H), 7.63 (t, J=9.6 Hz, 2H), 7.50-7.49 (m, 1H), 7.38 (t, J=8.0 Hz, 1H), 7.02 (d, J=6.4 Hz, 1H), 7.06-7.04 (m, 1H), 4.59 (s, 2H), 4.44 (s, 2H), 3.80-3.77 (m, 2H), 2.89 (s, 1H), 2.76 (s, 1H), 2.16 (d, J=11.2 Hz, 3H), 1.26 (s, 9H). (ES+) m/e 540.3 (M+H)+.

Example 49

2-(3-(4-((4-(1H-pyrazol-4-yl)phenyl)amino)-7,8-dihydro-5H-pyrano[4,3-d]pyrimidin-2-yl)phenoxy)-N-(pentan-3-yl)acetamide

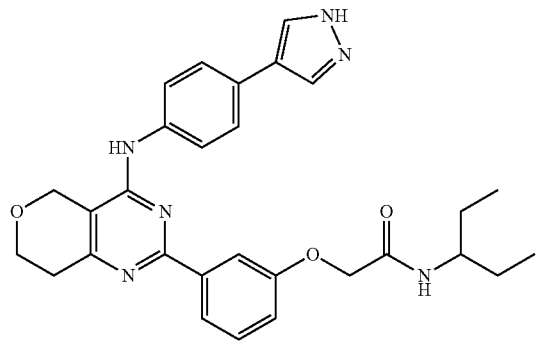 [SMILES: CCC(CC)NC(=O)COc1cccc(-c2nc3c(c(Nc4ccc(-c5cn[nH]c5)cc4)n2)COCC3)c1]

The compound was synthesized using essentially the same procedure described for the synthesis of Example 40.

Light Yellow solid; Yield: 13% (2 steps). $^1$H NMR (400 MHz, DMSO-d$_6$) δ 8.40 (s, 1H), 8.05 (s, 2H), 7.92-7.91 (m, 2H), 7.77-7.73 (m, 3H), 7.64 (d, J=8.4 Hz, 2H), 7.39 (t, J=8.2 Hz, 1H), 7.07-7.04 (m, 1H), 4.71 (s, 2H), 4.56 (s, 2H), 3.99 (t, J=5.4 Hz, 2H), 3.65-3.60 (m, 1H), 2.81 (s, 2H), 1.47-1.34 (m, 4H), 0.78 (t, J=7.4 Hz, 6H). (ES+) m/e 513.2 (M+H)+.

Example 50

2-(3-(4-((4-(1H-pyrazol-4-yl)phenyl)amino)-7,8-dihydro-5H-pyrano[4,3-d]pyrimidin-2-yl)phenoxy)-N-(tert-butyl)acetamide

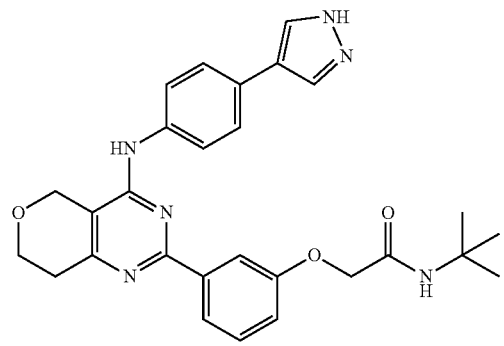 [SMILES: CC(C)(C)NC(=O)COc1cccc(-c2nc3c(c(Nc4ccc(-c5cn[nH]c5)cc4)n2)COCC3)c1]

The compound was synthesized using essentially the same procedure described for the synthesis of Example 40.

Light Yellow solid; Yield: 5.6% (2 steps). $^1$H NMR (400 MHz, DMSO-d$_6$) δ 8.41 (s, 1H), 8.04 (s, 2H), 7.91-7.88 (m, 2H), 7.75 (d, J=8.8 Hz, 2H), 7.63 (d, J=8.4 Hz, 2H), 7.52 (s, 1H), 7.38 (t, J=8.2 Hz, 1H), 7.05-7.02 (m, 1H), 4.71 (s, 2H), 4.46 (s, 2H), 3.99 (t, J=5.4 Hz, 2H), 2.82 (t, J=5.0 Hz, 2H), 1.29 (s, 9H). (ES+) m/e 499.2 (M+H)+.

Example 51

2-(3-(4-((4-(1H-pyrazol-4-yl)phenyl)amino)-7,8-dihydro-5H-pyrano[4,3-d]pyrimidin-2-yl)phenoxy)-N-cyclopentylacetamide

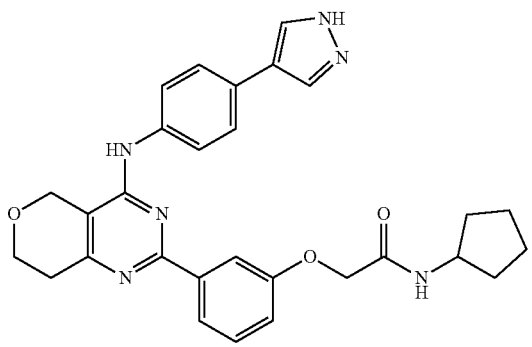 [SMILES: O=C(COc1cccc(-c2nc3c(c(Nc4ccc(-c5cn[nH]c5)cc4)n2)COCC3)c1)NC1CCCC1]

The compound was synthesized using essentially the same procedure described for the synthesis of Example 40.

Light Yellow solid; Yield: 38% (2 steps). $^1$H NMR (400 MHz, DMSO-$d_6$) δ 8.40 (s, 1H), 8.05-8.01 (m, 3H), 7.92-7.90 (m, 2H), 7.76 (d, J=8.8 Hz, 2H), 7.63 (d, J=8.8 Hz, 2H), 7.39 (t, J=8.2 Hz, 1H), 7.06-7.04 (m, 1H), 4.71 (s, 2H), 4.51 (s, 2H), 4.13-4.08 (m, 1H), 4.01-3.98 (m, 2H), 2.82 (s, 2H), 1.81-1.79 (m, 2H), 1.62-1.61 (m, 2H), 1.50-1.44 (m, 4H). (ES+) m/e 511.2 (M+H)$^+$.

Example 52

2-(3-(4-((4-(1H-pyrazol-4-yl)phenyl)amino)-7,8-dihydro-5H-pyrano[4,3-d]pyrimidin-2-yl)phenoxy)-N-cyclobutylacetamide

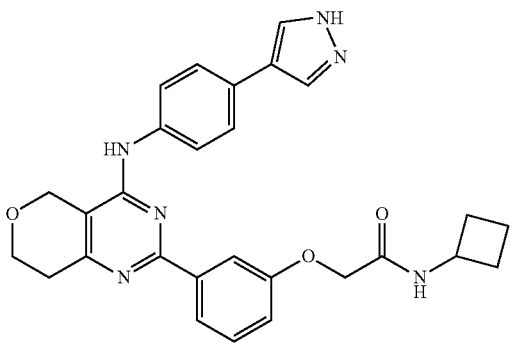 [SMILES: O=C(COc1cccc(-c2nc3c(c(Nc4ccc(-c5cn[nH]c5)cc4)n2)COCC3)c1)NC1CCC1]

The compound was synthesized using essentially the same procedure described for the synthesis of Example 40.

Light Yellow solid; Yield: 20% (2 steps). $^1$H NMR (400 MHz, DMSO-$d_6$) δ 12.82 (s, 1H), 8.41-8.35 (m, 2H), 8.05 (s, 2H), 7.92-7.90 (m, 2H), 7.76 (d, J=8.4 Hz, 2H), 7.64 (d, J=8.8 Hz, 2H), 7.39 (t, J=8.0 Hz, 1H), 7.07-7.05 (m, 1H), 4.71 (s, 2H), 4.50 (s, 2H), 4.36-4.28 (m, 1H), 4.01-3.98 (m, 2H), 2.82 (s, 2H), 2.14-2.12 (m, 2H), 2.04-1.99 (m, 2H), 1.63-1.56 (m, 2H). (ES+) m/e 497.2 (M+H)$^+$.

Example 53

2-(3-(4-((4-(1H-pyrazol-4-yl)phenyl)amino)pyrido[4,3-d]pyrimidin-2-yl)phenoxy)-N-isopropylacetamide

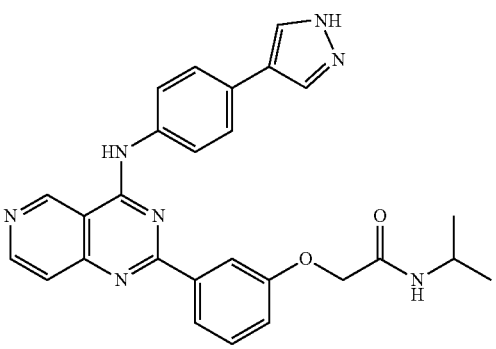 [SMILES: CC(C)NC(=O)COc1cccc(-c2nc(Nc3ccc(-c4cn[nH]c4)cc3)c3cnccc3n2)c1]

Example 53A methyl 4-(3-methoxybenzamido)nicotinate

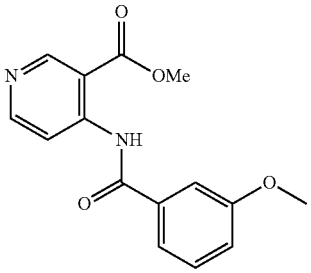 [SMILES: COC(=O)c1cnccc1NC(=O)c1cccc(OC)c1]

To a solution of methyl 4-aminonicotinate (8.00 g, 52.58 mmol) and TEA (10.60 g, 105.16 mmol, 14.58 mL) in DCM (100 mL) was added dropwise the solution of 3-methoxybenzoyl chloride (8.97 g, 52.58 mmol) in CH$_2$Cl$_2$ (50 mL) at 23° C. The mixture was stirred at 23° C. for 16 hours. LCMS showed the desired product was major. The reaction mixture was quenched by addition of water (100 mL) and the mixture was extracted with CH$_2$Cl$_2$ (120 mL×3). The combined organic layers were dried over Na$_2$SO$_4$, filtered and concentrated under reduced pressure to give a residue. The residue was dispersed in CH$_2$Cl$_2$ (80 mL) and stirred for about 4 hours. The suspension was filtered and the resulting solid was dried to afford the title compound (14.00 g, 93%) as a white solid.

Example 53B

4-(3-methoxybenzamido)nicotinamide

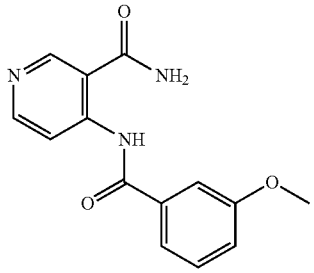 [SMILES: COc1cccc(C(=O)Nc2ccncc2C(N)=O)c1]

To MeOH (450 mL) was bubbled $NH_3$ for at room temperature for 30 minutes and about $NH_3$ (50 g) was bubbled into MeOH. To the $NH_3$/MeOH solution was added methyl 4-(3-methoxybenzamido)nicotinate (14.00 g, 48.90 mmol). Then the reaction was stirred at room temperature for 16 hours. LC/MS (EW991-1067-P1A) showed the desired product as the major product. TLC (EtOAc Rf=0.4) showed that the starting materials were consumed completely and there was a main new spot. The reaction mixture was concentrated to remove most of MeOH. The resulting suspension was filtered, the solid was washed with MeOH, dried under reduce pressure to afford the title compound (11.50 g, 87%) as a white solid.

Example 53C

2-(3-methoxyphenyl)pyrido[4,3-d]pyrimidin-4-ol

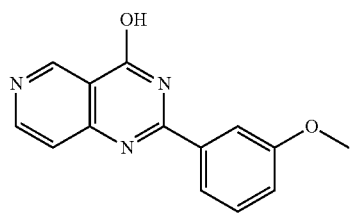 [SMILES: COc1cccc(-c2nc(O)c3cnccc3n2)c1]

To the solution of 2-(3-methoxyphenyl)pyrido[4,3-d]pyrimidin-4-ol (11.50 g, 42.39 mmol) in i-PrOH (100 mL) was added aqueous NaOH (2 M, 127.17 mL). Then the reaction was stirred at 90° C. for 3 hours. LCMS showed the desired product was major. TLC (EtOAc Rf=0.45) showed the starting materials were consumed completely and there was a main new spot. The reaction mixture was concentrated to remove most of i-PrOH. The resulting mixture was adjusted to pH=7 with addition of 6 N HCl. The resulting suspension was filtered. The solid was collected and dried under reduce pressure to give the title compound (9.50 g, 89%) as a white solid. $^1$H NMR (400 MHz, DMSO-$d_6$) δ 12.80 (s, 1H), 9.27 (s, 1H), 8.77 (d, J=8.0 Hz, 1H), 7.85 (d, J=8.0 Hz, 1H), 7.81 (s, 1H), 7.58 (d, J=5.6 Hz, 1H), 7.47 (d, J=8.0, 8.0 Hz, 1H), 7.18 (d, J=8.0, 5.6 Hz, 1H), 3.87 (s, 3H).

Example 53D

4-chloro-2-(3-methoxyphenyl)pyrido[4,3-d]pyrimidine

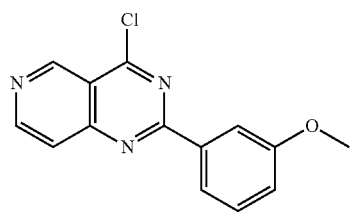 [SMILES: COc1cccc(-c2nc(Cl)c3cnccc3n2)c1]

To the mixture of 2-(3-methoxyphenyl)pyrido[4,3-d]pyrimidin-4-ol (9.00 g, 35.54 mmol) in $POCl_3$ (115.50 g, 753.28 mmol, 70.00 mL) was added DIPEA (9.19 g, 71.07 mmol, 12.41 mL). Then the reaction was stirred at 80° C. for 2 hours. LCMS showed there was 55% MeO replaced product and about 45% starting material remained. So the reaction was stirred at 80° C. for another 14 hours. LCMS showed there was 85% MeO replaced product. The reaction mixture was concentrated to give the title compound (9.60 g, crude) as a light brown solid which was used in the next step directly.

Example 53E

N-(4-bromophenyl)-2-(3-methoxyphenyl)pyrido[4,3-d]pyrimidin-4-amine

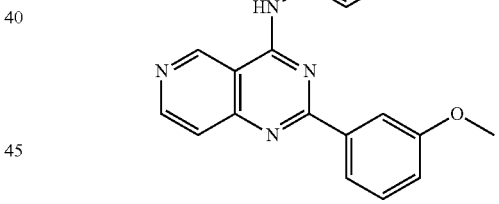

The mixture of 4-chloro-2-(3-methoxyphenyl)pyrido[4,3-d]pyrimidine (9.60 g, 35.33 mmol), 4-bromoaniline (9.12 g, 53.00 mmol) and DIPEA (18.27 g, 141.32 mmol, 24.69 mL) in THF (150 mL) was stirred at 10° C. for 2 hours. LCMS showed the starting materials were major and the reaction was stirred at 60° C. for another 16 hours. LCMS showed there were still all starting materials. The reaction mixture was concentrated to give a residue and the residue was purified roughly via silica chromatography ($CH_2Cl_2$) to recover the mixture of the two starting materials (18 g) as a black brown solid.

The recovered the mixture of the two starting materials (18 g) and DIPEA (8.56 g, 66.24 mmol, 11.57 mL) in n-BuOH (150 mL) was stirred at 100° C. for 16 hours. LCMS showed the desired product was major. The reaction was cooled to room temperature and water (150 mL) was added. The resulting mixture was extracted with EtOAc (150 mL×4). The combined organic layers were washed with brine (100 mL), dried over $Na_2SO_4$, concentrated to give a residue. The residue was dispersed in EtOAc (150 mL) and the mixture was stirred at room temperature for 30 minutes. The yellow solid (3.8 g) was collected by filtration and the filtrate was concentrated. The residue was purified via silica chromatography (petroleum ether/EtOAc=10:1 to 3:1, then CH$_2$Cl$_2$ to CH$_2$Cl$_2$:MeOH=20:1). The obtained title compound was re-purified via recrystallization (petroleum ether/EtOAc=1:1) to afford 1.4 g product (purity: ~80%) as a light brown solid. $^1$H NMR (400 MHz, DMSO-d$_6$) δ 10.46 (s, 1H), 9.86 (s, 1H), 8.81 (d, J=5.6 Hz, 1H), 8.04 (d, J=8.0 Hz, 1H), 7.99 (s, 1H), 7.94 (d, J=8.0 Hz, 2H), 7.73 (d, J=5.6 Hz, 1H), 7.68 (d, J=8.0 Hz, 2H), 7.46 (d, J=8.0, 8.0 Hz, 1H), 7.13 (d, J=8.0, 5.6 Hz, 1H), 3.86 (s, 3H).

Example 53F 3-(4-((4-bromophenyl)amino)pyrido[4,3-d]pyrimidin-2-yl)phenol

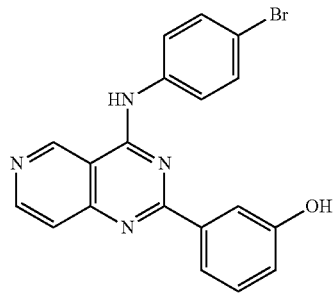 [SMILES: Oc1cccc(-c2nc(Nc3ccc(Br)cc3)c3cnccc3n2)c1]

To the suspension of N-(4-bromophenyl)-2-(3-methoxyphenyl)pyrido[4,3-d]pyrimidin-4-amine (3.50 g, 8.59 mmol) in CH$_2$Cl$_2$ (60 mL) was added BBr$_3$ (10.76 g, 42.95 mmol, 4.14 mL) at 0° C. under N$_2$. The reaction was stirred at 35° C. for 5 hrs. LCMS showed that there was 33% desired product and 37% starting materials remaining. After the reaction was stirred for another 16 hr, LCMS still showed 35% starting materials although there was 34% desired product as well. Additional BBr$_3$ (10.76 g, 42.95 mmol, 4.14 mL) was added and the reaction was stirred at 35° C. for another 5 hours. LCMS showed there was 38% desired product and still 25% starting materials remained. The reaction was quenched with ice water (150 mL) and adjusted to pH=7 with sat.Na$_2$CO$_3$. The resulted suspension was extracted with the mixed solvent (CH$_2$Cl$_2$:MeOH=10:1 200 mL×3). The combined organic layers were filtered. The filtrate was washed with brine (150 mL), dried over Na$_2$SO$_4$ and concentrated to give the crude yellow solid. The crude yellow solid was dispersed in EtOAc (50 mL). The mixture was stirred at room temperature for 20 minutes and filtered to get a yellow solid. The solid was dispersed in CH$_2$Cl$_2$ (500 mL) and water (100 mL) and the resulting mixture was extracted with CH$_2$Cl$_2$ (200 mL×5). The combined organic layers were dried over Na$_2$SO$_4$, filtered and concentrated to give the title compound (2.40 g, crude) as a yellow solid. HNMR showed there was about 25% starting materials remained, and the obtained mixture of product was used in the next step directly.

Example 53G methyl 2-(3-(4-((4-bromophenyl)amino)pyrido[4,3-d]pyrimidin-2-yl)phenoxy)acetate

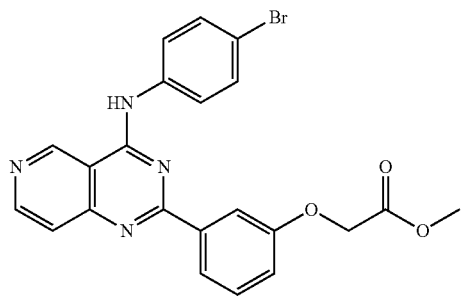 [SMILES: COC(=O)COc1cccc(-c2nc(Nc3ccc(Br)cc3)c3cnccc3n2)c1]

The mixture of 3-(4-((4-bromophenyl)amino)pyrido[4,3-d]pyrimidin-2-yl)phenol (2.00 g, 5.09 mmol, purity: 75%), methyl 2-bromoacetate (544.60 mg, 3.56 mmol, 336.17 uL) and K$_2$CO$_3$ (1.06 g, 7.64 mmol) in DMF (20 mL) was stirred at 40° C. for 1 hour. LCMS showed there were 20% desired product and 30% di-substituted byproduct. The reaction mixture of another small scale reaction was combined with this reaction. Water (20 mL) was added and the resulting mixture was extracted with EtOAc (100 mL×3). The combined organic layers were washed with brine (20 mL), dried over Na$_2$SO$_4$, concentrated to give a residue. The residue was purified via prep-MPLC. The purified aqueous solution of desired product was basified with sat.Na$_2$CO$_3$ to pH=9 and the resulting mixtures were extracted with EtOAc (100 mL×4). The combined organic layers were washed with brine (20 mL), dried over Na$_2$SO$_4$, filtered and concentrated to afford the title compound (420 mg, HNMR: EW991-1136-P1B) as a yellow solid altogether. $^1$H NMR (400 MHz, DMSO-d$_6$) δ 10.41 (s, 1H), 9.84 (s, 1H), 8.81 (d, J=5.6 Hz, 1H), 8.08 (d, J=8.0 Hz, 1H), 7.94 (s, 1H), 7.92 (d, J=8.0 Hz, 2H), 7.71 (d, J=5.6 Hz, 1H), 7.68 (d, J=8.0 Hz, 2H), 7.47 (d, J=8.0, 8.0 Hz, 1H), 7.14 (d, J=8.0, 5.6 Hz, 1H), 4.92 (s, 2H), 3.70 (s, 3H).

Example 53H methyl 2-(3-(4-((4-(1-(tetrahydro-2H-pyran-2-yl)-1H-pyrazol-4-yl)phenyl)amino)pyrido[4,3-d]pyrimidin-2-yl)phenoxy)acetate

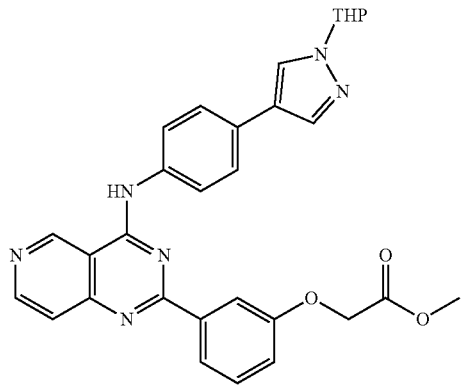

The mixture of methyl 2-(3-(4-((4-bromophenyl)amino)pyrido[4,3-d]pyrimidin-2-yl)phenoxy)acetate (370.00 mg, 795.19 umol), 1-(tetrahydro-2H-pyran-2-yl)-4-(4,4,5,5-tetramethyl-1,3,2-dioxaborolan-2-yl)-1H-pyrazole (287.54 mg, 1.03 mmol), K₂CO₃ (219.81 mg, 1.59 mmol) and Pd(dppf)Cl₂ (116.37 mg, 159.04 umol) in dioxane (10 mL) and H₂O (1 mL) was stirred at 100° C. under N₂ 16 hours. TLC (DCM:MeOH=10:1 Rf=0.46) showed there was a main new spot. The reaction was cooled to room temperature and water (15 mL) was added. The resulting mixture was extracted with EtOAc (30 mL×3). The combined organic layers were washed with brine (20 mL), dried over Na₂SO₄, filtered, concentrated to give the crude product which was purified via silica chromatography (CH₂Cl₂ to CH₂Cl₂:MeOH=20:1) to give the title compound (380.00 mg, purity: 80%) as a yellow solid.

Example 53I 2-(3-(4-((4-(1-(tetrahydro-2H-pyran-2-yl)-1H-pyrazol-4-yl)phenyl)amino)pyrido[4,3-d]pyrimidin-2-yl)phenoxy)acetic acid

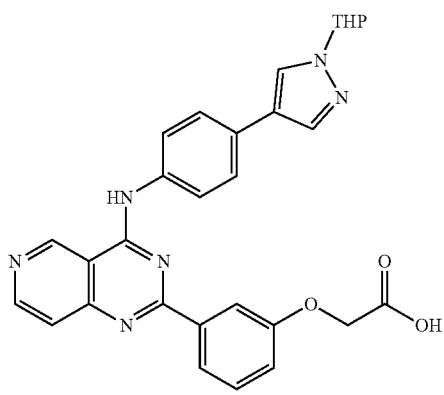

The mixture of methyl 2-(3-(4-((4-(1-(tetrahydro-2H-pyran-2-yl)-1H-pyrazol-4-yl)phenyl)amino)pyrido[4,3-d]pyrimidin-2-yl)phenoxy)acetate (350.00 mg, 652.28 umol) and LiOH (46.87 mg, 1.96 mmol) in THF (5 mL) and H₂O (1 mL) was stirred at 15° C. for 16 hours. LCMS showed the desired product was major. The reaction mixture was concentrated to give a residue. The residue was dispersed in water (10 mL), acidified to pH=5 with 1 N HCl and the resulting yellow solid was filtered, washed with water and dried under azeotropic condition with toluene to give the title compound (180 mg).

Example 53J

N-isopropyl-2-(3-(4-((4-(1-(tetrahydro-2H-pyran-2-yl)-1H-pyrazol-4-yl)phenyl)amino)pyrido[4,3-d]pyrimidin-2-yl)phenoxy)acetamide

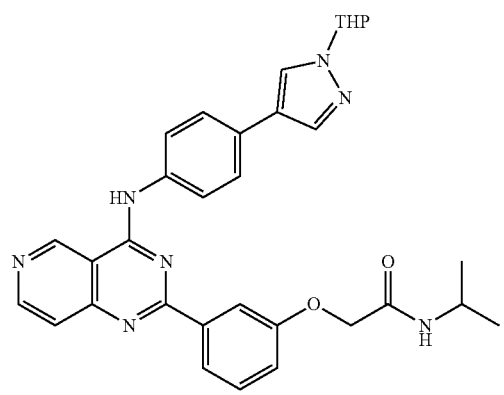

After the solution of 2-(3-(4-((4-(1-(tetrahydro-2H-pyran-2-yl)-1H-pyrazol-4-yl)phenyl)amino)pyrido[4,3-d]pyrimidin-2-yl)phenoxy)acetic acid (100.00 mg, 191.37 umol), HATU (109.15 mg, 287.05 umol) and DIPEA (74.20 mg, 574.11 umol, 100.27 uL) in DMF (1 mL) stirring at 15° C. for 15 minutes, propan-2-amine (22.62 mg, 382.74 umol, 32.79 uL) was added. Then the reaction was stirred at 15° C. for another 15.8 hours. LCMS showed the desired product was the major component. Water (15 mL) was added and the resulting mixture was extracted with EtOAc (20 mL×2). The combined organic layers were washed with brine (15 mL×2), dried over Na₂SO₄, filtered, concentrated to give the title compound (130 mg, crude) as a brown solid which was used in the next step directly.

Example 53K 2-(3-(4-((4-(1H-pyrazol-4-yl)phenyl)amino)pyrido[4,3-d]pyrimidin-2-yl)phenoxy)-N-isopropylacetamide

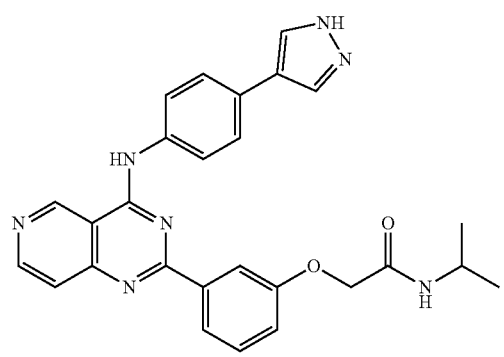 [SMILES: CC(C)NC(=O)COc1cccc(-c2nc(Nc3ccc(-c4cn[nH]c4)cc3)c3cnccc3n2)c1]

To the solution of N-isopropyl-2-(3-(4-((4-(1-(tetrahydro-2H-pyran-2-yl)-1H-pyrazol-4-yl)phenyl)amino)pyrido[4,3-d]pyrimidin-2-yl)phenoxy)acetamide (100.00 mg, 177.42 umol) in CH₂Cl₂ (3.00 mL) was added HCl/dioxane (4 N, 3.00 mL). Then the reaction was stirred at 15° C. for 1 hour. LCMS showed the desired product was major. The reaction mixture was concentrated to give a residue which was basified with 1 M NaOH to pH=10. The resulting mixture was extracted with EtOAc (50 mL×3). The combined organic layers were washed with brine (15 mL), dried over Na$_2$SO$_4$, filtered and concentrated to give the crude product which was purified via prep-HPLC (FA conditions) to afford the title compound (28.00 mg, 29%) as a red solid. $^1$H NMR (400 MHz, DMSO-d$_6$) δ 10.40 (s, 1H), 9.88 (s, 1H), 8.81 (d, J=5.6 Hz, 1H), 8.36 (s, 1H), 8.12-8.08 (m, 4H), 8.01-7.96 (m, 3H), 7.76 (d, J=8.0 Hz, 2H), 7.70 (d, J=5.6 Hz, 1H), 7.47 (d, J=8.0, 8.0 Hz, 1H), 7.16 (d, J=8.0, 5.6 Hz, 1H), 4.56 (s, 2H), 4.05-3.96 (m, 1H), 1.11 (d, J=6.4 Hz, 6H). (ES+) m/e 480.1 (M+H)$^+$.

Example 54

2-(3-(4-((4-(1H-pyrazol-4-yl)phenyl)amino)-6-acetyl-6,7-dihydro-5H-pyrrolo[3,4-d]pyrimidin-2-yl)phenoxy)-N-isopropylacetamide

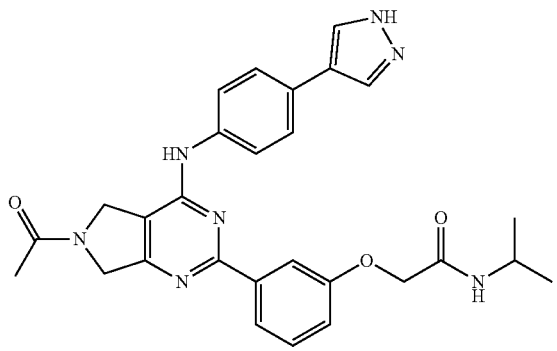 [SMILES: CC(=O)N1Cc2nc(-c3cccc(OCC(=O)NC(C)C)c3)nc(Nc3ccc(-c4cn[nH]c4)cc3)c2C1]

Example 54A 2,4-dichloro-6,7-dihydro-5H-pyrrolo[3,4-d]pyrimidine

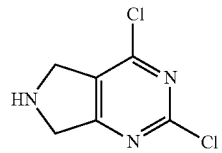 [SMILES: Clc1nc(Cl)c2c(n1)CNC2]

The mixture of tert-butyl 2,4-dichloro-5,7-dihydro-6H-pyrrolo[3,4-d]pyrimidine-6-carboxylate (2.00 g, 6.89 mmol) in CH$_2$Cl$_2$ (15.00 mL) was added HCl/dioxane (4 N, 10.00 mL). The mixture was stirred at 15° C. for 2 h. LCMS showed one peak of desired product was detected. The mixture was concentrated under reduced pressure to afford the title compound (2.10 g, crude, HCl salt) as a light yellow solid which was used into next step without further purification.

Example 54B 1-(2,4-dichloro-5,7-dihydro-6H-pyrrolo[3,4-d]pyrimidin-6-yl)ethan-1-one

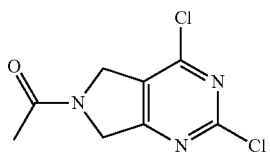

To the mixture of 2,4-dichloro-6,7-dihydro-5H-pyrrolo[3,4-d]pyrimidine (2.10 g, 9.27 mmol, HCl salt) in CH$_2$Cl$_2$ (30.00 mL) was added dropwise TEA (2.81 g, 27.81 mmol, 3.85 mL) at 0° C. The mixture was stirred at 0° C. for 5 min. Then to the mixture was added dropwise acetyl chloride (873.42 mg, 11.13 mmol, 794.01 uL) at 0° C. The mixture was stirred under N$_2$ at 0° C. for 1.5 h. TLC (petroleum ether/EtOAc=1:1, Rf=0.35) showed that one new main spot was detected. The mixture was diluted with CH$_2$Cl$_2$ (30 mL) and washed with water (30 mL×2), citric acid (10%, 30 mL×3), sat.NaHCO$_3$ (30 mL×2), brine (30 mL×2). The organic layer was dried over Na$_2$SO$_4$, filtered and concentrated under reduced pressure to give a residue. The residue was purified by column chromatography (SiO$_2$, petroleum ether/EtOAc=40:1 to 0:1) to afford the title compound (1.1 g, 51%) as a light yellow solid. $^1$H NMR (400 MHz, DMSO-d$_6$) δ 4.96 (s, 1H), 4.91 (s, 1H), 4.68 (s, 1H), 4.62 (s, 1H), 2.09-2.07 (m, 3H).

Example 54C 1-(2-chloro-4-((4-(1-(tetrahydro-2H-pyran-2-yl)-1H-pyrazol-4-yl)phenyl)amino)-5,7-dihydro-6H-pyrrolo[3,4-d]pyrimidin-6-yl)ethan-1-one

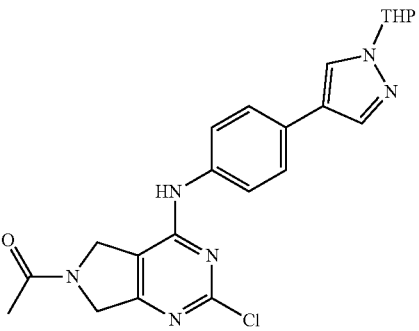

To the mixture of 1-(2,4-dichloro-5,7-dihydro-6H-pyrrolo[3,4-d]pyrimidin-6-yl)ethan-1-one (1.10 g, 4.74 mmol) and 4-(1-(tetrahydro-2H-pyran-2-yl)-1H-pyrazol-4-yl)aniline (980.25 mg, 4.03 mmol) in n-BuOH (10.00 mL) was added DIPEA (1.84 g, 14.22 mmol, 2.48 mL). The mixture was stirred under N$_2$ at 100° C. for 16 h. The mixture was cooled to room temperature and filtered. The solid was washed with petroleum ether/EtOAc=8:1 (60 mL) and dried over under vacuum to give the title compound (1.5 g, 72%) as brownish yellow solid. $^1$H NMR (400 MHz, DMSO-d$_6$) δ 8.57 (m, 1H), 8.31 (s, 1H), 7.93 (s, 1H), 7.69-7.61 (m, 4H), 5.40 (d, J=8.0 Hz, 1H), 4.73 (s, 2H), 4.53-4.47 (m, 2H), 3.96-3.93 (m, 1H), 3.68-3.62 (m, 1H), 2.14-2.06 (m, 4H), 1.96-1.94 (m, 2H), 1.57-1.52 (m, 3H).

Example 54D 2-(3-(4-((4-(1H-pyrazol-4-yl)phenyl)amino)-6-acetyl-6,7-dihydro-5H-pyrrolo[3,4-d]pyrimidin-2-yl)phenoxy)-N-isopropylacetamide

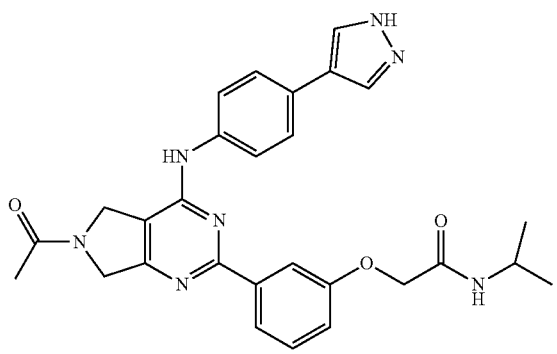 [SMILES: CC(=O)N1Cc2nc(-c3cccc(OCC(=O)NC(C)C)c3)nc(Nc3ccc(-c4cn[nH]c4)cc3)c2C1]

To the mixture of 1-(2-chloro-4-((4-(1-(tetrahydro-2H-pyran-2-yl)-1H-pyrazol-4-yl)phenyl)amino)-5,7-dihydro-6H-pyrrolo[3,4-d]pyrimidin-6-yl)ethan-1-one (1.00 eq) and N-isopropyl-2-(3-(4,4,5,5-tetramethyl-1,3,2-dioxaborolan-2-yl)phenoxy)acetamide (1.20 eq) in dioxane (5.00 mL), H₂O (500.00 uL) was added K₂CO₃ (2.00 eq), Pd(dppf)Cl₂ (0.10 eq). The mixture was stirred under N₂ at 90° C. for 16 h. The reaction mixture was cooled to room temperature and diluted with water. The resulting mixture was extracted with CH₂Cl₂. The combined organic layers were washed with brine, dried over Na₂SO₄, filtered and concentrated under reduced pressure to give a residue. The residue was purified by column chromatography or recrystallization to afford 2-(3-(6-acetyl-4-((4-(1-(tetrahydro-2H-pyran-2-yl)-1H-pyrazol-4-yl)phenyl)amino)-6,7-dihydro-5H-pyrrolo[3,4-d]pyrimidin-2-yl)phenoxy)-N-isopropylacetamide.

To the mixture of 2-(3-(6-acetyl-4-((4-(1-(tetrahydro-2H-pyran-2-yl)-1H-pyrazol-4-yl)phenyl)amino)-6,7-dihydro-5H-pyrrolo[3,4-d]pyrimidin-2-yl)phenoxy)-N-isopropylacetamide (1.00 eq) in CH₂Cl₂ (5.00 mL) was added HCl/dioxane (4 N, 5.00 mL). The mixture was stirred at 15° C. for 2-16 h. The mixture was concentrated under reduced pressure to give a residue. The residue was purified by prep-HPLC (FA conditions) to give the title compound.

Off-white solid; Yield: 5% (2 steps). ¹H NMR (400 MHz, DMSO-d₆) δ 12.93 (s, 1H), 9.26 (d, J=14.4 Hz, 1H), 8.46 (s, 1H), 8.16-7.93 (m, 5H), 7.86 (t, J=8.8 Hz, 2H), 7.68-7.63 (m, 2H), 7.46-7.40 (m, 1H), 7.10 (dt, J=8.0, 1.2 Hz, 1H), 4.82 (d, J=8.0 Hz, 2H), 4.63 (s, 1H) 4.57-4.49 (m, 3H), 4.01-3.94 (m, 1H), 2.13-2.09 (m, 3H), 1.09 (d, J=6.4 Hz, 6H). (ES+) m/e 512.2 (M+H)⁺.

Example 55

2-(3-(4-((4-(1H-pyrazol-4-yl)phenyl)amino)-6-acetyl-6,7-dihydro-5H-pyrrolo[3,4-d]pyrimidin-2-yl)phenoxy)-N-(pentan-3-yl)acetamide

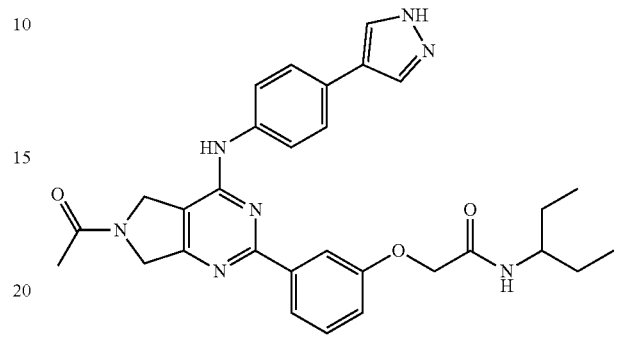

The title compound was synthesized using essentially the same procedure as described in Example 54.

Off-white solid; Yield: 40% (2 steps). ¹H NMR (400 MHz, DMSO-d₆) δ 12.92 (s, 1H), 9.30-9.20 (m, 1H), 8.25-7.91 (m, 4H), 7.85 (t, J=8.4 Hz, 2H), 7.79-7.71 (m, 1H), 7.66 (dd, J=8.8, 5.2 Hz, 2H), 7.43 (dt, J=8.2, 2.8 Hz, 1H), 7.10 (d, J=8.2 Hz, 1H), 4.82 (d, J=9.6 Hz, 2H), 4.68-4.48 (m, 4H), 3.70-3.55 (m, 1H), 2.11 (d, J=7.2 Hz, 3H), 1.53-1.29 (m, 4H), 0.78 (t, J=7.2 Hz, 6H). ¹H NMR (400 MHz, DMSO-d₆) (ES+) m/e 540.2 (M+H)⁺.

Example 56

2-(3-(4-((4-(1H-pyrazol-4-yl)phenyl)amino)-6-acetyl-6,7-dihydro-5H-pyrrolo[3,4-d]pyrimidin-2-yl)phenoxy)-N-(tert-butyl)acetamide

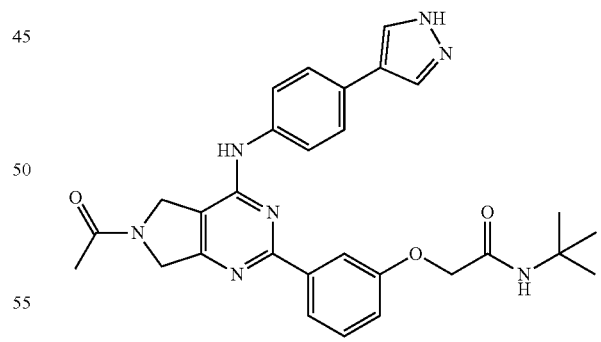

The title compound was synthesized using essentially the same procedure as described in Example 54.

Off-white solid; Yield: 15% (2 steps). ¹H NMR (400 MHz, DMSO-d₆) δ 12.89 (s, 1H), 9.30-9.21 (m, 1H), 8.14-7.90 (m, 4H), 7.90-7.81 (m, 2H), 7.65 (dd, J=8.4, 4.8 Hz, 2H), 7.53 (d, J=12.8 Hz, 1H), 7.42 (dt, J=8.0, 3.2 Hz, 1H), 7.07 (d, J=8.4 Hz, 1H), 4.87-4.77 (m, 2H), 4.66-4.47 (m, 4H), 2.15-2.07 (m, 3H), 1.30 (s, 9H). (ES+) m/e 526.2 (M+H)⁺.

Example 57

2-(3-(4-((4-(1H-pyrazol-4-yl)phenyl)amino)-6-acetyl-5,6,7,8-tetrahydropyrido[4,3-d]pyrimidin-2-yl)phenoxy)-N-cyclopentylacetamide

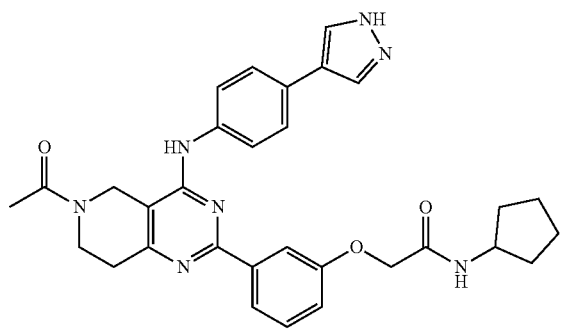 [SMILES: CC(=O)N1CCc2nc(-c3cccc(OCC(=O)NC4CCCC4)c3)nc(Nc3ccc(-c4cn[nH]c4)cc3)c2C1]

The title compound was synthesized using the same procedure as described in Example 60.

Light yellow solid; Yield: 11% (2 steps). $^1$H NMR (400 MHz, DMSO-d$_6$) δ 8.80-8.58 (m, 1H), 8.42 (s, 1H), 8.13-7.98 (m, 3H), 7.93-7.87 (m, 2H), 7.82-7.73 (m, 2H), 7.69-7.60 (m, 2H), 7.39 (t, J=8.2 Hz, 1H), 7.08-7.03 (m, 1H), 4.62 (s, 2H), 4.51 (s, 2H), 4.10 (d, J=14.0, 7.2 Hz, 1H), 3.80 (t, J=5.2 Hz, 2H), 2.95-2.72 (m, 2H), 2.23-2.14 (m, 3H), 1.88-1.74 (m, 2H), 1.68-1.56 (m, 2H), 1.54-1.38 (m, 4H). (ES+) m/e 552.3 (M+H)$^+$.

Example 58

2-(3-(4-((4-(1H-pyrazol-4-yl)phenyl)amino)pyrido[4,3-d]pyrimidin-2-yl)phenoxy)-N-(tert-butyl)acetamide

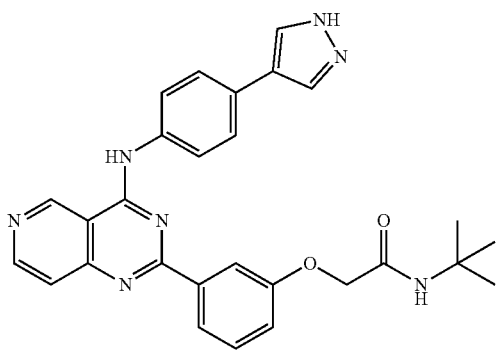 [SMILES: CC(C)(C)NC(=O)COc1cccc(-c2nc(Nc3ccc(-c4cn[nH]c4)cc3)c3cnccc3n2)c1]

The title compound was synthesized using the same procedure as described in Example 53.

$^1$H NMR (400 MHz, DMSO-d$_6$) δ 10.69 (s, 1H), 9.87 (s, 1H), 8.81 (d, J=5.6 Hz, 1H), 8.14-8.06 (m, 4H), 7.96 (d, J=8.0 Hz, 2H), 7.76 (d, J=8.0 Hz, 2H), 7.71 (d, J=5.6 Hz, 1H), 7.57 (s, 1H), 7.47 (d, J=8.0, 8.0 Hz, 1H), 7.14 (d, J=8.0, 5.6 Hz, 1H), 4.52 (s, 2H), 1.32 (s, 9H). (ES+) m/e 494.2 (M+H)$^+$.

Example 59

2-(3-(4-((4-(1H-pyrazol-4-yl)phenyl)amino)-6-acetyl-5,6,7,8-tetrahydropyrido[4,3-d]pyrimidin-2-yl)phenoxy)-N-isobutylacetamide

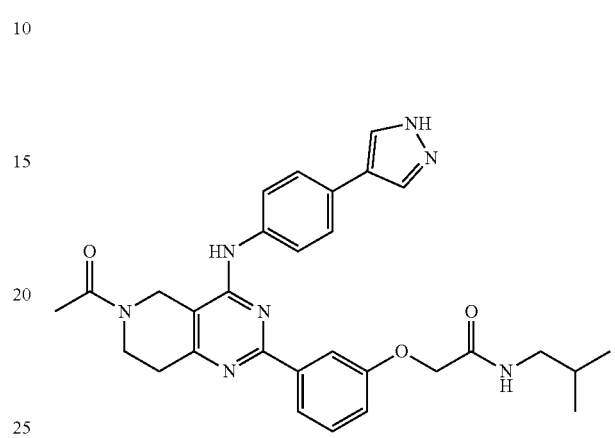

The title compound was synthesized using the same procedure as described in Example 60.

Light yellow solid; Yield: 9.9% (2 steps). $^1$H NMR (400 MHz, DMSO-d$_6$) δ 8.76-8.65 (m, 1H), 8.39 (s, 1H), 8.14 (t, J=5.6 Hz, 1H), 8.06 (s, 2H), 7.92 (d, J=6.8 Hz, 2H), 7.78 (t, J=8.8 Hz, 2H), 7.69-7.63 (m, 2H), 7.40 (t, J=8.0 Hz, 1H), 7.08-7.05 (m, 1H), 4.63 (s, 2H), 4.56 (s, 2H), 3.80 (t, J=5.2 Hz, 2H), 2.96 (t, J=6.8 Hz, 2H), 2.92-2.76 (m, 2H), 2.19 (d, J=10.0 Hz, 3H), 1.75-1.72 (m, 1H), 0.80 (d, J=6.4 Hz, 6H). (ES+) m/e 540.3 (M+H)$^+$.

Example 60

2-(3-(4-((4-(1H-pyrazol-4-yl)phenyl)amino)-6-acetyl-5,6,7,8-tetrahydropyrido[4,3-d]pyrimidin-2-yl)phenoxy)-N-(tert-butyl)acetamide

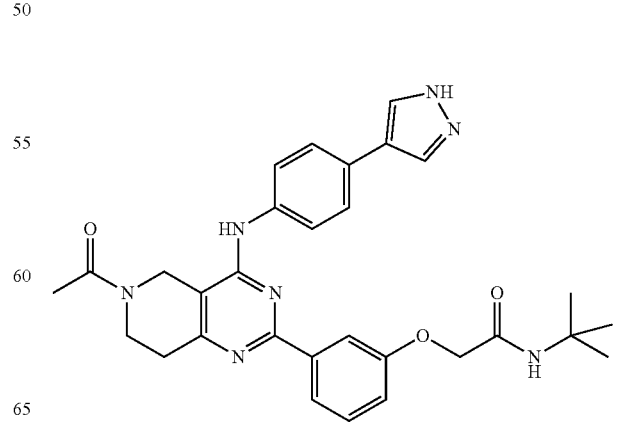

Example 60A 2,4-dichloro-5,6,7,8-tetrahydropyrido[4,3-d]pyrimidine

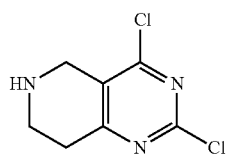 [SMILES: Clc1nc(Cl)c2c(n1)CCNC2]

To the mixture of tert-butyl 2,4-dichloro-7,8-dihydropyrido[4,3-d]pyrimidine-6(5H)-carboxylate (4.00 g, 13.15 mmol) in $CH_2Cl_2$ (15.00 mL) was added HCl/dioxane (4 N, 15.00 mL). The mixture was stirred at 15° C. for 15 h. LCMS showed one main peak of desired product and about 5% of starting material. The mixture was stirred at 30° C. for 1 h. LCMS showed desired product was major. The mixture was concentrated under reduced pressure to afford the title compound (3.07 g, crude, HCl salt) as a white solid which was used in the next step without further purification.

Example 60B 1-(2,4-dichloro-7,8-dihydropyrido[4,3-d]pyrimidin-6(5H)-yl)ethan-1-one

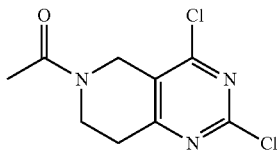

To the mixture of 2,4-dichloro-5,6,7,8-tetrahydropyrido[4,3-d]pyrimidine (1.10 g, 4.57 mmol, HCl) in $CH_2Cl_2$ (30.00 mL) was added dropwise TEA (1.39 g, 13.71 mmol, 1.90 mL) at 0° C. The mixture was stirred at 0° C. for 5 min. Then to the mixture was added dropwise acetyl chloride (430.82 mg, 5.48 mmol, 391.65 uL) at 0° C. The mixture was stirred under $N_2$ at 0° C. for 2 hour. TLC (petroleum ether/EtOAc=1:1, Rf=0.3) showed one main spot. The mixture was diluted with $CH_2Cl_2$ (30 mL) and washed with water (30 mL×2), citric acid (10%, 30 mL×2), sat.NaHCO$_3$ (30 mL×2), brine (30 mL×2). The organic layer was dried over $Na_2SO_4$, filtered and concentrated under reduced pressure to give the title compound (960 mg, crude) as a light brown solid which was used in the next step without further purification. $^1$H NMR (400 MHz, DMSO-d$_6$) δ 4.59-4.58 (m, 2H), 3.78-3.75 (m, 2H), 3.01-2.83 (m, 2H), 2.13 (s, 3H).

Example 60C 1-(2-chloro-4-((4-(1-(tetrahydro-2H-pyran-2-yl)-1H-pyrazol-4-yl)phenyl)amino)-7,8-dihydropyrido[4,3-d]pyrimidin-6(5H)-yl)ethan-1-one

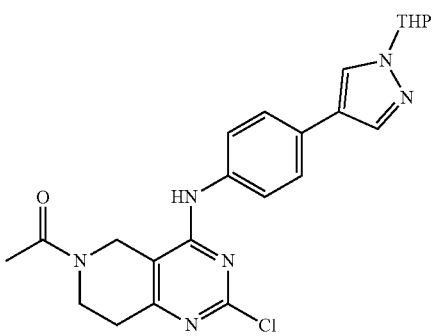

To the mixture of 1-(2,4-dichloro-7,8-dihydropyrido[4,3-d]pyrimidin-6(5H)-yl)ethan-1-one (960.00 mg, 3.90 mmol) and 4-(1-(tetrahydro-2H-pyran-2-yl)-1H-pyrazol-4-yl)aniline (901.43 mg, 3.70 mmol) in n-BuOH (15.00 mL) was added DIPEA (1.01 g, 7.80 mmol, 1.36 mL). The mixture was stirred at 100° C. for 16 h. TLC (petroleum ether/EtOAc=1:1) showed pyrimidine starting material (Rf=0.2) and 4-(1-(tetrahydro-2H-pyran-2-yl)-1H-pyrazol-4-yl)aniline (Rf=0.68) were still present and one main new spot (Rf=0.11) was observed. The mixture was stirred under $N_2$ at 100° C. for 20 h. TLC (petroleum ether/EtOAc=0:1) showed 1-(2,4-dichloro-7,8-dihydropyrido[4,3-d]pyrimidin-6(5H)-yl)ethan-1-one was consumed completely and one main new spot (Rf=0.3) was detected. The mixture was cooled to room temperature and filtered to collect solid. The solid was washed with petroleum ether/EtOAc=10:1 (20 mL) dried over under vacuum to give the title compound (900 mg) as a yellow solid. $^1$H NMR (400 MHz, DMSO-d$_6$) δ 9.04-8.90 (m, 1H), 8.33-8.31 (s, 1H), 7.94-7.93 (m, 1H), 7.65-7.55 (m, 4H), 5.40 (d, J=9.6 Hz, 1H), 4.53-4.52 (m, 2H), 3.96-3.94 (m, 1H), 3.75-3.72 (m, 2H), 3.68-3.64 (m, 1H), 2.81-2.66 (m, 2H), 2.16-2.11 (m, 4H), 1.96-1.94 (m, 2H), 1.57-1.55 (m, 3H).

Example 60D 2-(3-(4-((4-(1H-pyrazol-4-yl)phenyl)amino)-6-acetyl-5,6,7,8-tetrahydropyrido[4,3-d]pyrimidin-2-yl)phenoxy)-N-(tert-butyl)acetamide

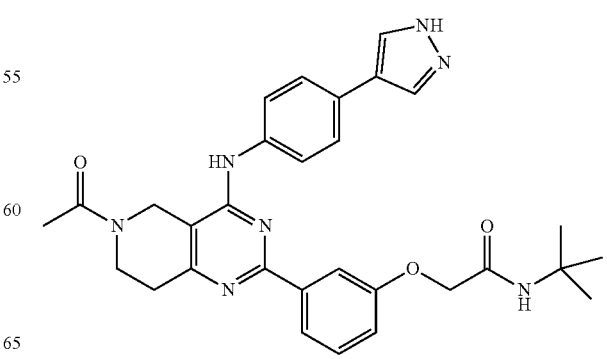

To the mixture of 1-(2-chloro-4-((4-(1-(tetrahydro-2H-pyran-2-yl)-1H-pyrazol-4-yl)phenyl)amino)-7,8-dihydropyrido[4,3-d]pyrimidin-6(5H)-yl)ethan-1-one (1.00 eq) and N-(tert-butyl)-2-(3-(4,4,5,5-tetramethyl-1,3,2-dioxaborolan-2-yl)phenoxy)acetamide (1.20 eq) in dioxane/$H_2O$ (10:1) was added $K_2CO_3$ (2.00 eq), Pd(dppf)$Cl_2$ (0.10 eq). The mixture was stirred under $N_2$ at 90° C. for 16 h. The reaction mixture was cooled to room temperature and diluted with water. The resulting mixture was extracted with EtOAc. The combined organic layers were washed with brine, dried over $Na_2SO_4$, filtered and concentrated under reduced pressure to give a residue. The residue was purified by column chromatography to afford 2-(3-(6-acetyl-4-((4-(1-(tetrahydro-2H-pyran-2-yl)-1H-pyrazol-4-yl)phenyl)amino)-5,6,7,8-tetrahydropyrido[4,3-d]pyrimidin-2-yl)phenoxy)-N-(tert-butyl)acetamide.

To the mixture of 2-(3-(6-acetyl-4-((4-(1-(tetrahydro-2H-pyran-2-yl)-1H-pyrazol-4-yl)phenyl)amino)-5,6,7,8-tetrahydropyrido[4,3-d]pyrimidin-2-yl)phenoxy)-N-(tert-butyl)acetamide (1.00 eq) in $CH_2Cl_2$ (5.00-10.00 mL) was added HCl/dioxane (4 N, 5.00-10.00 mL). The mixture was stirred at 20° C. for 2-16 h. The mixture was concentrated under reduced pressure to give a residue. The residue was purified prep-HPLC (FA conditions) to give the title compound.

Light yellow solid; Yield: 11% (2 steps). $^1$H NMR (400 MHz, DMSO-$d_6$) δ 8.74 (s, 1H), 8.61 (s, 1H), 8.45 (s, 1H), 8.05-7.87 (m, 4H), 7.77 (dd, J=8.8 Hz, 8.8 Hz, 2H), 7.67-7.62 (m, 2H), 7.52 (d, J=3.6 Hz, 1H), 7.38 (dd, J=8.0 Hz, 8.0 Hz, 1H), 7.04-7.02 (dd, J=8.4 Hz, 2.4 Hz, 1H), 4.62 (s, 2H), 4.46 (s, 2H), 3.79 (t, J=5.6 Hz, 2H), 2.90-2.76 (m, 2H), 2.18 (d, J=9.6 Hz, 3H), 1.29 (s, 9H). (ES+) m/e 540.2 (M+H)$^+$.

Example 61 (Assays)

The combination of inhibitors of both oxidative phosphorylation and glycolysis synergistically suppress cellular ATP levels. Therefore, an assay was developed that utilizes the combination of the glucose uptake inhibitors disclosed herein with oligomycin, a well-characterized inhibitor of ATP synthase. Because oligomycin inhibits ATP derived from oxidative phosphorylation, any remaining ATP production is derived from glycolysis. By reading out cellular ATP levels using the Promega Titer Glo kit, the extent of glycolysis inhibition by the glucose uptake inhibitors disclosed herein can be assessed. Utilizing this experimental set-up, we determined the IC50 of glycolysis inhibition for each compound. The values for example compounds can be found in Table 1.

TABLE 1

Glycolysis IC50 values (nM)

| Example Number | Structure | Glycolysis IC50 in HT1080 cells<br>A = 10-100 nM;<br>B = 101-250 Nm; C = 251-500 nM; D = 501-1,000 nM;<br>E = >1,000 nM | Glycolysis IC50 in *P. falciparum*-infected RBCs<br>A = 10-100 nM;<br>B = 101-250 Nm; C = 251-500 nM; D = 501-1,000 nM;<br>E = >1,000 nM |
|---|---|---|---|
| Example 1 | 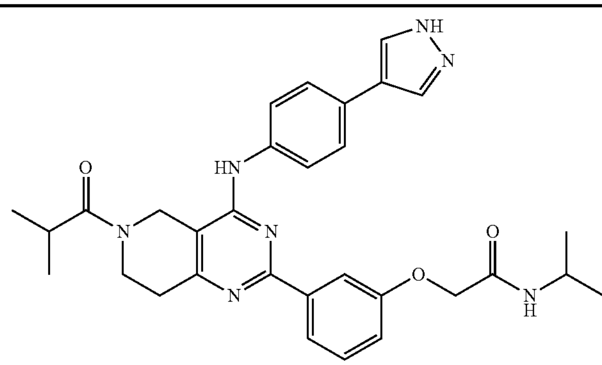 | A | A |
| Example 2 | 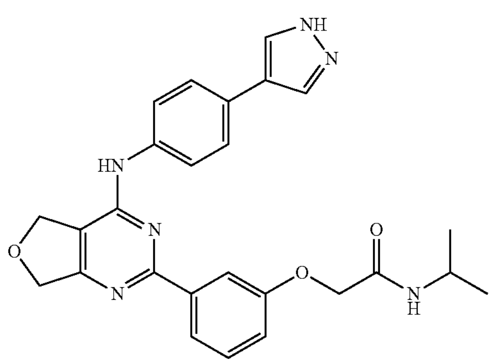 [SMILES: CC(C)NC(=O)COc1cccc(-c2nc3c(c(Nc4ccc(-c5cn[nH]c5)cc4)n2)COC3)c1] | A | B |

TABLE 1-continued
Glycolysis IC50 values (nM)
| Example Number | Structure | Glycolysis IC50 in HT1080 cells A = 10-100 nM; B = 101-250 Nm; C = 251-500 nM; D = 501-1,000 nM; E = >1,000 nM | Glycolysis IC50 in *P. falciparum*-infected RBCs A = 10-100 nM; B = 101-250 Nm; C = 251-500 nM; D = 501-1,000 nM; E = >1,000 nM |
|---|---|---|---|
| Example 3 | 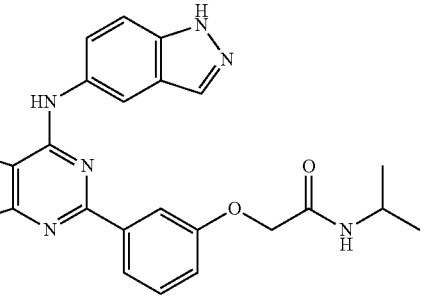 | A | B |
| Example 4 | 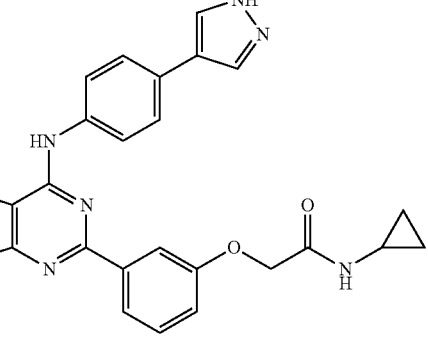 | D | C |
| Example 5 | 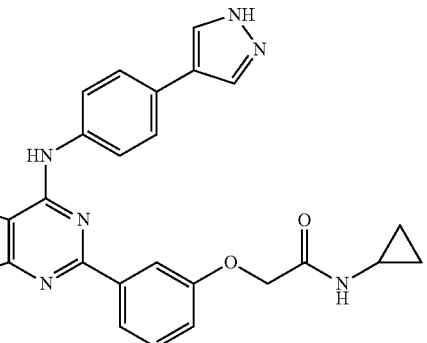 | D | C |
| Example 6 | 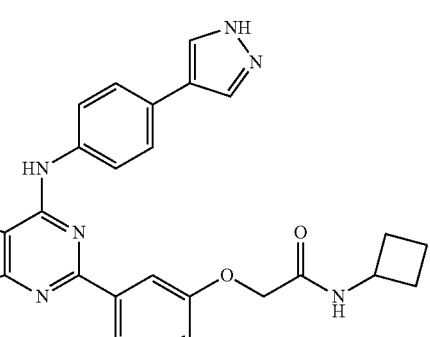 | B | A |

TABLE 1-continued
Glycolysis IC50 values (nM)
| Example Number | Structure | Glycolysis IC50 in HT1080 cells A = 10-100 nM; B = 101-250 Nm; C = 251-500 nM; D = 501-1,000 nM; E = >1,000 nM | Glycolysis IC50 in *P. falciparum*-infected RBCs A = 10-100 nM; B = 101-250 Nm; C = 251-500 nM; D = 501-1,000 nM; E = >1,000 nM |
|---|---|---|---|
| Example 7 | 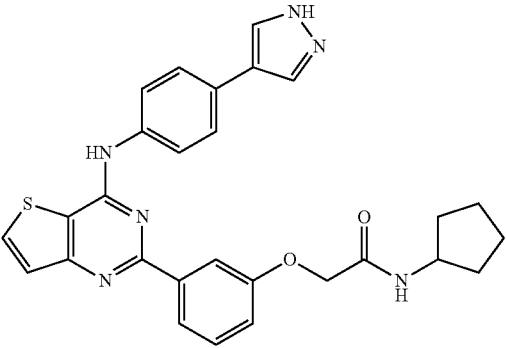 | A | A |
| Example 8 | 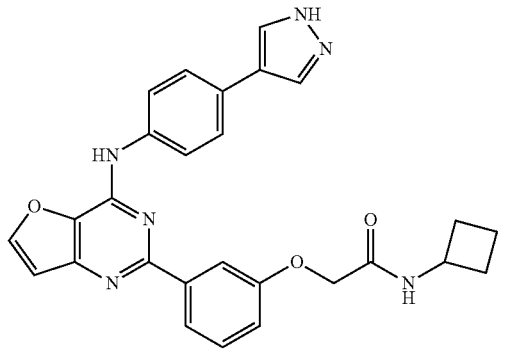 [SMILES: O=C(COc1cccc(-c2nc(Nc3ccc(-c4cn[nH]c4)cc3)c3sccc3n2)c1)NC1CCC1] | C | B |
| Example 9 | 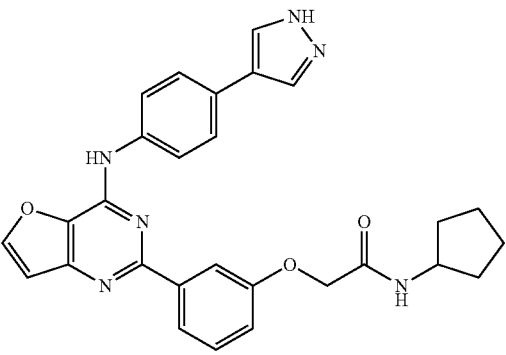 [SMILES: O=C(COc1cccc(-c2nc(Nc3ccc(-c4cn[nH]c4)cc3)c3sccc3n2)c1)NC1CCCC1] | C | C |

TABLE 1-continued
Glycolysis IC50 values (nM)
| Example Number | Structure | Glycolysis IC50 in HT1080 cells A = 10-100 nM; B = 101-250 Nm; C = 251-500 nM; D = 501-1,000 nM; E = >1,000 nM | Glycolysis IC50 in *P. falciparum*-infected RBCs A = 10-100 nM; B = 101-250 Nm; C = 251-500 nM; D = 501-1,000 nM; E = >1,000 nM |
|---|---|---|---|
| Example 10 | 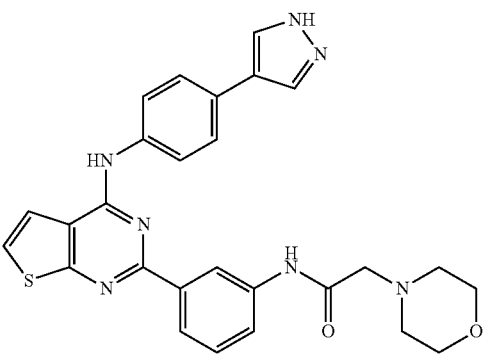 [SMILES: O=C(CN1CCOCC1)Nc1cccc(-c2nc(Nc3ccc(-c4cn[nH]c4)cc3)c3ccsc3n2)c1] | B | B |
|  | 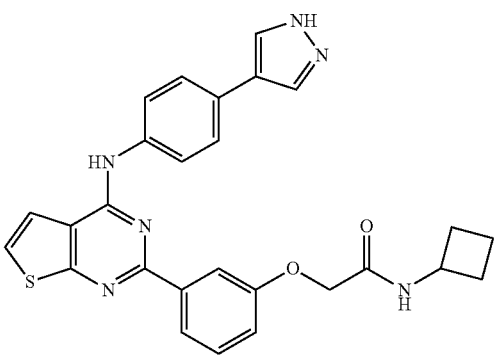 [SMILES: O=C(COc1cccc(-c2nc(Nc3ccc(-c4cn[nH]c4)cc3)c3ccsc3n2)c1)NC1CCC1] |  |  |
| Example 11 | 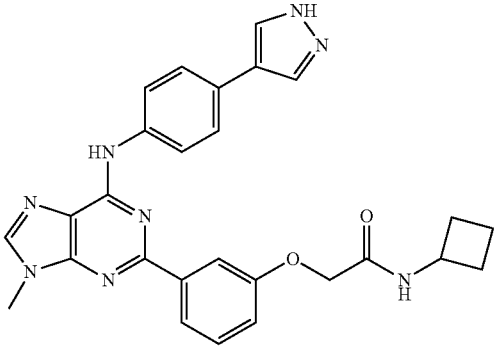 [SMILES: Cn1cnc2c(Nc3ccc(-c4cn[nH]c4)cc3)nc(-c3cccc(OCC(=O)NC4CCC4)c3)nc21] | C | B |

TABLE 1-continued
Glycolysis IC50 values (nM)
| Example Number | Structure | Glycolysis IC50 in HT1080 cells A = 10-100 nM; B = 101-250 Nm; C = 251-500 nM; D = 501-1,000 nM; E = >1,000 nM | Glycolysis IC50 in P. falciparum-infected RBCs A = 10-100 nM; B = 101-250 Nm; C = 251-500 nM; D = 501-1,000 nM; E = >1,000 nM |
|---|---|---|---|
| Example 12 | 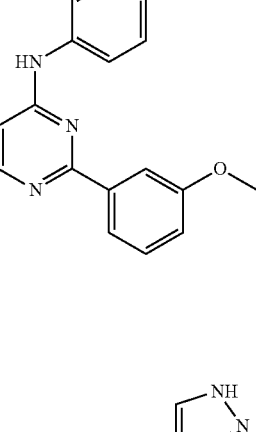 | A | B |
| Example 13 | 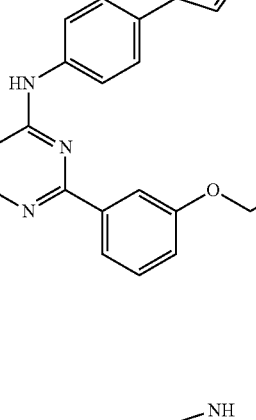 | A | B |
| Example 14 | 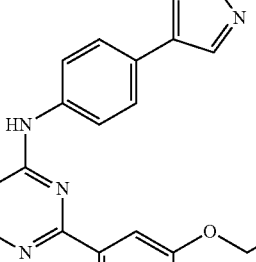 | B | C |

TABLE 1-continued

Glycolysis IC50 values (nM)

| Example Number | Structure | Glycolysis IC50 in HT1080 cells A = 10-100 nM; B = 101-250 Nm; C = 251-500 nM; D = 501-1,000 nM; E = >1,000 nM | Glycolysis IC50 in *P. falciparum*-infected RBCs A = 10-100 nM; B = 101-250 Nm; C = 251-500 nM; D = 501-1,000 nM; E = >1,000 nM |
|---|---|---|---|
| Example 15 | 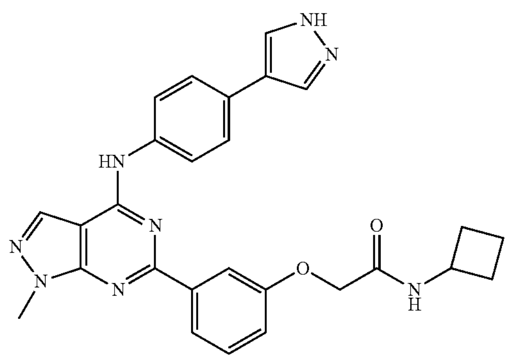 [SMILES: Cn1ncc2c(Nc3ccc(-c4cn[nH]c4)cc3)nc(-c3cccc(OCC(=O)NC4CCC4)c3)nc21] | C | B |
| Example 16 | 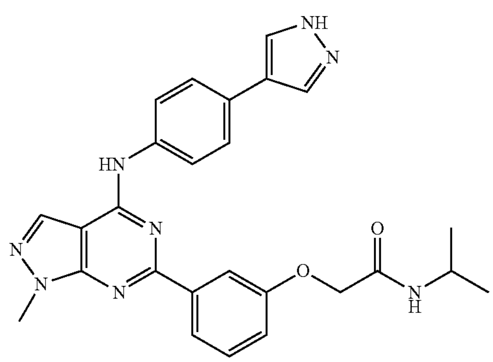 [SMILES: CC(C)NC(=O)COc1cccc(-c2nc(Nc3ccc(-c4cn[nH]c4)cc3)c3cnn(C)c3n2)c1] | C | A |
| Example 17 | 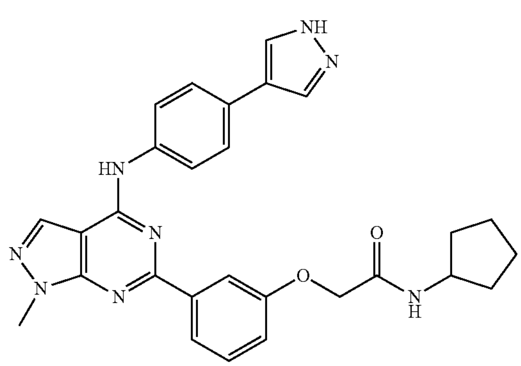 [SMILES: Cn1ncc2c(Nc3ccc(-c4cn[nH]c4)cc3)nc(-c3cccc(OCC(=O)NC4CCCC4)c3)nc21] | B | B |

TABLE 1-continued

Glycolysis IC50 values (nM)

| Example Number | Structure | Glycolysis IC50 in HT1080 cells A = 10-100 nM; B = 101-250 Nm; C = 251-500 nM; D = 501-1,000 nM; E = >1,000 nM | Glycolysis IC50 in *P. falciparum*-infected RBCs A = 10-100 nM; B = 101-250 Nm; C = 251-500 nM; D = 501-1,000 nM; E = >1,000 nM |
|---|---|---|---|
| Example 18 | 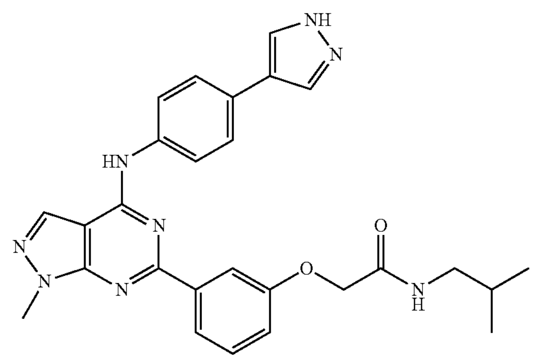 [SMILES: CC(C)CNC(=O)COc1cccc(-c2nc(Nc3ccc(-c4cn[nH]c4)cc3)c3cnn(C)c3n2)c1] | B | A |
| Example 19 | 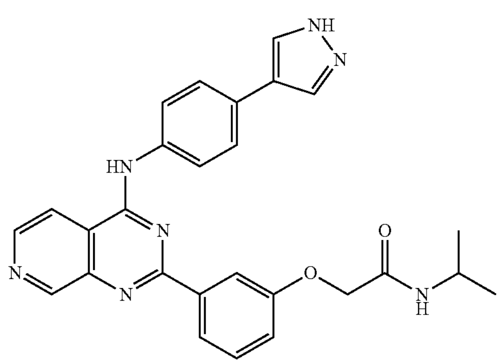 [SMILES: CC(C)NC(=O)COc1cccc(-c2nc(Nc3ccc(-c4cn[nH]c4)cc3)c3ccncc3n2)c1] | A | B |
| Example 20 | 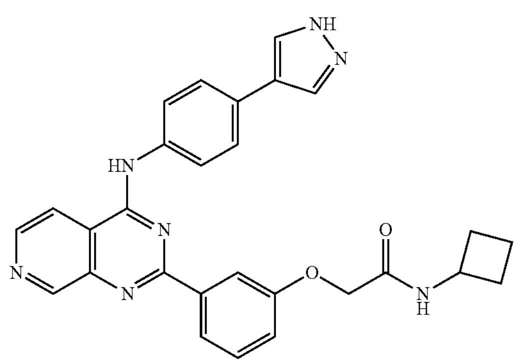 [SMILES: O=C(COc1cccc(-c2nc(Nc3ccc(-c4cn[nH]c4)cc3)c3ccncc3n2)c1)NC1CCC1] | A | B |

TABLE 1-continued

Glycolysis IC50 values (nM)

| Example Number | Structure | Glycolysis IC50 in HT1080 cells A = 10-100 nM; B = 101-250 Nm; C = 251-500 nM; D = 501-1,000 nM; E = >1,000 nM | Glycolysis IC50 in *P. falciparum*-infected RBCs A = 10-100 nM; B = 101-250 Nm; C = 251-500 nM; D = 501-1,000 nM; E = >1,000 nM |
|---|---|---|---|
| Example 21 | 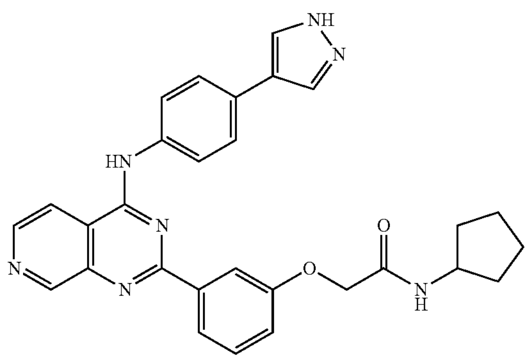 [SMILES: O=C(COc1cccc(-c2nc(Nc3ccc(-c4cn[nH]c4)cc3)c3ccncc3n2)c1)NC1CCCC1] | A | B |
| Example 22 | 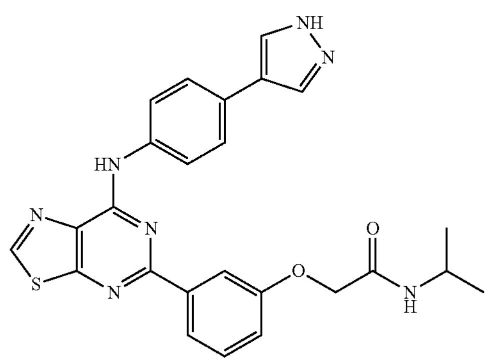 [SMILES: CC(C)NC(=O)COc1cccc(-c2nc(Nc3ccc(-c4cn[nH]c4)cc3)c3ncsc3n2)c1] | C | C |
| Example 23 | 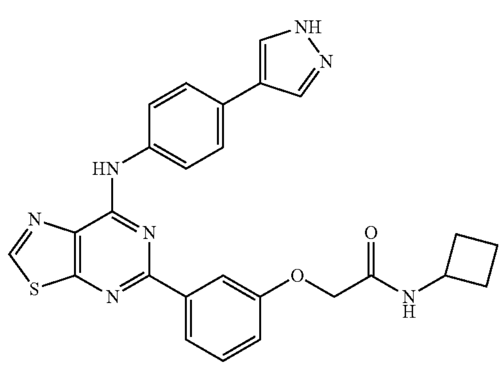 [SMILES: O=C(COc1cccc(-c2nc(Nc3ccc(-c4cn[nH]c4)cc3)c3ncsc3n2)c1)NC1CCC1] | C | C |

TABLE 1-continued

Glycolysis IC50 values (nM)

| Example Number | Structure | Glycolysis IC50 in HT1080 cells A = 10-100 nM; B = 101-250 Nm; C = 251-500 nM; D = 501-1,000 nM; E = >1,000 nM | Glycolysis IC50 in *P. falciparum*-infected RBCs A = 10-100 nM; B = 101-250 Nm; C = 251-500 nM; D = 501-1,000 nM; E = >1,000 nM |
|---|---|---|---|
| Example 24 | 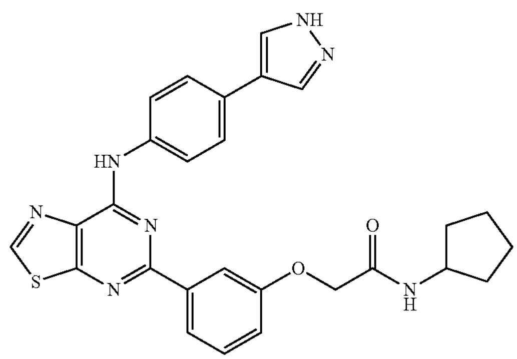 [SMILES: O=C(COc1cccc(-c2nc(Nc3ccc(-c4cn[nH]c4)cc3)c3ncsc3n2)c1)NC1CCCC1] | B | C |
| Example 25 | 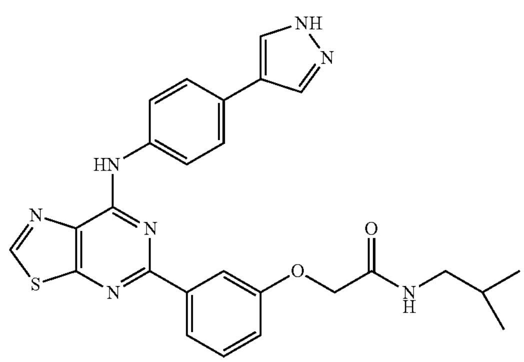 [SMILES: CC(C)CNC(=O)COc1cccc(-c2nc(Nc3ccc(-c4cn[nH]c4)cc3)c3ncsc3n2)c1] | C | C |
| Example 26 | 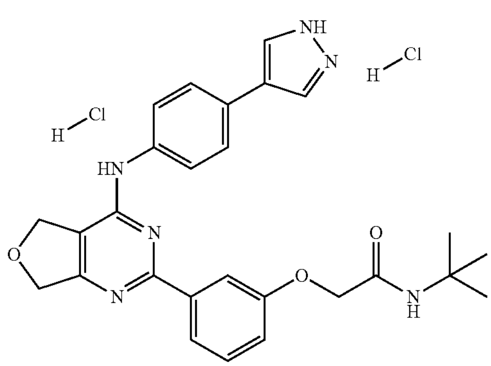 | A | B |

TABLE 1-continued
Glycolysis IC50 values (nM)
| Example Number | Structure | Glycolysis IC50 in HT1080 cells A = 10-100 nM; B = 101-250 Nm; C = 251-500 nM; D = 501-1,000 nM; E = >1,000 nM | Glycolysis IC50 in *P. falciparum*-infected RBCs A = 10-100 nM; B = 101-250 Nm; C = 251-500 nM; D = 501-1,000 nM; E = >1,000 nM |
|---|---|---|---|
| Example 27 | 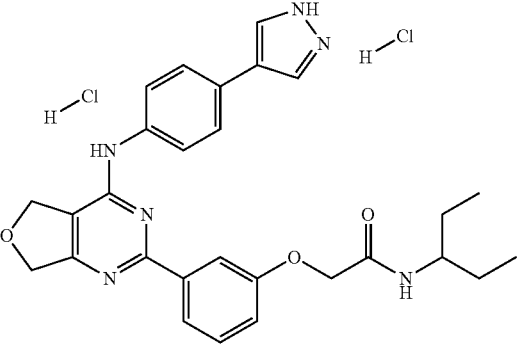 | A | A |
| Example 28 | 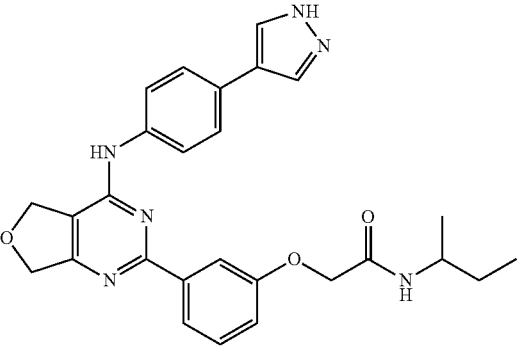 [SMILES: CCC(C)NC(=O)COc1cccc(-c2nc3c(c(Nc4ccc(-c5cn[nH]c5)cc4)n2)COC3)c1] | A | A |
| Example 29 | 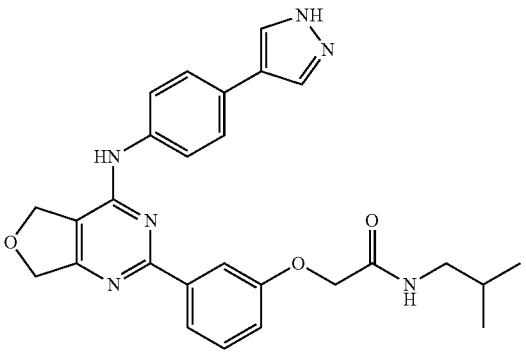 [SMILES: CC(C)CNC(=O)COc1cccc(-c2nc3c(c(Nc4ccc(-c5cn[nH]c5)cc4)n2)COC3)c1] | A | B |

TABLE 1-continued

Glycolysis IC50 values (nM)

| Example Number | Structure | Glycolysis IC50 in HT1080 cells A = 10-100 nM; B = 101-250 Nm; C = 251-500 nM; D = 501-1,000 nM; E = >1,000 nM | Glycolysis IC50 in *P. falciparum*-infected RBCs A = 10-100 nM; B = 101-250 Nm; C = 251-500 nM; D = 501-1,000 nM; E = >1,000 nM |
|---|---|---|---|
| Example 30 | 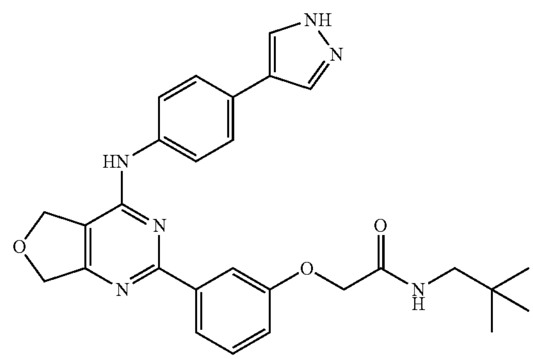 | A | B |
| Example 31 | 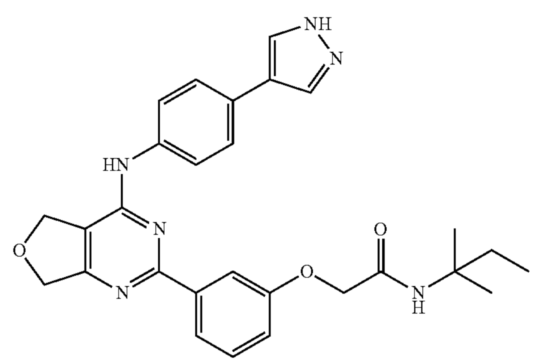 [SMILES: CCC(C)(C)NC(=O)COc1cccc(-c2nc3c(c(Nc4ccc(-c5cn[nH]c5)cc4)n2)COC3)c1] | A | B |
| Example 32 | 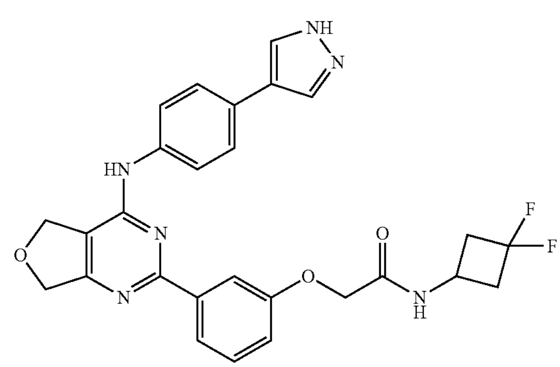 [SMILES: O=C(COc1cccc(-c2nc3c(c(Nc4ccc(-c5cn[nH]c5)cc4)n2)COC3)c1)NC1CC(F)(F)C1] | B | C |

TABLE 1-continued

Glycolysis IC50 values (nM)

| Example Number | Structure | Glycolysis IC50 in HT1080 cells A = 10-100 nM; B = 101-250 Nm; C = 251-500 nM; D = 501-1,000 nM; E = >1,000 nM | Glycolysis IC50 in *P. falciparum*-infected RBCs A = 10-100 nM; B = 101-250 Nm; C = 251-500 nM; D = 501-1,000 nM; E = >1,000 nM |
|---|---|---|---|
| Example 33 | 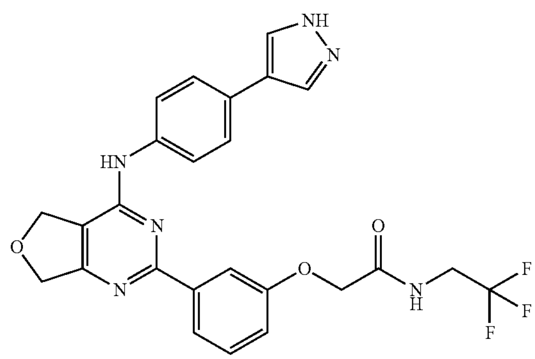 [SMILES: O=C(COc1cccc(-c2nc3c(c(Nc4ccc(-c5cn[nH]c5)cc4)n2)COC3)c1)NCC(F)(F)F] | D | C |
| Example 34 | 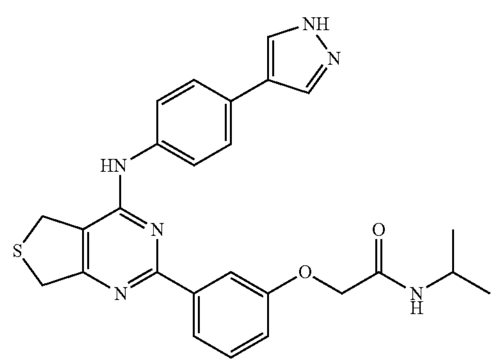 [SMILES: CC(C)NC(=O)COc1cccc(-c2nc3c(c(Nc4ccc(-c5cn[nH]c5)cc4)n2)CSC3)c1] | C | D |
| Example 35 | 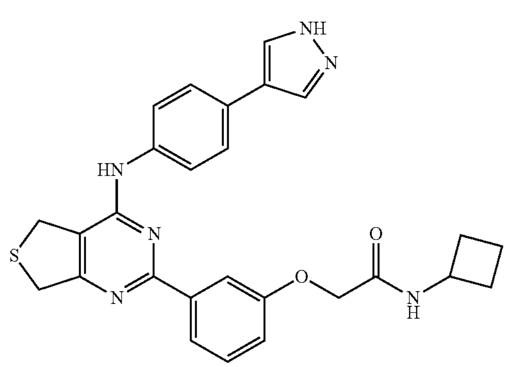 [SMILES: O=C(COc1cccc(-c2nc3c(c(Nc4ccc(-c5cn[nH]c5)cc4)n2)CSC3)c1)NC1CCC1] | B | D |

TABLE 1-continued

Glycolysis IC50 values (nM)

| Example Number | Structure | Glycolysis IC50 in HT1080 cells<br>A = 10-100 nM; B = 101-250 Nm; C = 251-500 nM; D = 501-1,000 nM; E = >1,000 nM | Glycolysis IC50 in *P. falciparum*-infected RBCs<br>A = 10-100 nM; B = 101-250 Nm; C = 251-500 nM; D = 501-1,000 nM; E = >1,000 nM |
|---|---|---|---|
| Example 36 | (structure) | B | D |
| Example 37 | (structure) | B | B |
| Example 38 | (structure) | C | A |

TABLE 1-continued

Glycolysis IC50 values (nM)

| Example Number | Structure | Glycolysis IC50 in HT1080 cells A = 10-100 nM; B = 101-250 Nm; C = 251-500 nM; D = 501-1,000 nM; E = >1,000 nM | Glycolysis IC50 in *P. falciparum*-infected RBCs A = 10-100 nM; B = 101-250 Nm; C = 251-500 nM; D = 501-1,000 nM; E = >1,000 nM |
|---|---|---|---|
| Example 39 | 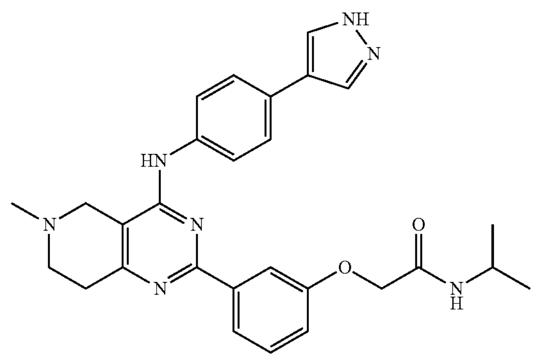 [SMILES: CC(C)NC(=O)COc1cccc(-c2nc3c(c(Nc4ccc(-c5cn[nH]c5)cc4)n2)CN(C)CC3)c1] | C | B |
| Example 40 | 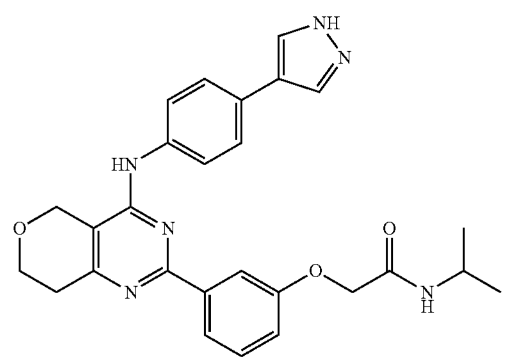 [SMILES: CC(C)NC(=O)COc1cccc(-c2nc3c(c(Nc4ccc(-c5cn[nH]c5)cc4)n2)COCC3)c1] | A | A |
| Example 41 | 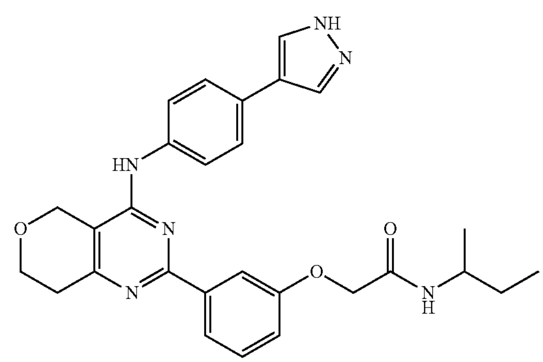 [SMILES: CCC(C)NC(=O)COc1cccc(-c2nc3c(c(Nc4ccc(-c5cn[nH]c5)cc4)n2)COCC3)c1] | A | A |

TABLE 1-continued
Glycolysis IC50 values (nM)
| Example Number | Structure | Glycolysis IC50 in HT1080 cells A = 10-100 nM; B = 101-250 Nm; C = 251-500 nM; D = 501-1,000 nM; E = >1,000 nM | Glycolysis IC50 in *P. falciparum*-infected RBCs A = 10-100 nM; B = 101-250 Nm; C = 251-500 nM; D = 501-1,000 nM; E = >1,000 nM |
|---|---|---|---|
| Example 42 | 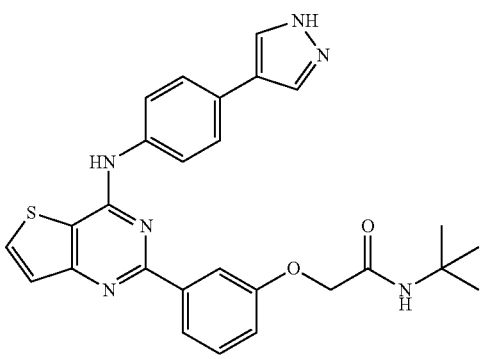 [SMILES: CC(C)(C)NC(=O)COc1cccc(-c2nc(Nc3ccc(-c4cn[nH]c4)cc3)c3sccc3n2)c1] | B | B |
| Example 43 | 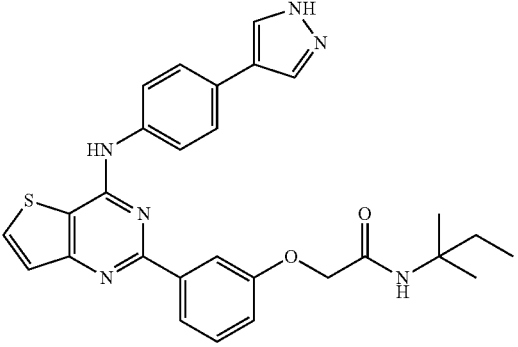 [SMILES: CCC(C)(C)NC(=O)COc1cccc(-c2nc(Nc3ccc(-c4cn[nH]c4)cc3)c3sccc3n2)c1] | B | A |
| Example 44 | 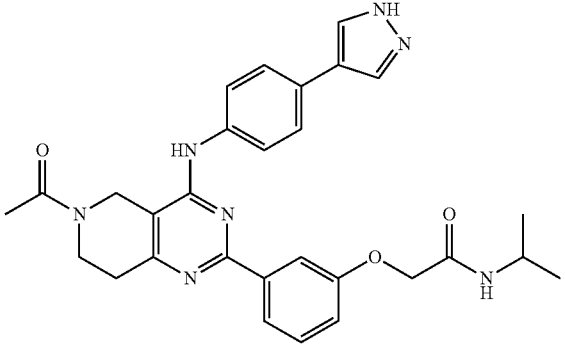 [SMILES: CC(=O)N1CCc2nc(-c3cccc(OCC(=O)NC(C)C)c3)nc(Nc3ccc(-c4cn[nH]c4)cc3)c2C1] | B | A |

TABLE 1-continued
Glycolysis IC50 values (nM)
| Example Number | Structure | Glycolysis IC50 in HT1080 cells A = 10-100 nM; B = 101-250 Nm; C = 251-500 nM; D = 501-1,000 nM; E = >1,000 nM | Glycolysis IC50 in *P. falciparum*-infected RBCs A = 10-100 nM; B = 101-250 Nm; C = 251-500 nM; D = 501-1,000 nM; E = >1,000 nM |
|---|---|---|---|
| Example 45 | 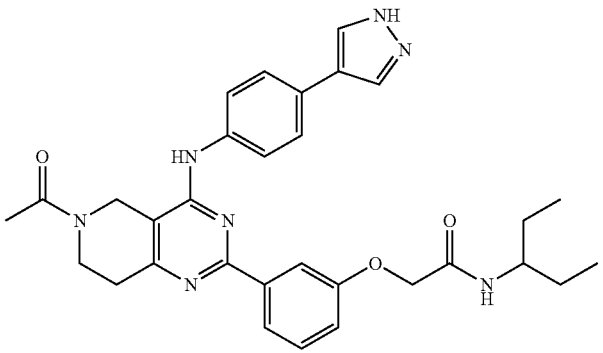 [SMILES: CCC(CC)NC(=O)COc1cccc(-c2nc3c(c(Nc4ccc(-c5cn[nH]c5)cc4)n2)CN(C(C)=O)CC3)c1] | A | A |
| Example 46 | 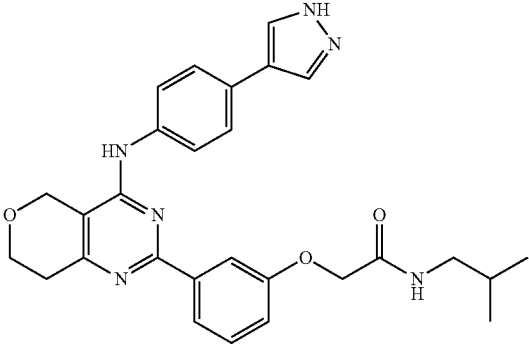 [SMILES: CC(C)CNC(=O)COc1cccc(-c2nc3c(c(Nc4ccc(-c5cn[nH]c5)cc4)n2)COCC3)c1] | A | A |
| Example 47 | 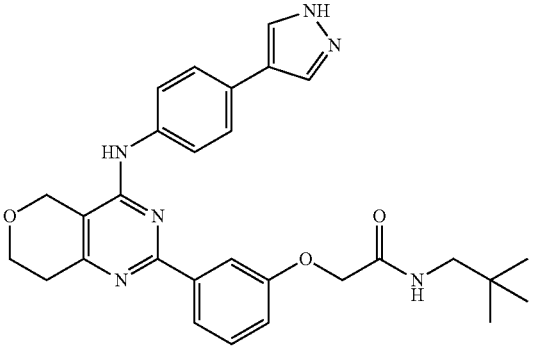 [SMILES: CC(C)(C)CNC(=O)COc1cccc(-c2nc3c(c(Nc4ccc(-c5cn[nH]c5)cc4)n2)COCC3)c1] | A | A |

TABLE 1-continued

Glycolysis IC50 values (nM)

| Example Number | Structure | Glycolysis IC50 in HT1080 cells<br>A = 10-100 nM;<br>B = 101-250 Nm; C = 251-500 nM; D = 501-1,000 nM;<br>E = >1,000 nM | Glycolysis IC50 in *P. falciparum-*infected RBCs<br>A = 10-100 nM;<br>B = 101-250 Nm; C = 251-500 nM; D = 501-1,000 nM;<br>E = >1,000 nM |
|---|---|---|---|
| Example 48 | 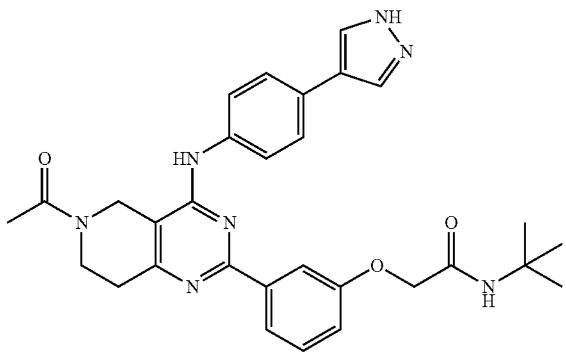 [SMILES: CC(=O)N1CCc2nc(-c3cccc(OCC(=O)NC(C)(C)C)c3)nc(Nc3ccc(-c4cn[nH]c4)cc3)c2C1] | A | A |
| Example 49 | 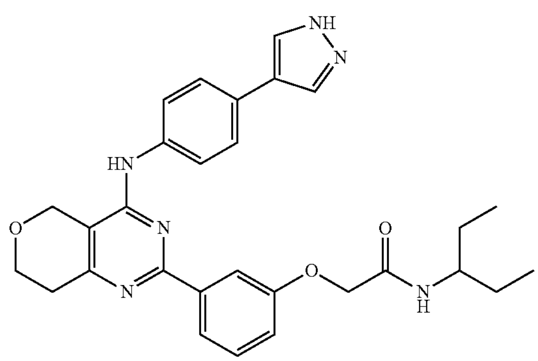 [SMILES: CCC(CC)NC(=O)COc1cccc(-c2nc3c(c(Nc4ccc(-c5cn[nH]c5)cc4)n2)COCC3)c1] | A | A |
| Example 50 | 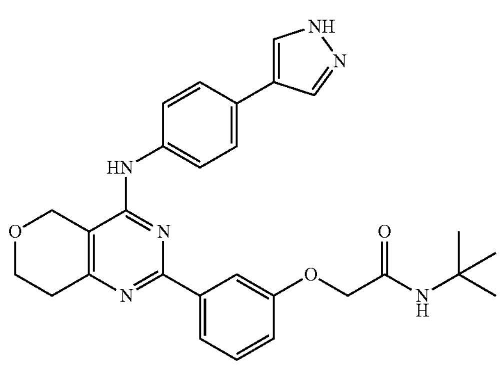 [SMILES: CC(C)(C)NC(=O)COc1cccc(-c2nc3c(c(Nc4ccc(-c5cn[nH]c5)cc4)n2)COCC3)c1] | A | A |

TABLE 1-continued
Glycolysis IC50 values (nM)
| Example Number | Structure | Glycolysis IC50 in HT1080 cells A = 10-100 nM; B = 101-250 Nm; C = 251-500 nM; D = 501-1,000 nM; E = >1,000 nM | Glycolysis IC50 in *P. falciparum*-infected RBCs A = 10-100 nM; B = 101-250 Nm; C = 251-500 nM; D = 501-1,000 nM; E = >1,000 nM |
|---|---|---|---|
| Example 51 | 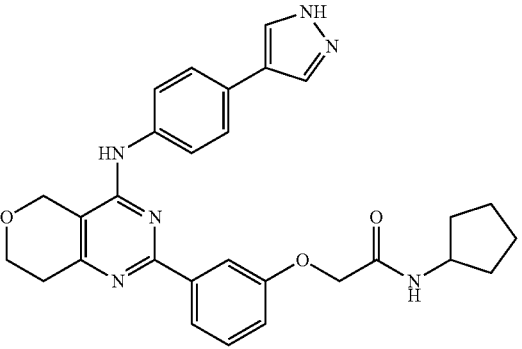 [SMILES: O=C(COc1cccc(-c2nc3c(c(Nc4ccc(-c5cn[nH]c5)cc4)n2)COCC3)c1)NC1CCCC1] | A | B |
| Example 52 | 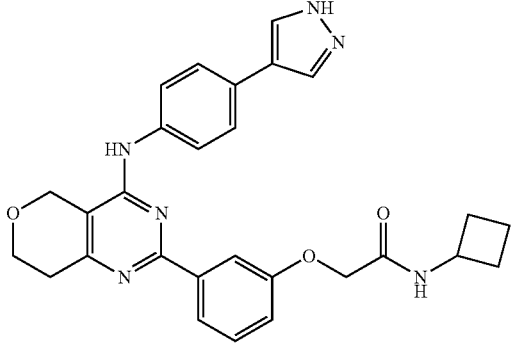 [SMILES: O=C(COc1cccc(-c2nc3c(c(Nc4ccc(-c5cn[nH]c5)cc4)n2)COCC3)c1)NC1CCC1] | A | B |
| Example 53 | 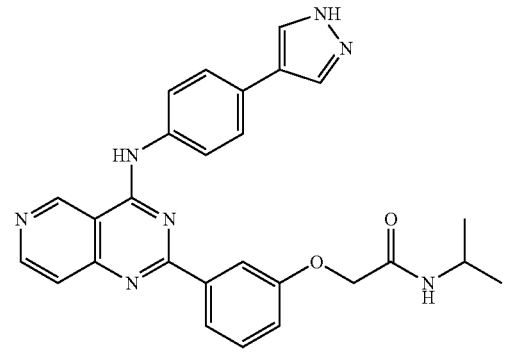 [SMILES: CC(C)NC(=O)COc1cccc(-c2nc(Nc3ccc(-c4cn[nH]c4)cc3)c3cnccc3n2)c1] | A | B |

TABLE 1-continued

Glycolysis IC50 values (nM)

| Example Number | Structure | Glycolysis IC50 in HT1080 cells A = 10-100 nM; B = 101-250 Nm; C = 251-500 nM; D = 501-1,000 nM; E = >1,000 nM | Glycolysis IC50 in *P. falciparum*-infected RBCs A = 10-100 nM; B = 101-250 Nm; C = 251-500 nM; D = 501-1,000 nM; E = >1,000 nM |
|---|---|---|---|
| Example 54 | 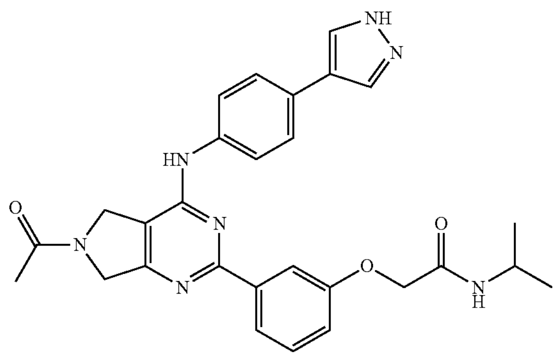 [SMILES: CC(=O)N1Cc2nc(-c3cccc(OCC(=O)NC(C)C)c3)nc(Nc3ccc(-c4cn[nH]c4)cc3)c2C1] | B | D |
| Example 55 | 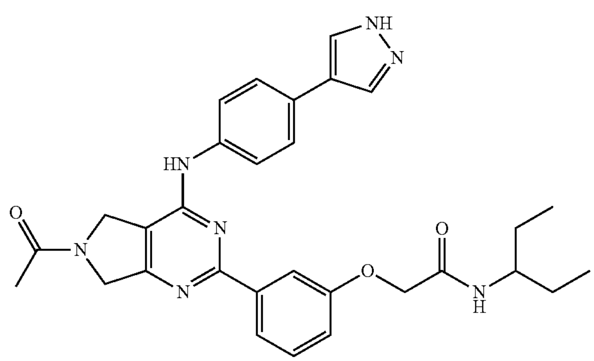 [SMILES: CCC(CC)NC(=O)COc1cccc(-c2nc3c(c(Nc4ccc(-c5cn[nH]c5)cc4)n2)CN(C(C)=O)C3)c1] | A | A |
| Example 56 | 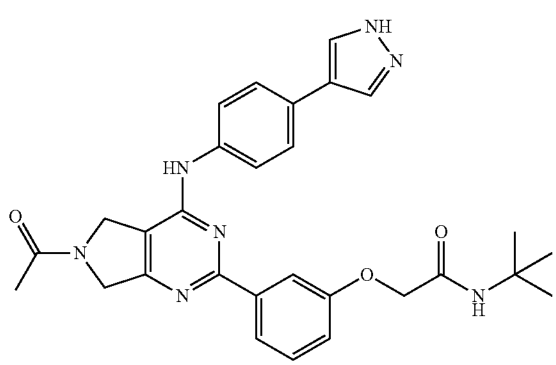 [SMILES: CC(=O)N1Cc2nc(-c3cccc(OCC(=O)NC(C)(C)C)c3)nc(Nc3ccc(-c4cn[nH]c4)cc3)c2C1] | A | B |

TABLE 1-continued

Glycolysis IC50 values (nM)

| Example Number | Structure | Glycolysis IC50 in HT1080 cells A = 10-100 nM; B = 101-250 Nm; C = 251-500 nM; D = 501-1,000 nM; E = >1,000 nM | Glycolysis IC50 in *P. falciparum*-infected RBCs A = 10-100 nM; B = 101-250 Nm; C = 251-500 nM; D = 501-1,000 nM; E = >1,000 nM |
|---|---|---|---|
| Example 57 | 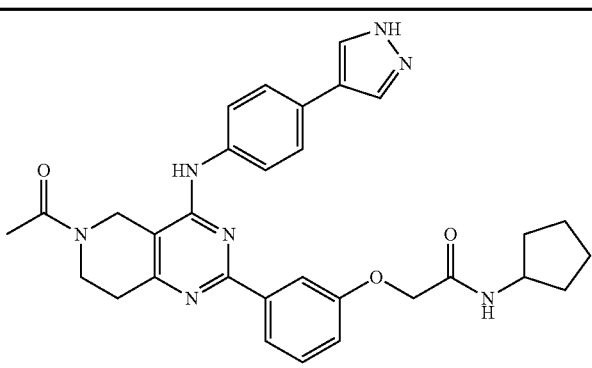 | A | B |
| Example 58 | 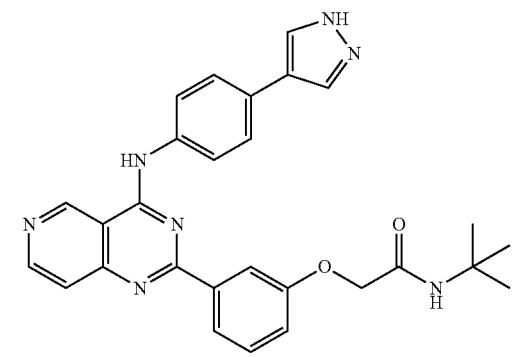 [SMILES: CC(C)(C)NC(=O)COc1cccc(-c2nc(Nc3ccc(-c4cn[nH]c4)cc3)c3cnccc3n2)c1] | A | B |
| Example 59 | 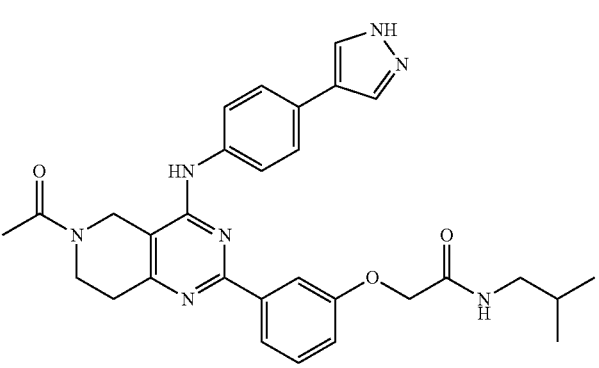 [SMILES: CC(=O)N1CCc2nc(-c3cccc(OCC(=O)NCC(C)C)c3)nc(Nc3ccc(-c4cn[nH]c4)cc3)c2C1] | A | B |

Methods

Determination of GLUT Activity:

ATP assay: HT1080 cells (as well as other cell types) were plated to confluency in 96-well plates. Cells were exposed to the combination of 10 μM Oligomycin (to block mitochondrial-derived ATP), and the glucose uptake inhibitor compounds for one-hour, after which glycolytically-derived ATP was measured with the Cell Titer-Glo assay kit (Promega). Dose-response curves of the glucose uptake inhibitor compounds were used to determine the IC50 for GLUT activity.

*Plasmodium* Culture

*P. falciparum* (HB-3 strain) cultures were maintained in standard culture conditions. Briefly, the culture medium consisted of modified RPMI (supplemented with 0.25% Albumax II, 0.2% sodium bicarbonate, 25 mM HEPES, 2.5 mg/L gentamicin, 0.005 mg/L hypoxanthine), and cultures were incubated at 37° C. in an atmosphere of 5% oxygen, 5% carbon dioxide and 90% nitrogen. Parasites were grown in O+ donor blood, 2% hematocrit.

Lactate Excretion Assays

Parasite cultures were seeded in 96-well plates (1% hematocrit, 1-2% starting parasitemia, 100 μL total volume)

with varying concentrations of the test compounds in a final concentration of 0.1% DMSO. Plates were cultured for 48 hours before harvesting the culture medium for LC-MS analysis. At harvest, thin smears were taken and examined microscopically to observe any alterations in parasite morphology.

Proliferation Assays

Parasite cultures were set up in 96-well plates (opaque, black plastic) as above. After 48 hours, the plates were sealed and frozen at −80° C. At the time of assay, plates were thawed at room temperature and 100 uL of assay buffer (20 mM Tris:HCl, pH 7.5; 5 mM EDTA; 0.08% Triton X-100; 0.008% saponin; 1×SYBR Green I) was added to each well. The plates were incubated at 37° C. for 4 hours and then the fluorescence intensity was measured (excitation/emission: 485 nm/535 nm). Uninfected erythrocyte cultures were treated and assayed at the same time to establish baseline fluorescence.

Metabolite Extractions

Cellular metabolite levels were determined in cultures that had been enriched for late stage (trophozoite/schizont)-infected erythrocytes by centrifuging a bulk culture suspension over a two-step Percoll gradient (65%/35% Percoll) at 1,500 RCF for 15 minutes and collecting the parasitized erythrocytes at the interface. 10 uL of packed cells were pelleted from the resulting cultures by centrifugation (500 RCF, 5 minutes), the culture medium removed by aspiration, and the cells extracted with 1.2 mL of 80% methanol/20% on dry ice. The first extraction was collected as the supernatant after centrifugation (1,000 RCF, 5 minutes) and the pellet extracted again with 0.3 mL of 80% methanol/20%. The two extracts were pooled, dried under nitrogen and resuspended in 200 uL of water prior to LC-MS analysis.

LC-MS Analysis

Culture medium samples were diluted in 9 volumes of methanol containing U-$^{13}$C-glucose and 1-$^{13}$C-lactate (final concentration 0.25 mM each). The samples were clarified by centrifugation at 13,000 RCF for 10 minutes. For analysis, 5 μL of sample was injected onto a 5 cm Luna aminopropyl column (Phenomenex) and run on the following gradient: initial composition 85:15 mobile phase A:mobile phase B; 0-1.5 minutes, ramp to 0:100; 1.5-3.8 minutes, 0:100; 3.8-4 minutes, ramp to 85:15; 4-5 minutes, 85:15. Mobile phase A was acetonitrile, and mobile phase B was 20 mM ammonium acetate (pH 9.4).

For cellular metabolite extracts, 10 uL of sample was injected onto a 10 cm Synergi Hydro-RP RP column (Phenomenex) and run on the following gradient: initial composition 100:0 mobile phase A:mobile phase B; 0-2.5 minutes, hold; 2.5-5 minutes, ramp to 80:20; 5-7.5 minutes, hold; 7.5-13 minutes, ramp to 45:55; 13-15.5 minutes, ramp to 5:95; 15.5-18.5 minutes, hold; 18.5-19 minutes, ramp to 100:0; 19-25 minutes, hold. Mobile phase A was 95% water/5% methanol, 10 mM tributylamine, 15 mM acetic acid, and mobile phase B was methanol.

The sample was analyzed on an Exactive mass spectrometer (Thermo Scientific) to determine the chromatographic peak areas the analytes and internal standards. Glucose and lactate were quantified by taking the ratio of the unlabeled peak area to the area of the isotope-labeled standard.

REFERENCES

1. Roth, E., Jr., *Plasmodium falciparum: carbohydrate metabolism: a connection between host cell and parasite.* Blood Cells, 1990. 16(2-3): p. 453-60; discussion 461-6.
2. Woodrow, C. J., J. I. Penny, and S. Krishna, *Intraerythrocytic Plasmodium falciparum expresses a high affinity facilitative hexose transporter.* J Biol Chem, 1999. 274 (11): p. 7272-7.
3. Kirk, K., H. A. Horner, and J. Kirk, *Glucose uptake in Plasmodium falciparum-infected erythrocytes is an equilibrative not an active process.* Mol Biochem Parasitol, 1996. 82(2): p. 195-205.
4. Babbitt, S. E., et al., *Plasmodium falciparum: responds to amino acid starvation by entering into a hibernatory state.* Proc Natl Acad Sci USA, 2012. 109(47): p. E3278-87.
5. Joet, T., et al., *Validation of the hexose transporter of Plasmodium falciparum as a novel drug target.* Proc Natl Acad Sci USA, 2003. 100(13): p. 7476-9.
6. Loisel-Meyer, S., et al., *Glut1-mediated glucose transport regulates HIV infection.* Proc Natl Acad Sci USA, 2012. 109(7): p. 2549-54.
7. Palmer, C. S., et al., *Increased glucose metabolic activity is associated with CD4+ T-cell activation and depletion during chronic HIV infection.* AIDS, 2014. 28(3): p. 297-309.
8. Mehrotra, P., et al., *Pathogenicity of Mycobacterium tuberculosis is expressed by regulating metabolic thresholds of the host macrophage.* PLoS Pathog, 2014. 10(7): p. e1004265.
9. Singh, A. K., et al., *Intracellular pathogen Leishmania donovani activates hypoxia inducible factor-1 by dual mechanism for survival advantage within macrophage.* PLoS One, 2012. 7(6): p. e38489.

What is claimed is:

1. A method of treating infectious diseases in a mammal comprising administering to a mammalian subject in need thereof a therapeutically effective amount of a compound or prodrug thereof, or pharmaceutically acceptable salt or ester of said compound or prodrug, wherein the compound is an inhibitor of glucose uptake having the formula I:

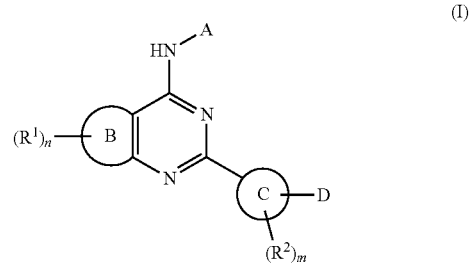

wherein:
A is selected from the group consisting of:

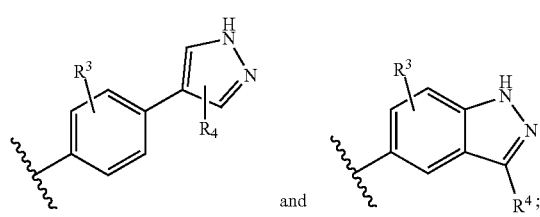

Ring B is a five- or six-membered ring containing 1 or 2 heteroatoms selected from the group consisting of N, O and S;

Ring C is a five- or six-membered aryl or heteroaryl ring containing from 0 to 2 heteroatoms selected from the group consisting of N, O and S;

each $R^1$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;

n is selected from 0, 1, or 2;

each $R^2$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;

m is selected from 0, 1, or 2;

$R^3$ and $R^4$ are H;

D is selected from the group consisting of —O—$(CH_2)_y$—C(=O)$NR^5R^6$, —O—C(=O)—$(CH_2)_y$—$NR^5R^6$, —O—$(CH_2)_y$—$NR^5R^6$, —NH—C(=O)—$(CH_2)_y$—$NR^5R^6$, —NH—C(=O)—$(CH_2)_y$—$R^7$, and —NH—$(CH_2)_y$—$NR^5R^6$;

y is selected from 1, 2, or 3;

$R^5$ and $R^6$ are independently selected from the group consisting of H, $C_1$-$C_6$ alkyl, $C_2$-$C_6$ alkenyl, $C_2$-$C_6$ alkynyl, —($C_1$-$C_6$ alkyl)-O—($C_1$-$C_6$ alkyl), aryl, aralkyl, heteroaryl, and $C_3$-$C_6$ cycloalkyl, or $R^5$ and $R^6$ may be taken together with the nitrogen to which they are attached to form a 5- to 6-membered heterocyclic ring having up to 3 heteroatoms selected from N, O, and S, and which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl; and $R^7$ is selected from the group consisting of aryl, heteroaryl, and a hetercyclic group.

2. The method of claim 1 wherein Ring B is a five-membered ring containing 1 or 2 heteroatoms selected from the group consisting of N, O and S.

3. The method of claim 1 wherein, the sub-structure

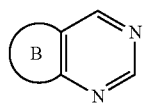

is selected from the group consisting of:

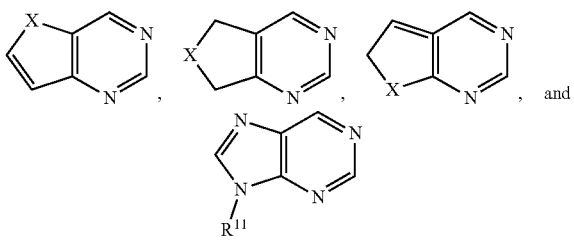

wherein X is selected from O and S, and $R^{11}$ is selected from H and $C_1$ to $C_6$ alkyl.

4. A method of treating infectious diseases in a mammal comprising administering to a mammalian subject in need thereof a therapeutically effective amount of a compound or prodrug thereof, or pharmaceutically acceptable salt or ester of said compound or prodrug, wherein the compound is an inhibitor of glucose uptake having the formula II:

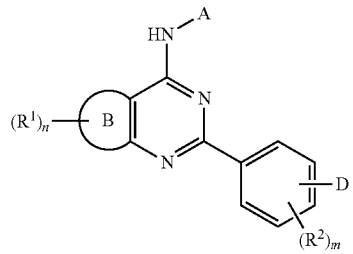

wherein:

A is selected from the group consisting of:

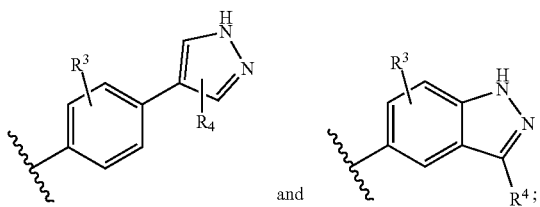

Ring B is a five- or six-membered ring containing 1 or 2 heteroatoms selected from the group consisting of N, O and S;

each $R^1$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;

n is selected from 0, 1, or 2;

each $R^2$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;

m is selected from 0, 1, or 2;

$R^3$ and $R^4$ are H;

D is selected from the group consisting of —O—$(CH_2)_y$—C(=O)$NR^5R^6$, —O—C(=O)—$(CH_2)_y$—$NR^5R^6$, —O—$(CH_2)_y$—$NR^5R^6$, —NH—C(=O)—$(CH_2)_y$—$NR^5R^6$, —NH—C(=O)—$(CH_2)_y$—$R^7$, and —NH—$(CH_2)_y$—$NR'R^6$;

y is selected from 1, 2, or 3;

$R^5$ and $R^6$ are independently selected from the group consisting of H, $C_1$-$C_6$ alkyl, $C_2$-$C_6$ alkenyl, $C_2$-$C_6$ alkynyl, —($C_1$-$C_6$ alkyl)-O—($C_1$-$C_6$ alkyl), aryl, aralkyl, heteroaryl, and $C_3$-$C_6$ cycloalkyl, or $R^5$ and $R^6$ may be taken together with the nitrogen to which they are attached to form a 5- to 6-membered heterocyclic ring having up to 3 heteroatoms selected from N, O, and S, and which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl; and $R^7$ is selected from the group consisting of aryl, heteroaryl, and a hetercyclic group.

5. A method of treating infectious diseases in a mammal comprising administering to a mammalian subject in need thereof a therapeutically effective amount of a compound, or pharmaceutically acceptable salt or ester of said compound, wherein the compound is an inhibitor of glucose uptake having the formula $III_a$:

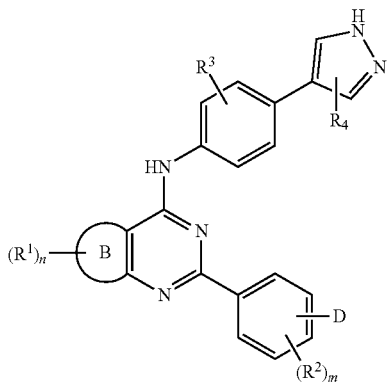

(IIIa)

wherein:

Ring B is a five- or six-membered ring containing 1 or 2 heteroatoms selected from the group consisting of N, O and S;

each $R^1$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;

n is selected from 0, 1, or 2;

each $R^2$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;

m is selected from 0, 1, or 2;

$R^3$ and $R^4$ are H;

D is selected from the group consisting of —O—$(CH_2)_y$—C(=O)$NR^5R^6$, —O—C(=O)—$(CH_2)_y$—$NR^5R^6$, —O—$(CH_2)_y$—$NR^5R^6$, —NH—C(=O)—$(CH_2)_y$—$NR^5R^6$, —NH—C(=O)—$(CH_2)_y$—$R^7$, and —NH—$(CH_2)_y$—NR'$R^6$;

y is selected from 1, 2, or 3;

$R^5$ and $R^6$ are independently selected from the group consisting of H, $C_1$-$C_6$ alkyl, $C_2$-$C_6$ alkenyl, $C_2$-$C_6$ alkynyl, —($C_1$-$C_6$ alkyl)-O—($C_1$-$C_6$ alkyl), aryl, aralkyl, heteroaryl, and $C_3$-$C_6$ cycloalkyl, or $R^5$ and $R^6$ may be taken together with the nitrogen to which they are attached to form a 5- to 6-membered heterocyclic ring having up to 3 heteroatoms selected from N, O, and S, and which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl; and $R^7$ is selected from the group consisting of aryl, heteroaryl, and a hetercyclic group.

6. The method of any one of claims 1-5 wherein the mammal is a human.

7. The method of claim 6 wherein the infectious disease is a parasitic or viral infection.

8. The method of claim 7 wherein the parasitic or viral infection is malaria, leishmaniasis, African trypanosomiasis, tuberculosis, HIV, HCMV or herpes virus.

9. The method of claim 8 wherein the parasitic or viral infection is malaria.

* * * * *